United States Patent
Karlstrom et al.

(10) Patent No.: US 9,000,182 B2
(45) Date of Patent: *Apr. 7, 2015

(54) 2H-IMIDAZOL-4-AMINE COMPOUNDS AND THEIR USE AS BACE INHIBITORS

(71) Applicant: AstraZeneca AB, Sodertalje (SE)

(72) Inventors: Sofia Karlstrom, Cheshire (GB); Gabor Csjernyik, Cheshire (GB); Britt-Marie Swahn, Cheshire (GB); Lars Sandberg, Cheshire (GB); Karin Kolmodin, Cheshire (GB); Peter Soderman, Cheshire (GB); Liselotte Ohberg, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/916,690

(22) Filed: Jun. 13, 2013

(65) Prior Publication Data

US 2013/0345246 A1    Dec. 26, 2013

Related U.S. Application Data

(60) Provisional application No. 61/661,919, filed on Jun. 20, 2012.

(51) Int. Cl.
| | |
|---|---|
| *C07D 235/02* | (2006.01) |
| *C07D 401/02* | (2006.01) |
| *A61K 31/4184* | (2006.01) |
| *A61K 31/4439* | (2006.01) |
| *A61K 45/06* | (2006.01) |
| *C07D 401/04* | (2006.01) |

(52) U.S. Cl.
CPC ............ *C07D 235/02* (2013.01); *C07D 401/02* (2013.01); *A61K 31/4184* (2013.01); *A61K 31/4439* (2013.01); *A61K 45/06* (2013.01); *C07D 401/04* (2013.01)

(58) Field of Classification Search
USPC ...................................................... 548/301.1
See application file for complete search history.

(56) References Cited

U.S. PATENT DOCUMENTS

| 8,415,483 B2 * | 4/2013 | Csjernyik et al. .......... 548/301.1 |
| 8,865,911 B2 * | 10/2014 | Csjernyik et al. .......... 548/301.1 |
| 2013/0210837 A1 * | 8/2013 | Csjernyik et al. ........ 514/255.05 |
| 2013/0345247 A1 | 12/2013 | Karlstrom et al. |
| 2013/0345248 A1 | 12/2013 | Karlstrom et al. |
| 2013/0345272 A1 | 12/2013 | Karlstrom et al. |
| 2014/0031379 A1 | 1/2014 | Bohlin et al. |

FOREIGN PATENT DOCUMENTS

| WO | WO2005094822 | 10/2005 |
| WO | WO2006138264 | 12/2006 |
| WO | WO2007076247 | 7/2007 |
| WO | WO2007100536 | 9/2007 |
| WO | WO2008076043 | 6/2008 |
| WO | WO2009100169 | 8/2009 |
| WO | WO2010013794 | 2/2010 |
| WO | WO2010021680 | 2/2010 |
| WO | WO2010030954 | 3/2010 |
| WO | WO2010105179 | 9/2010 |
| WO | WO2011002407 | 1/2011 |
| WO | WO2011002408 | 1/2011 |
| WO | WO2011106414 | 9/2011 |
| WO | WO2011123674 | 10/2011 |
| WO | WO2011130741 | 10/2011 |
| WO | WO2012019056 | 2/2012 |
| WO | WO2012040641 | 3/2012 |
| WO | WO2012071458 | 5/2012 |
| WO | WO2012087237 | 6/2012 |

OTHER PUBLICATIONS

Thompson et al., Current Medicinal Chemistry, Oct. 2002, 9(19), pp. 1751-1762.*
Evin et al., "BACE inhibitors as potential therapeutics for Alzheimer's disease," Recent Patents on CNS Drug Discovery, Bentham Science Publishers Ltd, NL, vol. 2, No. 3, Nov. 1, 2007, pp. 188-199.
Hong et al., "Structure of the Protease Domain of Memapsin 2 (β-Secretase) Complexed with Inhibitor," Science 2000, 290, 5489, pp. 150-153.
John et al, "Human β-Secretase (BACE) and BACE Inhibitors," Journal of Medicinal Chemistry, 2003, 46, pp. 4625-4630.

(Continued)

Primary Examiner — Laura L. Stockton
(74) Attorney, Agent, or Firm — Ropes & Gray LLP

(57) ABSTRACT

2H-imidazol-4-amine compounds, therapeutically acceptable salts thereof, processes for preparation thereof, therapeutic uses of such compounds for treating Aβ-related pathologies such as Down's syndrome, β-amyloid angiopathy, Alzheimer's disease, memory loss, attention deficit symptoms associated with Alzheimer's disease, neurodegeneration associated with diseases such as Alzheimer's disease or dementia including dementia of mixed vascular and degenerative origin, pre-senile dementia, senile dementia and dementia associated with Parkinson's disease, progressive supranuclear palsy or cortical basal degeneration. methods of therapy, and pharmaceutical compositions containing such compounds.

7 Claims, No Drawings

(56) References Cited

OTHER PUBLICATIONS

Roberds et al, "BACE knockout mice are healthy despite lacking the primary β-secretase activity in brain: implications for Alzheimer's disease therapeutics," Human Molecular Genetics, 2001, 10, pp. 1317-1324.

Sinha et al, "Purification and cloning of amyloid precursor protein β-secretase from human brain," Nature, 1999, 402, pp. 537-540.

* cited by examiner

2H-IMIDAZOL-4-AMINE COMPOUNDS AND THEIR USE AS BACE INHIBITORS

CROSS-REFERENCE TO RELATED APPLICATIONS

This application claims the benefit under 35 U.S.C. §119 (e) to U.S. Application No. 61/661,919 filed on Jun. 20, 2012, which is incorporated herein by reference.

FIELD OF THE INVENTION

The present invention relates to 2H-imidazol-4-amine compounds and therapeutically acceptable salts thereof, their pharmaceutical compositions, processes for making them and their use as medicaments for treatment and/or prevention of various diseases. In particular the invention relates to compounds, which are inhibitors of β-secretase and hence inhibit the formation of amyloid β (Aβ) peptides and will be used for treatment and/or prevention of Aβ-related pathologies such as Alzheimer's disease, Down's syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer's disease, memory loss, attention deficit symptoms associated with Alzheimer's disease, neurodegeneration associated with diseases such as Alzheimer's disease or dementia including dementia of mixed vascular and degenerative origin, pre-senile dementia, senile dementia and dementia associated with Parkinson's disease, progressive supranuclear palsy or cortical basal degeneration.

BACKGROUND

The prime neuropathological event distinguishing Alzheimer's disease (AD) is deposition of the 40-42 residue amyloid β-peptide (Aβ) in brain parenchyma and cerebral vessels. A large body of genetic, biochemical and in vivo data support a pivotal role for Aβ in the pathological cascade that eventually leads to AD. Patients usually present early symptoms (commonly memory loss) in their sixth or seventh decades of life. The disease progresses with increasing dementia and elevated deposition of Aβ. In parallel, a hyperphosphorylated form of the microtubule-associated protein tau accumulates within neurons, leading to a plethora of deleterious effects on neuronal function. The prevailing working hypothesis regarding the temporal relationship between Aβ and tau pathologies states that Aβ deposition precedes tau aggregation in humans and animal models of the disease. Within this context, it is worth noting that the exact molecular nature of Aβ, mediating this pathological function is presently an issue under intense study. Most likely, there is a continuum of toxic species ranging from lower order Aβ oligomers to supramolecular assemblies such as Aβ fibrils.

The Aβ peptide is an integral fragment of the Type I protein APP (Aβ amyloid precursor protein), a protein ubiquitously expressed in human tissues. Since soluble Aβ can be found in both plasma and cerebrospinal fluid (CSF), and in the medium from cultured cells, APP has to undergo proteolysis. There are three main cleavages of APP that are relevant to the pathobiology of AD, the so-called α-, β-, and γ-cleavages. The α-cleavage, which occurs roughly in the middle of the Aβ domain in APP is executed by the metalloproteases ADAM 10 or ADAM 17 (the latter also known as TACE). The β-cleavage, occurring at the N terminus of Aβ, is generated by the transmembrane aspartyl protease Beta site APP Cleaving Enzyme1 (BACE1). The γ-cleavage, generating the Aβ C termini and subsequent release of the peptide, is effected by a multi-subunit aspartyl protease named γ-secretase. ADAM10/17 cleavage followed by γ-secretase cleavage results in the release of the soluble p3 peptide, an N-terminally truncated Aβ fragment that fails to form amyloid deposits in humans. This proteolytic route is commonly referred to as the non-amyloidogenic pathway. Consecutive cleavages by BACE1 and γ-secretase generates the intact Aβ peptide, hence this processing scheme has been termed the amyloidogenic pathway. With this knowledge at hand, it is possible to envision two possible avenues of lowering Aβ production: stimulating non-amyloidogenic processing, or inhibit or modulate amyloidogenic processing. This application focuses on the latter strategy, inhibition or modulation of amyloidogenic processing.

Amyloidogenic plaques and vascular amyloid angiopathy also characterize the brains of patients with Trisomy 21 (Down's Syndrome), Hereditary Cerebral Hemorrhage with Amyloidosis of the Dutch-type (HCHWA-D), and other neurodegenerative disorders. Neurofibrillary tangles also occur in other neurodegenerative disorders including dementia-inducing disorders (Varghese, J., et al, Journal of Medicinal Chemistry, 2003, 46, 4625-4630). β-amyloid deposits are predominately an aggregate of Aβ peptide, which in turn is a product of the proteolysis of amyloid precursor protein (APP). More specifically, Aβ peptide results from the cleavage of APP at the C-terminus by one or more γ-secretases, and at the N-terminus by β-secretase enzyme (BACE), also known as aspartyl protease or Asp2 or Beta site APP Cleaving Enzyme (BACE), as part of the β-amyloidogenic pathway.

BACE activity is correlated directly to the generation of Aβ peptide from APP (Sinha, et al, Nature, 1999, 402, 537-540), and studies increasingly indicate that the inhibition of BACE inhibits the production of Aβ peptide (Roberds, S. L., et al, Human Molecular Genetics, 2001, 10, 1317-1324). BACE is a membrane bound type 1 protein that is synthesized as a partially active proenzyme, and is abundantly expressed in brain tissue. It is thought to represent the major β-secretase activity, and is considered to be the rate-limiting step in the production of amyloid-β-peptide (Aβ).

Drugs that reduce or block BACE activity should therefore reduce Aβ levels and levels of fragments of Aβ in the brain, or elsewhere where Aβ or fragments thereof deposit, and thus slow the formation of amyloid plaques and the progression of AD or other maladies involving deposition of Aβ or fragments thereof. BACE is therefore an important candidate for the development of drugs as a treatment and/or prophylaxis of Aβ-related pathologies such as Down's syndrome, β-amyloid angiopathy such as but not limited to cerebral amyloid angiopathy or hereditary cerebral hemorrhage, disorders associated with cognitive impairment such as but not limited to MCI ("mild cognitive impairment"), Alzheimer's Disease, memory loss, attention deficit symptoms associated with Alzheimer's disease, neurodegeneration associated with diseases such as Alzheimer's disease or dementia including dementia of mixed vascular and degenerative origin, pre-senile dementia, senile dementia and dementia associated with Parkinson's disease, progressive supranuclear palsy or cortical basal degeneration.

It would therefore be useful to inhibit the deposition of Aβ and portions thereof by inhibiting BACE through inhibitors such as the compounds provided herein.

The therapeutic potential of inhibiting the deposition of Aβ has motivated many groups to isolate and characterize secretase enzymes and to identify their potential inhibitors.

DETAILED DESCRIPTION OF THE INVENTION

The present invention is directed to compounds according to formula (I):

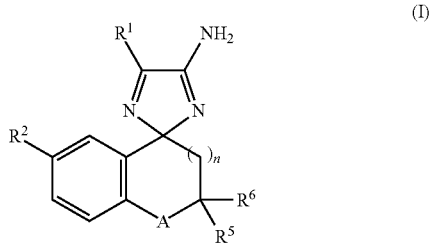

wherein
A is —O— or —CH$_2$—;
n is 0 or 1;
R$^1$ is C$_{1-6}$alkyl or C$_{1-6}$haloalkyl;
R$^2$ is hydrogen, C$_{0-6}$alkylaryl, C$_{0-6}$alkylheteroaryl, C$_{2-6}$alkynyl, C$_{2-6}$alkenyl, C$_{1-6}$alkyl, halogen, cyano, C$_{1-6}$haloalkyl, NHC(O)R$^9$ or OR$^8$, wherein said C$_{0-6}$alkylaryl, C$_{0-6}$alkylheteroaryl, C$_{2-6}$alkynyl, C$_{2-6}$alkenyl, C$_{1-6}$alkyl, or C$_{1-6}$haloalkyl is optionally substituted with one to three R$^7$;
R$^5$ and R$^6$ are independently hydrogen, heterocyclyl, C$_{3-6}$cycloalkyl, aryl, heteroaryl or C$_{1-6}$alkyl, wherein said heterocyclyl, C$_{3-6}$cycloalkyl, aryl, heteroaryl or C$_{1-6}$alkyl is optionally substituted with one or two substituents independently selected from halogen, C$_{1-6}$alkyl, C$_{1-6}$haloalkyl, cyano, or OR$^8$; or R$^5$ and R$^6$ together with the carbon to which they are attached, form a ring B, which is a 3-14 membered cycloalkyl or heterocyclyl monocyclic ring, or a 9-14 membered bicyclic cycloalkyl or heterocyclyl ring; and wherein ring B is optionally substituted by one or two substituents independently selected from oxo, halogen, C$_{1-6}$alkyl, C$_{1-6}$haloalkyl, cyano, or OR$^8$; and ring B is optionally fused with an aryl or heteroaryl to form a bi- or polycyclic system;
R$^7$ is independently C$_{1-6}$alkyl, halogen, cyano, C$_{0-6}$alkylC$_{3-6}$cycloalkyl, C$_{1-6}$haloalkyl, OC$_{1-6}$alkyl, OC$_{1-6}$haloalkyl, C$_{2-6}$alkynyl or C$_{2-6}$alkenyl, wherein said C$_{1-6}$alkyl, C$_{0-6}$alkylC$_{3-6}$cycloalkyl, C$_{1-6}$haloalkyl, OC$_{1-6}$alkyl, OC$_{1-6}$haloalkyl, C$_{2-6}$alkynyl or C$_{2-6}$alkenyl is optionally substituted with 1-3 substituents independently selected from halogen, cyano, C$_{1-6}$alkyl, C$_{1-6}$haloalkyl, OC$_{1-6}$alkyl, and OC$_{1-6}$haloalkyl;
R$^8$ is independently hydrogen, C$_{1-6}$alkyl, C$_{2-6}$alkynyl, C$_{1-6}$haloalkyl, aryl or heteroaryl; wherein said C$_{1-6}$alkyl, C$_{1-6}$haloalkyl, aryl or heteroaryl is optionally substituted with a group selected from halogen, cyano, and C$_{1-6}$alkyl;
R$^9$ is a heteroaryl; wherein said heteroaryl is optionally substituted with halogen, cyano, OR$^8$, C$_{1-6}$haloalkyl or C$_{1-6}$alkyl;
as a free base or a pharmaceutically acceptable salt thereof.

In a particular embodiment, the present invention is directed to a compound of Formula I selected from the group consisting of:
(1r,4r)-4"-Amino-5"-methyl-6'-(2-methylpropoxy)-3'H-dispiro[cyclohexane-1,2'-indene-1',2"-imidazol]-4-ol;
(1r,1'R,4R)-4"-Amino-5"-methyl-6'-(2-methylpropoxy)-3'H-dispiro[cyclohexane-1,2'-indene-1',2"-imidazol]-4-ol;
(1r,1'S,4S)-4"-Amino-5"-methyl-6'-(2-methylpropoxy)-3'H-dispiro[cyclohexane-1,2'-indene-1',2"-imidazol]-4-ol;
(1r,4r)-6'-(2,2-Difluoropropoxy)-4-methoxy-5"-methyl-3'H-dispiro[cyclohexane-1,2'-indene-1',2"-imidazol]-4"-amine;
(1r,4r)-4"-Amino-6'-bromo-5"-methyl-3'H-dispiro[cyclohexane-1,2'-indene-1',2"-imidazol]-4-ol;
(1r,1'R,4R)-4"-Amino-6'-bromo-5"-methyl-3'H-dispiro[cyclohexane-1,2'-indene-1',2"-imidazol]-4-ol;
(1r,1'S,4S)-4"-Amino-6'-bromo-5"-methyl-3'H-dispiro[cyclohexane-1,2'-indene-1',2"-imidazol]-4-ol;
(1r,4r)-6'-(Cyclobutylethynyl)-4-methoxy-5"-methyl-3'H-dispiro[cyclohexane-1,2'-indene-1',2"-imidazol]-4"-amine;
(1r,1'R,4R)-6'-(Cyclobutylethynyl)-4-methoxy-5"-methyl-3'H-dispiro[cyclohexane-1,2'-indene-1',2"-imidazol]-4"-amine;
(1r,1'S,4S)-6'-(Cyclobutylethynyl)-4-methoxy-5"-methyl-3'H-dispiro[cyclohexane-1,2'-indene-1',2"-imidazol]-4"-amine;
(1r,4r)-4-Methoxy-5"-methyl-6'-(3-methylbut-1-yn-1-yl)-3'H-dispiro[cyclohexane-1,2'-indene-1',2"-imidazol]-4"-amine;
(1r,1'R,4R)-4-Methoxy-5"-methyl-6'-(3-methylbut-1-yn-1-yl)-3'H-dispiro[cyclohexane-1,2'-indene-1',2"-imidazol]-4"-amine;
(1r,1'S,4S)-4-Methoxy-5"-methyl-6'-(3-methylbut-1-yn-1-yl)-3'H-dispiro[cyclohexane-1,2'-indene-1',2"-imidazol]-4"-amine;
(1r,4r)-4-Methoxy-5"-methyl-6'-(3,3,3-trifluoropropoxy)-3'H-dispiro[cyclohexane-1,2'-indene-1',2"-imidazol]-4"-amine;
(1r,1'R,4R)-4-Methoxy-5"-methyl-6'-(3,3,3-trifluoropropoxy)-3'H-dispiro[cyclohexane-1,2'-indene-1',2"-imidazol]-4"-amine;
(1r,1'S,4S)-4-Methoxy-5"-methyl-6'-(3,3,3-trifluoropropoxy)-3'H-dispiro[cyclohexane-1,2'-indene-1',2"-imidazol]-4"-amine;
(1r,4r)-4-(Difluoromethoxy)-6'-(3-fluoropropoxy)-5"-methyl-3'H-dispiro[cyclohexane-1,2'-indene-1',2"-imidazol]-4"-amine;
(1r,1'R,4R)-4-(Difluoromethoxy)-6'-(3-fluoropropoxy)-5"-methyl-3'H-dispiro[cyclohexane-1,2'-indene-1',2"-imidazol]-4"-amine;
(1r,1'S,4S)-4-(Difluoromethoxy)-6'-(3-fluoropropoxy)-5"-methyl-3'H-dispiro[cyclohexane-1,2'-indene-1',2"-imidazol]-4"-amine;
(1r,4r)-6'-(2-Fluoropropoxy)-4-methoxy-5"-methyl-3'H-dispiro[cyclohexane-1,2'-indene-1',2"-imidazol]-4"-amine;
3-[(1r,1'R,4R)-4"-Amino-4-hydroxy-5"-methyl-3'H-dispiro[cyclohexane-1,2'-indene-1',2"-imidazol]-6'-yl]-5-chlorobenzonitrile;
3-[(1r,1'S,4S)-4"-Amino-4-hydroxy-5"-methyl-3'H-dispiro[cyclohexane-1,2'-indene-1',2"-imidazol]-6'-yl]-5-chlorobenzonitrile;
(1r,4r)-6'-Bromo-5"-methyl-4-(propan-2-yloxy)-3'H-dispiro[cyclohexane-1,2'-indene-1',2"-imidazol]-4"-amine;
(1r,4r)-6'-(3-Fluoropropoxy)-5"-methyl-4-(propan-2-yloxy)-3'H-dispiro[cyclohexane-1,2'-indene-1',2"-imidazol]-4"-amine;
(1r,4r)-6'-[(2S)-Butan-2-yloxy]-4-methoxy-5"-methyl-3'H-dispiro[cyclohexane-1,2'-indene-1',2"-imidazol]-4"-amine;
(1r,1'R,4R)-4"-Amino-4-methoxy-5"-methyl-3'H-dispiro[cyclohexane-1,2'-indene-1',2"-imidazol]-6'-ol;
(1r,4r)-4"-Amino-5"-methyl-6'-[5-(prop-1-yn-1-yl)pyridin-3-yl]-3'H-dispiro[cyclohexane-1,2'-indene-1',2"-imidazol]-4-ol;

(1r,1'R,4R)-4"-Amino-5"-methyl-6'-[5-(prop-1-yn-1-yl)pyridin-3-yl]-3'H-dispiro[cyclohexane-1,2'-indene-1',2"-imidazol]-4-ol, and (1r,1'S,4S)-4"-Amino-5"-methyl-6'-[5-(prop-1-yn-1-yl)pyridin-3-yl]-3'H-dispiro[cyclohexane-1,2'-indene-1',2"-imidazol]-4-ol, or a pharmaceutically acceptable salt of any foregoing compound.

The present invention relates to the use of compounds according to the present invention as well as to the salts thereof. Salts for use in pharmaceutical compositions will be pharmaceutically acceptable salts, but other salts may be useful in the production of the compounds according to the present invention.

The compounds according to the present invention may be administered in the form of a prodrug which is broken down in the human or animal body to give a compound according to the present invention. Examples of prodrugs include in vivo hydrolysable esters of a compound according to the present invention. An in vivo hydrolysable (or cleavable) ester of a compound according to the present invention that contains a carboxy or a hydroxy group is, for example, a pharmaceutically acceptable ester which is hydrolysed in the human or animal body to produce the parent acid or alcohol. Various forms of prodrugs are known in the art.

The definitions set forth in this application are intended to clarify terms used throughout this application. The term "herein" means the entire application.

A variety of compounds in the present invention may exist in particular geometric or stereoisomeric forms. The present invention takes into account all such compounds, including tautomers, cis- and trans isomers, R- and S-enantiomers, diastereomers, (D)-isomers, (L)-isomers, the racemic mixtures thereof, and other mixtures thereof, as being covered within the scope of this invention. Additional asymmetric carbon atoms may be present in a substituent such as an alkyl group. All such isomers, as well as mixtures thereof, are intended to be included in this invention. The compounds herein described may have asymmetric centers. Compounds of the present invention containing an asymmetrically substituted atom may be isolated in optically active or racemic forms. It is well known in the art how to prepare optically active forms, such as is by resolution of racemic forms, by synthesis from optically active starting materials, or synthesis using optically active reagents. When required, separation of the racemic material can be achieved by methods known in the art. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

As used herein, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the non-toxic salts or the quaternary ammonium salts of the parent compound formed, for example, from non-toxic inorganic or organic acids. For example, such non-toxic salts include those derived from inorganic acids such as hydrochloric acid.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like diethyl ether, ethyl acetate, ethanol, isopropanol, or acetonitrile are used.

The present invention further includes all tautomeric forms of compounds of the invention.

As used herein, "tautomer" means other structural isomers that exist in equilibrium resulting is from the migration of a hydrogen atom. For example, keto-enol tautomerism where the resulting compound has the properties of both a ketone and an unsaturated alcohol. Other examples of tautomerism include 2H-imidazole-4-amine and its tautomer 1,2-dihydroimidazol-5-imine, and 2H-imidazol-4-thiol and its tautomer 1,2-dihydroimidazol-5-thione. It is understood that in compound representations throughout this description, only one of the possible tautomers of the compound is drawn or named.

As used herein "stable compound" and "stable structure" are meant to indicate a compound that is sufficiently robust to survive isolation to a useful degree of purity from a reaction mixture, and formulation into an efficacious therapeutic agent.

Compounds of the invention further include hydrates and solvates.

The present invention further includes isotopically-labelled compounds of the invention. An "isotopically" or "radio-labelled" compound is a compound of the invention where one or more atoms are replaced or substituted by an atom having an atomic mass or mass number different from the atomic mass or mass number typically found in nature (i.e., naturally occurring). Suitable isotopes that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labelled compounds will depend on the specific application of that radio-labelled compound. For example, for in vitro receptor labelling and competition assays, compounds that incorporate $^{3}H$, $^{14}C$, $^{82}Br$, $^{125}I$, $^{131}I$ or $^{35}S$ will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labelled compound" is a compound that has incorporated at least one radionuclide. In some embodiments the radionuclide is selected from the group consisting of $^{3}H$, $^{14}C$, $^{125}I$, $^{35}S$ and $^{82}Br$.

Compounds of the present invention may be administered orally, parenteral, buccal, vaginal, rectal, inhalation, insufflation, sublingually, intramuscularly, subcutaneously, topically, intranasally, intraperitoneally, intrathoracically, intravenously, epidurally, intrathecally, intracerebroventricularly and by injection into the joints.

The dosage will depend on the route of administration, the severity of the disease, age and weight of the patient and other factors normally considered by the attending physician, when determining the individual regimen and dosage level as the most appropriate for a particular patient.

The quantity of the compound to be administered will vary for the patient being treated and will vary from about 100 ng/kg of body weight to 100 mg/kg of body weight per day. For instance, dosages can be readily ascertained by those skilled in the art from this disclosure and the knowledge in the art. Thus, the skilled artisan can readily determine the amount of compound and optional additives, vehicles, and/or carrier in compositions and to be administered in methods of the invention.

In another aspect, the invention relates to a compound according to the present invention, or a pharmaceutically acceptable salt thereof, for use as a medicament, e.g. for treatment or prevention of Aβ-related pathologies.

In another aspect, the invention relates to the use of a compound according to the present invention, or a pharmaceutically acceptable salt thereof, in the manufacture of a medicament for treatment or prevention of Aβ-related pathologies.

In another aspect, the invention relates to a method of treating or preventing Aβ-related pathologies in a mammal, such as a human being, comprising administering to a mammal in need thereof a therapeutically effective amount of a compound according to the present invention, or a pharmaceutically acceptable salt thereof.

The compounds of the invention, and their pharmaceutically acceptable salts, thereby provide methods of treatment of Aβ-related pathologies, such as, but not limited to, Alzheimer's disease, Down's syndrome, β-amyloid angiopathy, cerebral amyloid angiopathy, hereditary cerebral hemorrhage, a disorder associated with cognitive impairment, MCI ("mild cognitive impairment"), memory loss, attention deficit symptoms associated with Alzheimer's disease, neurodegeneration associated with Alzheimer's disease, dementia of mixed vascular origin, dementia of degenerative origin, presenile dementia, senile dementia, dementia associated with Parkinson's disease, progressive supranuclear palsy traumatic brain injury and cortical basal degeneration.

In another aspect, the invention relates to a pharmaceutical composition comprising as active ingredient a therapeutically effective amount of a compound according to the present invention, or a pharmaceutically acceptable salt thereof, in association with at least one pharmaceutically acceptable excipient, carrier or diluent.

In another aspect, the invention relates to a method of inhibiting activity of BACE with a compound according to the present invention.

In another aspect, the invention relates to a method of treating or preventing an Aβ-related pathology in a mammal, such as a human being, comprising administering to said patient a therapeutically effective amount of a compound according to the present invention, or a pharmaceutically acceptable salt thereof, and at least one cognitive enhancing agent, memory enhancing agent, or choline esterase inhibitor, wherein said Aβ-related pathology is Alzheimer's disease.

In another aspect, the invention relates to a pharmaceutical composition comprising (i) a compound according to the present invention, or a pharmaceutically acceptable salt thereof, (ii) an additional therapeutic agent, or a pharmaceutically acceptable salt thereof, and (iii) pharmaceutically acceptable excipients, carriers or diluents.

In another aspect, the invention relates to a pharmaceutical composition comprising (i) a compound according to the present invention, or a pharmaceutically acceptable salt thereof, (ii) at least one agent selected from the group consisting of cognitive enhancing agents, memory enhancing agents and choline esterase inhibitors, and (iii) pharmaceutically acceptable excipients, carriers or diluents.

The treatment of Aβ-related pathology defined herein may be applied as a mono therapy or may involve, in addition to the compound of the invention, conjoint treatment with conventional therapy of value in treating one or more disease conditions referred to herein. Such conventional therapy may include one or more of the following categories of agents: acetyl cholinesterase inhibitors, anti-inflammatory agents, cognitive and/or memory enhancing agents or atypical antipsychotic agents. Cognitive enhancing agents, memory enhancing agents and acetyl choline esterase inhibitors includes, but not limited to, donepezil (ARICEPT), galantamine (REMINYL or RAZADYNE), rivastigmine (EXELON), tacrine (COGNEX) and memantine (NAMENDA, AXURA or EBIXA). Atypical antipsychotic agents includes, but not limited to, olanzapine (marketed as ZYPREXA), aripiprazole (marketed as ABILIFY), risperidone (marketed as RISPERDAL), quetiapine (marketed as SEROQUEL), clozapine (marketed as CLOZARIL), ziprasidone (marketed as GEODON) and olanzapine/fluoxetine (marketed as SYMBYAX).

Such conjoint treatment may be achieved by way of the simultaneous, sequential or separate dosing of the individual components of the treatment. Such combination products employ the compounds of the invention.

Additional conventional chemotherapy may include one or more of the following categories of agents: (i) antidepressants, (ii) atypical antipsychotics, (iii) antipsychotics, (iv) anxiolytics, (v) anticonvulsants, (vi) currently used Alzheimer's therapies, (vii) Parkinson's therapies, (viii) migraine therapies, (ix) stroke therapies, (x) urinary incontinence therapies, (xi) neuropathic pain therapies, (xii) nociceptive pain therapies, (xiii) insomnia therapies and (xiv) mood stabilizers. Known treatments for the foregoing therapies may be employed in combination with the invention described herein.

Such combination products employ the compounds of this invention within the dosage range described herein and the other pharmaceutically active compound or compounds within approved dosage ranges and/or the dosage described in the publication reference.

Preparation of Compounds

Compounds of the present invention can be prepared as a free base or a pharmaceutically acceptable salt thereof by the processes described below. Throughout the following description of such processes it is understood that, where appropriate, suitable protecting groups will be added to, and subsequently removed from the various reactants and intermediates in a manner that will be readily understood by one skilled in the art of organic synthesis. Conventional procedures for using such protecting groups as well as examples of suitable protecting groups are for example described in *Protective Groups in Organic Synthesis* by T. W. Greene, P. G. M Wutz, 3$^{rd}$ Edition, Wiley-Interscience, New York, 1999. It is understood that MWs (MW) can alternatively be used for the heating of reaction mixtures.

General Methods

All solvents used were of analytical grade and commercially available anhydrous solvents were routinely used for reactions. Starting materials used were available from commercial sources, or prepared according to literature procedures. Room temperature refers to 20-25° C. Solvent mixture compositions are given as volume percentages or volume ratios.

MW heating was performed in a Biotage Creator, Initiator or Smith Synthesizer Single-mode MW cavity producing continuous irradiation at 2450 MHz. It is understood that MWs can be used for the heating of reaction mixtures.

Thin layer chromatography (TLC) was performed on Merck TLC-plates (Silica gel 60 $F_{254}$) and spots were UV visualized. Straight phase flash column chromatography ("flash chromatography") was manually performed on Merck Silica gel 60 (0.040-0.063 mm), or automatically using an ISCO Combiflash® Companion™ system using RediSep™ normal-phase flash columns using the solvent system indicated. Phase separation was optionally performed on an Isolute® phase separator.

NMR

NMR spectra were recorded on a 400-600 MHz NMR spectrometer fitted with a probe of suitable configuration. Spectra were recorded at ambient temperature unless otherwise stated. Chemical shifts are given in ppm down- and upfield from TMS (0.00 ppm). The following reference signals were used in $^1$H-NMR: TMS δ 0.00, or the residual solvent signal of DMSO-$d_6$ δ 2.49, $CD_3OD$ δ 3.30, acetone-$d_6$ 2.04 or $CDCl_3$ δ 7.25 (unless otherwise indicated). Resonance multiplicities are denoted s, d, t, q, m, br and app for singlet, doublet, triplet, quartet, multiplet, broad and apparent, respectively. In some cases only diagnostic signals are reported.

HPLC, HPLCMS, and LCMS Analyses:

High pressure liquid chromatography (HPLC) was performed on a reversed phase (RP) column. A linear gradient was applied using for example mobile phase A (10 mM $NH_4OAc$ in 5% $CH_3OH$ or 5% $CH_3CN$ (aq.), or 0.1% $NH_3$ (aq.) or 0.1% formic acid (aq.)) and B ($CH_3OH$ or $CH_3CN$). Mass spectrometry (MS) analyses were performed in positive and/or negative ion mode using electrospray ionization (ESI+/−) and/or atmospheric pressure chemical ionization (APCI+/−).

GCFID and GCMS Analyses:

Gas chromatography (GC) was performed on a GC equipped with a mass spectrometer (MS) or a flame ionization detector (FID). The MS ion source was either an electron impact (EI) or a chemical ionization (CI, reactant gas methane). For separation a capillary column was used for example DB-5MS, (J&W Scientific). A linear temperature gradient was applied.

Preparative Chromatography:

Preparative chromatography was run on a Waters Fraction-Lynx system with a Autosampler combined Automated Fraction Collector (Waters 2767), Gradient Pump (Waters 2525), Column Switch (Waters CFO) and PDA (Waters 2996). Column; XBridge® Prep C8 10 μm OBD™ 19×300 mm, with guard column; XTerra® Prep MS C8 10 μm 19×10 mm Cartridge. A gradient of A (95% 0.1 M $NH_4OAc$ in MilliQ water and 5% MeCN) in B (100% MeCN) or a gradient of A (95% 0.1 M $NH_4OAc$ in MilliQ water and 5% MeOH), A (0.2% $NH_3$ in MilliQ water) or A (0.2% formic acid in MilliQ water) in B (100% MeOH) was applied for LC-separation at flow rate 20 ml/min. Preparative chiral chromatography for separation of isomers was run on for example an LaPrep® system using the specified column and mobile phase system.

SFC Analyses:

Supercritical Fluid Chromatography (SFC) was performed on a straight phase column. A isocratic flow was applied using mobile phase A ($CO_2$) and for example mobile phase B (MeOH, EtOH or IPA).

Straight Phase HPLC Analyses:

High pressure liquid chromatography (HPLC) was performed on a straight phase column. A linear gradient or isocratic flow was applied using for example mobile phase A (Heptane) and B (EtOH or IPA).

High-Resolution Mass Spectrometry (HRMS):

For accurate mass measurements HRMS was performed on a Waters Synapt-G2 mass spectrometer equipped with a LockSpray source and connected to an Acquity UPLC system with a PDA detector and an Acquity UPLC BEH C18 column. The measured mass confirmed the elemental composition within 3 ppm.

Abbreviations

ACN acetonitrile aq aqueous

Atm atmospheric pressure

Boc t-butoxycarbonyl

Borax di-sodium tetraborate or sodium borate or sodium tetraborate

Cbz benzyloxycarbonyl

CDI 1,1'-carbonyldiimidazole dba dibenzylideneacetone

DCM dichloromethane

DEA diethylamine

DIBAL-H diisobutylaluminium hydride

DIPEA diisopropylethylamine

DMAP 4-Dimethylaminopyridine

DME 1,2-dimethoxyethane

DMF N,N-dimethyl formamide

DMSO dimethyl sulfoxide dppf 1,1'-bis(diphenylphosphino)ferrocene $Et_2O$ diethyl ether EtOAc ethyl acetate EtOH ethanol eq. or equiv. equivalent h hour(s)

HPLC high performance liquid chromatography

IPA isopropanol

LCMS liquid chromatography mass spectrometry

LiHMDS lithium bis(trimethylsilyl)amide

MeOH methanol min minute(s)

MS mass spectrometry

MW MW(s)

$NH_4OAc$ ammonium acetate

NMR nuclear magnetic resonance ox oxidation

Psi pounds per square inch quant. quantitative

RCM ring closing metathesis r.t. room temperature sat. saturated

SFC supercritical fluid chromatography

TFA trifluoroacetic acid

THF tetrahydrofuran

TLC thin layer chromatography

TMEDA tetramethylethylenediamine

UPLC ultra performance liquid chromatography

2-Me THF 2-methyl tetrahydrofuran

Naming Compounds:

Compounds have been named using CambridgeSoft MedChem ELN v2.2 or ACD/Name, version 10.0, or 10.06, or version 12.01, software from Advanced Chemistry Develop-

INTERMEDIATES

Intermediate 1

2-Oxopropanethioamide

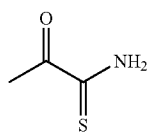

To a −10° C. solution of THF (1700 mL) and acetyl cyanide (250 mL, 3.15 mol) was H$_2$S bubbled for approx 45 min. The bubbling was stopped, and the solution was stirred until the temp. was −10° C. More H$_2$S was bubbled until the temperature was stable at −10° C. Triethylamine (2.2 mL, 15.8 mmol) in THF (20 mL) was added dropwise (very exothermic reaction). at such rate that temp. was kept between 0° C. and −3° C. After addition was completed, the temp. was set to +4° C. and the mixture was stirred overnight. Nitrogen was flushed through the reaction for 30 min and the mixture was concentrated to give the title product (319 g, 98% yield). $^1$H NMR (500 MHz, CDCl$_3$) δ ppm 2.67 (s, 3 H), 7.30-7.81 (m, 1 H), 7.97-8.52 (m, 1 H); $^{13}$C NMR (126 MHz, CDCl$_3$) δ ppm 25.1, 190.8, 192.5; MS (ES+) m/z 104 [M+H]$^+$.

Intermediate 2

6'-Bromospiro[cyclohexane-1,2'-indene]-1',4(3'H)-dione

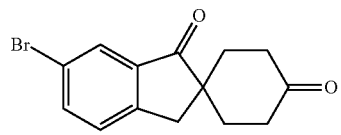 [SMILES: O=C1CCC2(CC1)Cc1ccc(Br)cc1C2=O]

Method A

Potassium tert-butoxide (7.50 g, 66.8 mmol) was added in portions to 6-bromo-2,3-dihydro-1H-inden-1-one (11.8 g, 55.7 mmol) and methyl acrylate (11.1 mL, 123 mmol) in THF (55 mL) under cooling in an ice-bath. The mixture was stirred for 1.5 h at r.t. Water (80 mL) and KOH (3.12 g, 55.7 mmol) was added and the mixture was heated to 75° C. and then at 60° C. overnight. The mixture was cooled to 0° C., and the formed precipitate was filtered off and dried in vacuo to give the title compound (11.69 g, 72% yield). $^1$H NMR (500 MHz, CDCl$_3$) δ ppm 1.83-1.92 (m, 2 H), 2.15-2.27 (m, 2 H), 2.40-2.50 (m, 2 H), 2.71 (dt, 2H), 3.17 (s, 2 H), 7.39 (d, 1 H), 7.75 (dd, 1 H), 7.92 (d, 1 H); MS (ES+) m/z 293 [M+H]$^+$.

Method B

6-Bromo-2,3-dihydro-1H-inden-1-one (800 g, 3.79 mol) and methyl acrylate (787 mL, 8.72 mol) in 2-Me THF (4 L) were stirred at 28° C. Potassium tert-pentoxide solution in toluene (1.7 M, 2.68 L, 4.55 mol) was added dropwise keeping the temperature between 30° C. and 43° C. The mixture was stirred for 0.5 h at 25° C. Water (4 L) was added and after 10 min were KOH (383 g, 6.82 mol) added. The mixture was heated to reflux and the organic solvent was distilled off during 4 h. The mixture was cooled to 10° C., and the formed precipitate was filtered off and dried in vacuo to give the title compound (837 g, 75% yield). $^1$H NMR (500 MHz, DMSO-d$_6$) δ ppm 1.74-1.85 (m, 2 H), 1.94 (m, 2 H), 2.34 (m, 2 H), 2.52-2.60 (m, 2 H), 3.27 (s, 2 H), 7.60 (d, 1 H), 7.79-7.83 (m, 1 H), 7.89 (m, 1 H); MS (ES+) m/z 293 [M+H]$^+$.

Method C

Methyl acrylate (6.6 L, 73 mol) was charged gradually in three equal portions (each 2.2 L, 24.6 mol) to a mixture of 6-bromo-1-indanone (8.00 kg, 37.9 mol), THF (16 L) and potassium tert-butoxide (210 g, 1.87 mol) at about 20-30° C. Additional potassium tert-butoxide (86 g, 0.77 mol), dissolved in THF (0.39 L), was charged after the first portion of methyl acrylate. More potassium tert-butoxide (86 g, 0.77 mol), dissolved in THF (0.39 L), was charged after the second portion of methyl acrylate. Further potassium tert-butoxide (4.64 kg, 41.3 mol) solution in THF (21 L) was then charged gradually at about 20-30° C. Solvent (21.5 L) was distilled off at about 65° C. and then a mixture of water (49 L) and 50%. aq KOH (2.3 L, 30 mol) was added over about 10 min. at below 60° C. The reaction was held at 60° C. for about 6 h., then cooled to 20° C. over 1 h. and then filtered after holding at 20° C. for about 12 h. The solids were washed with a mixture of water (8 L) and THF (4 L), and then dried to give the title compound (7.47 kg, at 92% w/w NMR assay, 23.4 mol, 62% yield): $^1$H NMR (500 MHz, DMSO-d$_6$) δ ppm 1.78-1.84 (m, 2 H), 1.95 (td, 2 H), 2.32-2.38 (m, 2 H), 2.51-2.59 (m, 2 H), 3.27 (s, 2 H), 7.60 (d, 1 H), 7.81 (m, 1 H), 7.89 (m, 1 H).

Intermediate 3

6'-Bromo-4-hydroxyspiro[cyclohexane-1,2'-inden]-1'(3'H)-one

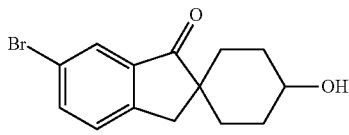 [SMILES: O=C1c2cc(Br)ccc2CC12CCC(O)CC2]

Method A

6'-Bromospiro[cyclohexane-1,2'-indene]-1',4(3'H)-dione (Intermediate 2, 6.1 g, 20.8 mmol) was dissolved in THF (220 mL) and cooled to −65° C. Sodium borohydride (0.354 g, 9.36 mmol) was added and the cooling bath was removed. The mixture was allowed to reach 0° C. (approx. 30 min). Water (10 mL) was added, and most of the organic solvent was removed by evaporation. The residue was partitioned between EtOAc (100 mL), and an aq. solution of NaCl (50 mL). The organic phase was dried (MgSO$_4$) and evaporated to give a product which was combined with additional product obtained in a similar way starting from 14.6 g of 6'-bromo-spiro[cyclohexane-1,2'-indene]-1',4(3'H)-dione. Purification was made by flash chromatography (120 g silica, gradient elution: CH$_2$Cl$_2$ to CH$_2$Cl$_2$/MeOH (90:10)) affording 13.6 g (66% yield) of the title compound. The obtained material consisted of an 80:20 mixture of isomer 1 and isomer 2. Analytical samples of the isomers were isolated by flash chromatography (heptane/EtOAc gradient) to yield:

Isomer 1: (1r,4r)-6'-Bromo-4-hydroxyspiro[cyclohexane-1,2'-inden]-1'(3'H)-one

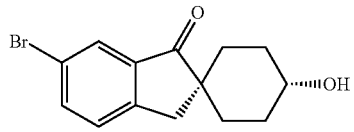 [SMILES: O=C1c2cc(Br)ccc2C[C@]12CC[C@@H](O)CC2]

$^1$H NMR (400 MHz, DMSO-d$_6$) δ ppm 1.20-1.43 (m, 4 H), 1.49-1.62 (m, 2 H), 1.79-1.89 (m, 2 H), 2.99 (s, 2 H), 3.39-3.50 (m, 1 H), 4.68 (d, 1 H), 7.56 (d, 1 H), 7.76 (d, 1 H), 7.85 (dd, 1 H); MS (ES+) m/z 317 [M+Na]$^+$ and Isomer 2: (1s,4s)-6'-bromo-4-hydroxyspiro[cyclohexane-1,2'-inden]-1'(3'H)-one

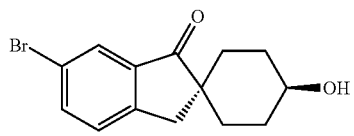 [SMILES: O=C1c2cc(Br)ccc2C[C@]12CC[C@H](O)CC2]

$^1$H NMR (400 MHz, DMSO-d$_6$) δ ppm 1.07-1.20 (m, 2 H), 1.51-1.63 (m, 2 H), 1.65-1.76 (m, 2 H), 1.93 (td, 2 H), 2.98 (s, 2 H), 3.83 (d, 1 H), 4.45 (d, 1 H), 7.51-7.55 (m, 1 H), 7.76 (d, 1 H), 7.84 (dd, 1 H); MS (ES+) m/z 317 [M+Na]$^+$.

Intermediate 3, Isomer 1

Method B

To 6'-bromospiro[cyclohexane-1,2'-indene]-1',4(3'H)-dione (Intermediate 2, 50.5 g, 172 mmol) in DCM (250 mL), borane tert-butylamine complex (5.70 g, 65.5 mmol) in DCM (50 mL) was slowly charged at 0° C. After 40 min concentrated HCl (20 mL) followed by 20% NaCl (70 mL) were charged. The mixture was allowed to reach r.t. and was stirred for 30 min. The phases were separated and to the water phase were DCM (40 mL) and H$_2$O (10 mL) charged. The organic phases were combined, concentrated and dried under vacuum overnight to give the title product (52.4 g, 100% yield) as a mixture of the title product (83% yield) and the other diastereomer (1s,4s)-6'-bromo-4-hydroxyspiro[cyclohexane-1,2'-inden]-1'(3'H)-one (17%): $^1$H NMR (500 MHz, CDCl$_3$, signals for both isomers) δ ppm $^1$H NMR (500 MHz, CDCl$_3$) δ ppm 1.39-1.50 (m, 3 H), 1.67-1.85 (m, 3 H) 2.05-2.12 (m, 2 H) 2.96 (s, 0.34 H), 2.98 (s, 1.68 H), 3.76 (m, 0.83 H), 4.04 (m, 0.17 H), 7.34 (m, 1 H) 7.70 (m, 1 H) 7.88 (d, 1 H); MS (ES+) m/z 295 [M+H]$^+$.

Intermediate 3, Isomer 1

Method C

6'-Bromospiro[cyclohexane-1,2'-indene]-1',4(3'H)-dione (Intermediate 2, 750 g, 2.56 mol) and propan-2-ol (9.855 L) were heated to reflux and ground NaOH (100 g, 2.50 mol) was added in two portions to the mixture. The mixture was heated to reflux for 2 h. 5 L of solvent were removed by vacuum distillation. Toluene (2 L) was added and 2 L of solvent was removed by vacuum distillation. Toluene (3 L) followed by 2 M HCl (1.278 L, 2.56 mol) was added to the mixture under stirring. The phases were separated and the organic phase was washed with water (2.0 L). The organic phase was concentrated and toluene (2 L) was added and then the mixture was concentrated. 2-MeTHF (1 L) was added and then 0.5 L of the solvent was removed by vacuum distillation, the resulting mixture was used in the next step. The title compound was a mixture with the diastereomer (1s,4s)-6'-bromo-4-hydroxyspiro[cyclohexane-1,2'-inden]-1'(3'H)-one in the ratio 7:3 (established by HPLC and NMR analysis): $^1$H NMR (500 MHz, CDCl$_3$, signals for both isomers) δ ppm 1.40-1.52 (m, 3 H), 1.70-1.84 (m, 3 H), 2.04-2.11 (m, 2 H), 2.97 (s, 0.62 H), 3.00 (s, 1.38 H), 3.73-3.81 (m, 0.7 H), 4.04 (m, 0.3 H), 7.31-7.38 (m, 1 H), 7.67-7.73 (m, 1 H), 7.89 (m, 1 H).

Intermediate 4

6'-Bromo-4-methoxyspiro[cyclohexane-1,2'-inden]-1'(3'H)-one

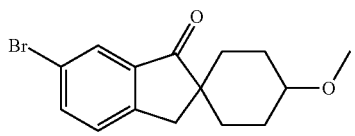 [SMILES: COC1CCC2(CC1)Cc1ccc(Br)cc1C2=O]

Method A

A mixture of isomers of 6'-bromo-4-hydroxyspiro[cyclohexane-1,2'-inden]-1'(3'H)-one (Intermediate 3, 12.7 g, 43.0 mmol) was dissolved in THF (210 mL) under N$_2$ and cooled to 0° C. Potassium tert-butoxide (5.79 g, 51.6 mmol) was added portionwise and the mixture was stirred at 0° C. for 25 min. Methyl iodide (4.30 mL, 68.8 mmol) was added. The cooling bath was removed, and the mixture was stirred at r.t. Additional potassium tert-butoxide (0.483 g, 4.30 mmol) was added twice, after 2 h and 3 h respectively, and then the mixture was stirred for 2 h. Water (100 mL) was added and the resulting solution was partitioned between aq. NaCl solution (200 mL), and EtOAc (200 mL). The aq. phase was extracted with another portion of EtOAc (100 mL). The combined organic phases were dried (MgSO$_4$) and evaporated to give 12.5 g (94% yield) of a mixture (approx. 80:20) of:

Isomer 1: (1r,4r)-6'-bromo-4-methoxyspiro[cyclohexane-1,2'-inden]-1'(3'H)-one

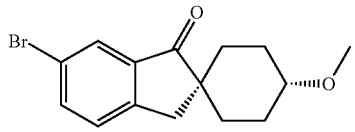

and Isomer 2: (1s,4s)-6'-bromo-4-methoxyspiro[cyclohexane-1,2'-inden]-1'(3'H)-one

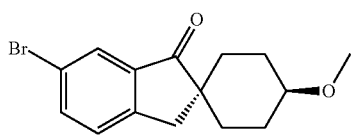 [SMILES: CO[C@H]1CC[C@@]2(CC1)Cc1ccc(Br)cc1C2=O]

$^1$H NMR (400 MHz, DMSO-d$_6$, signals for Isomer 1) δ ppm 1.20-1.32 (m, 2 H), 1.40-1.48 (m, 2 H), 1.51-1.62 (m, 2 H), 1.97-2.07 (m, 2 H), 3.00 (s, 2 H), 3.15-3.23 (m, 1 H), 3.26 (s, 3 H), 7.56 (d, 1 H), 7.77 (d, 1 H), 7.86 (dd, 1 H); MS (ES+) m/z 309 [M+H]$^+$.

Intermediate 4, Isomer 1

Method B (1r,4r)-6'-Bromo-4-hydroxyspiro[cyclohexane-1,2'-inden]-1'(3'H)-one (Intermediate 3, isomer 1, 50.9 g, 172 mmol) (containing 17% of (1s,4s)-6'-bromo-4-hydroxyspiro[cyclohexane-1,2'-inden]-1'(3'H)-one), methyl iodide (18.3 mL, 293 mmol) and 2-Me THF (360 mL) were heated to 30° C. under $N_2$. Potassium tert-pentoxide solution in toluene (1.7 M in toluene, 203 mL, 344 mmol) was added dropwise over 30 min. The mixture was allowed to reach r.t. and was stirred for 1 h. Water (250 mL) was added and after 10 min of stirring the phases were separated. The organic phase was washed with water (140 mL), concentrated and dried in vacuo to give a solid. 300 ml MeOH was added to the solid and the mixture was heated to reflux. Water was added (30 mL) followed by reflux for 5 min. The mixture was slowly allowed to reach r.t. The mixture was stirred overnight at r.t. The solid was filtered off to give the title compound as a single isomer (31 g, 58% yield): $^1$H NMR (500 MHz, CDCl$_3$) δ ppm 1.38 (m, 2 H) 1.52 (m, 2 H) 1.77 (td, 2 H) 2.16 (m, 2 H) 2.98 (s, 2 H) 3.28 (m, 1 H) 3.40 (s, 3 H) 7.35 (d, 1 H) 7.70 (dd, 1 H) 7.88 (d, 1 H); MS (ES+) m/z 309 [M+H]$^+$.

Intermediate 4, Isomer 1

Method C

Borane tert-butylamine complex (820 g, 9.4 mol) dissolved in DCM (3.6 L) was charged to a slurry of 6'-bromospiro[cyclohexane-1,2'-inden]-1',4(3'H)-dione (Intermediate 2, 7.46 kg, at 92% w/w NMR assay, 23.4 mol) in DCM (41 L) at about 0-5° C. over about 40 min. After about 1 h., a solution of NaCl (2.68 kg), water (12.9 L) and 37% hydrochloric acid (2.5 L, 31 mol) was charged. The mixture was warmed to about 15° C. and the phases separated after settling into layers. The DCM phase, containing (1r,4r)-6'-Bromo-4-hydroxyspiro[cyclohexane-1,2'-inden]-1'(3'H)-one (Intermediate 3, isomer 1), was returned to the reactor, together with methyl methanesulfonate (2.59 L, 30.5 mol) and tetrabutylammonium chloride (130 g, 0.47 mol). Aq. 50% NaOH (13 L, 229 mol) was then charged to the vigorously agitated reaction mixture over about 1 h. at about 20° C. After holding for about 16 h., water (19 L) was added and the aq. phase discarded after separation. Solvent (34 L) was distilled off at atmospheric pressure and then more solvent (20 L) was distilled off whilst adding EtOH (20 L) in 5 equal portions. EtOH (14 L) was added and the solution cooled to 25° C. A sample (0.3 L) was taken at 40° C. during the cooling. The sample crystallised spontaneously and was recharged to the reactor at 25° C. After re-heating to about 40° C., water (14 L) was charged over about 20 min. The slurry was cooled to about 20° C. and held for 16 h. before filtering. The solids were washed with a mixture of water (4.8 L) and EtOH (6.4 L) and then dried to give the title compound (containing 4.6% of Isomer 2: (1s,4s)-6'-bromo-4-methoxyspiro[cyclohexane-1,2'-inden]-1'(3'H)-one by HPLC-analysis) (5.57 kg, at 91% NMR assay, 16.4 mol, 70% yield): $^1$H NMR (500 MHz, DMSO-d$_6$) δ ppm 1.22-1.32 (m, 2 H), 1.41-1.48 (m, 2 H), 1.56 (td, 2 H), 1.99-2.07 (m, 2 H), 3.01 (s, 2 H), 3.16-3.23 (m, 1 H), 3.27 (s, 3 H), 7.56 (d, 1 H), 7.77 (d, 1 H), 7.86 (dd, 1 H).

Intermediate 5

(N-(5'-Bromo-4-methoxyspiro[cyclohexane-1,2'-indene]-3'(1'H)-ylidene)-2-methylpropane-2-sulfinamide)

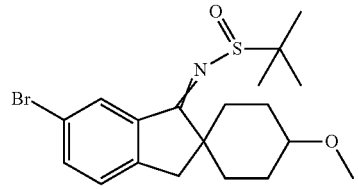 [SMILES: COC1CCC2(CC1)Cc1ccc(Br)cc1C2=NS(=O)C(C)(C)C]

Method A

6'-Bromo-4-methoxyspiro[cyclohexane-1,2'-inden]-1'(3'H)-one (Intermediate 4, mixture of isomers, 1.14 g, 3.69 mmol), 2-methylpropane-2-sulfinamide (0.670 g, 5.53 mmol) and titanium ethoxide (1.519 mL, 7.37 mmol) were dissolved in 2-Me THF (8 mL) and heated to reflux for 26 h. The reaction was left to cool to r.t. EtOAc (80 mL) and NaHCO$_3$ (sat, 15 mL) was added under stirring. The mixture was then standing without stirring for 15 min. The organic phase was collected by filtration, dried over MgSO$_4$ and concentrated. Flash chromatography with a gradient of 0-20% EtOAc in n-heptane gave the title compound (1.00 g, 66% yield). $^1$H NMR (500 MHz, CD$_3$CN, signals for the major isomer) δ ppm 0.85-0.91 (m, 1 H), 1.27 (s, 9 H), 1.25-1.86 (multiplets, 5 H), 2.01-2.10 (m, 2 H), 3.02 (br. s, 2 H), 3.18-3.26 (m, 1 H), 3.31 (s, 3 H), 7.37 (d, 1 H), 7.67 (dd, 1 H), 8.59 (br. s., 1 H), MS (ES+) m/z 413 [M+H]$^+$.

Intermediate 5, Isomer 1

N-((1r,4r)-5'-Bromo-4-methoxyspiro[cyclohexane-1,2'-indene]-3'(1'H)-ylidene)-2-methylpropane-2-sulfinamide

Method B

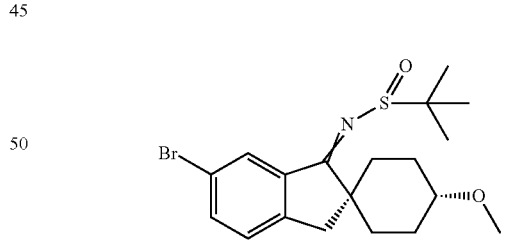

(1r,4r)-6'-Bromo-4-methoxyspiro[cyclohexane-1,2'-inden]-1'(3'H)-one (Intermediate 4, isomer 1, method B, 31 g, 100 mmol), 2-methylpropane-2-sulfinamide (15.8 g, 130 mmol), 2-Me THF (200 mL) and titanium ethoxide (41.3 mL, 200 mmol) were heated to 100° C. to give an azeotrope at 74° C. The azeotropic distillation was continued for 8 h and then the mixture was reflux overnight. The azeotropic distillation was continued for an additional 8 h and then the mixture was refluxed overnight. The mixture was cooled to r.t. Additional 2-Me THF was added to give the original concentration of the mixture. A solution of sulfuric acid (11.14 mL, 200.5 mmol) and Na$_2$SO$_4$ (35.6 g, 250 mmol) in water (150 mL) was prepared. The reaction mixture was then added over 20 min to ⅘ of the volume of the acidic solution. The phases were separated, and the organic phase was washed with the remaining acidic solution, followed by ammonium acetate (15.46 g, 200.5 mmol) in water (75 mL) and water (75 mL). The organic phase was concentrated and dried in vacuo overnight to give the title compound (40.8 g, 99% yield): MS (ES+) m/z 412 [M+H]⁺.

Intermediate 6

6'-Bromo-4-methoxyspiro[cyclohexane-1,2'-inden]-1'(3'H)-imine

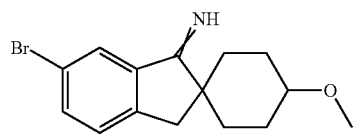 [SMILES: COC1CCC2(CC1)Cc1ccc(Br)cc1C2=N]

Method A

To a solution of N-(5'-bromo-4-methoxyspiro[cyclohexane-1,2'-indene]-3'(1'H)-ylidene)-2-methylpropane-2-sulfinamide (Intermediate 5, mixture of isomers, 2 g, 4.85 mmol) in anhydrous 1,4-dioxane (25 mL) was added 4M HCl in 1,4-dioxane (12.12 mL, 48.50 mmol). A white precipitate was formed immediately and the resulting cloudy mixture was stirred under a nitrogen atmosphere at r.t. for 90 min. Et₂O (30 mL) was added and the solid was filtered off and washed with Et₂O. The solid was partitioned between DCM (40 mL) and sat. aq. NaHCO₃ (40 mL). The phases were separated and the organic layer concentrated. The title compound (1.41 g) was used directly in the next step. MS (EI) m/z 307 M⁺.
Method B Intermediate 6, Isomer 1

(1r,4r)-6'-Bromo-4-methoxyspiro[cyclohexane-1,2'-inden]-1'(3'H)-imine hydrochloride

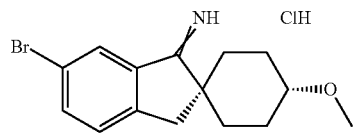 [SMILES: Cl ; CO[C@H]1CC[C@]2(CC1)Cc1ccc(Br)cc1C2=N]

HCl (2 M in Et₂O, 99 mL, 197 mmol) was added dropwise over 5 min to N-((1r,4r)-5'-bromo-4-methoxyspiro[cyclohexane-1,2'-indene]-3'(1'H)-ylidene)-2-methylpropane-2-sulfinamide (Intermediate 5, isomer 1, 40.8 g, 98.9 mmol) dissolved in Et₂O (30 mL) and DCM (30 mL). The mixture was stirred for 60 min before it was filtered. The filter cake was washed with Et₂O and dried in vacuo to give the title compound (31.3 g, 92% yield): ¹H NMR (500 MHz, DMSO-d₆) δ ppm 1.28 (m, 2 H) 1.70 (d, 2 H) 2.04 (m, 4 H) 3.17 (s, 2 H) 3.23 (m, 1 H) 3.28 (s, 3 H) 7.61 (d, 1 H) 8.04 (dd, 1 H) 8.81 (s, 1 H); MS (EI) m/z 307 M⁺.
Method C
Intermediate 6, Isomer 1
(1r,4r)-6'-Bromo-4-methoxyspiro[cyclohexane-1,2'-inden]-1'(3'H)-one (Intermediate 5, isomer 1, 19.20 g at 91% NMR assay, 56.5 mmol) is reacted with 2-methylpropane-2-sulfinamide (8.90 g, 73.5 mmol) by heating with titanium (IV) ethoxide (24 mL, 115 mmol) and 2-Me THF (44 mL) at about 82° C. Three portions of solvent (about 26 mL per portion) were distilled off after 0.5 h, 7.5 h and 8 h periods of heating respectively, and more 2-Me THF (26 mL per portion, three portions) added after completing each distillation. A further portion of solvent (about 26 mL) was distilled off after 17.5 h. The reaction mixture was cooled to r.t., diluted with DCM (52.5 mL) and then added gradually to a solution (92 mL, 113 g) prepared from Na₂SO₄ (17.9% w/w), water (72.2% w/w) and sulfuric acid (9.9% w/w) over about 4 min. DCM (52.5 mL) was used to wash the reaction flask and addition funnel and then added to the work-up flask. After separating the layers, the organic phase was washed with a mixture of water (17.5 mL) and a solution (18.5 mL, 23 g) prepared from Na₂SO₄ (17.9% w/w), water (72.2% w/w) and sulfuric acid (9.9% w/w). The mixture was stirred with Na₂SO₄ (8.75 g) for about 6 h. The slurry was filtered and the filter cake washed with DCM (17.5 mL). The combined filtrates were concentrated by distilling off the solvent (about 108 mL). Further DCM (52.5 mL) was added and the same volume of solvent (52.5 mL) was distilled off. The dry solution was cooled to about 20° C. and diluted with DCM (17.5 mL) and EtOH (8.7 mL). HCl (2 M in Et₂O) (34 mL, 68 mmol), was then added gradually over about 20 min. The resulting slurry was held at about 20° C. for about 45 min before filtering. The filter cake was washed with a solution (17.5 mL per portion, three portions) prepared from equal volumes of DCM and Et₂O and then dried in vacuo to give the title compound containing about 4% of another isomer (17.41 g at 88% w/w NMR assay, 44.4 mmol, 79% yield) (residual DCM was detected at 6.8% w/w and ammonium chloride 2.9% w/w in the NMR assay): ¹H NMR (500 MHz, DMSO-d₆) δ ppm 1.30 (m, 2 H), 1.70 (d, 2 H), 1.98 (m, 2 H), 2.10 (m, 2 H), 3.17 (s, 2 H), 3.23 (m, 1 H), 3.29 (s, 3 H), 7.61 (d, 1 H), 8.04 (dd, 1 H), 8.75 (d, 1 H), 12.90 (br s, 2 H).

Intermediate 7

6'-Bromo-4-methoxy-5"-methyl-3'H-dispiro[cyclohexane-1,2'-indene-1',2"-imidazole]-4"(3"H)-thione

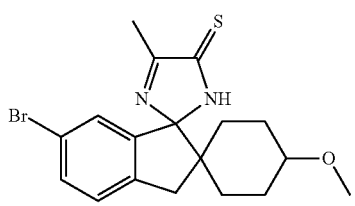 [SMILES: COC1CCC2(CC1)Cc1ccc(Br)cc1C21N=C(C)C(=S)N1]

Method A
6'-Bromo-4-methoxyspiro[cyclohexane-1,2'-inden]-1'(3'H)-imine (Intermediate 6, 1.41 g, 4.57 mmol) and 2-oxopropanethioamide (Intermediate 2, 1.42 g, 13.7 mmol) were dissolved in dry MeOH (30 mL) and the resulting solution was heated at 60° C. under an atmosphere of nitrogen. After 15 h the reaction was allowed to cool to r.t. A precipitate had formed which was filtered off and dried in vacuo, yielding the title compound (1.16 g, 64% yield) as a mixture of isomers. ¹H NMR (500 MHz, DMSO-d₆) δ ppm 1.18 (m, 4 H), 1.47 (m, 2 H), 1.87 (m, 2 H), 2.27 (m, 3 H), 3.03 (m, 3 H), 3.20 (s, 3 H), 6.98 (d, 1 H), 7.34 (d, 1 H), 7.51 (dd, 1 H); MS (APCI+) m/z 394 [M+H]⁺.

Method B

Intermediate 7, Isomer 1

(1r,4r)-6'-Bromo-4-methoxy-5"-methyl-3'H-dispiro[cyclohexane-1,2'-inden-1',2"-imidazole]-4"(3"H)-thione

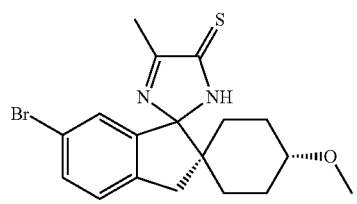

(1r,4r)-6'-Bromo-4-methoxyspiro[cyclohexane-1,2'-inden]-1'(3'H)-imine hydrochloride (Intermediate 6, isomer 1, 95 g, 200 mmol) (containing 30% (1s,4s)-6'-bromo-4-methoxyspiro[cyclohexane-1,2'-inden]-1'(3'H)-imine hydrochloride) was partitioned between DCM (600 mL) and 2 M aq. NaOH (400 mL). The organic phase was concentrated and 2-propanol (200 mL) was added and the mixture was concentrated. The resulting (1r,4r)-6'-bromo-4-methoxyspiro[cyclohexane-1,2'-inden]-1'(3'H)-imine, trimethyl orthoformate (66 mL, 602 mmol) and 2-propanol (300 mL) was heated to 80° C. 2-oxopropanethioamide (51.5 g, 500 mmol) in 2-propanol (250 mL) was added during 40 min while keeping the temperature above 65° C. The reaction was stirred at 75° C. for 2 h. The mixture was concentrated to ½ the volume and was left at 0° C. overnight. A solid that formed was filtered off, and dried in a vacuum cabinet at 40° C. for 3 h to give the title compound (61.24 g, 78% yield, containing 14% of (1s,4s)-6'-bromo-4-methoxy-5"-methyl-3'H-dispiro[cyclohexane-1,2'-inden-1',2'-imidazole]-4"(3"H)-thione): MS (EI) m/z 392 M$^+$.

Intermediate 8

6'-Bromo-4-methoxy-5"-methyl-3'H-dispiro[cyclohexane-1,2'-indene-1',2"-imidazol]-4"-amine

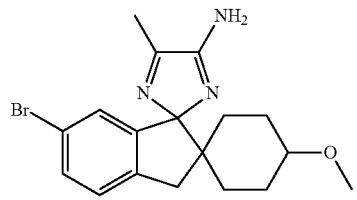 [SMILES: COC1CCC2(CC1)Cc1ccc(Br)cc1C21N=C(C)C(N)=N1]

Method A

6'-Bromo-4-methoxy-5"-methyl-3'H-dispiro[cyclohexane-1,2'-indene-1',2"-imidazole]-4"(3"H)-thione (Intermediate 7, 0.936 g, 2.38 mmol) was taken up in ammonia (7M in MeOH, 10 mL, 70.00 mmol) and the resulting mixture was bubbled with argon and then heated in the MW reactor at 120° C. for 1 h. The solvent was evaporated. Ammonia (7M in MeOH, 6 mL, 42 mmol) was added and the reaction was bubbled with argon and heated again using MW for 60 min at 120° C. The solvent was evaporated and ammonia (7M in MeOH, 10 mL, 70 mmol) was added. The reaction was bubbled with argon and then heated using MW for 2 h at 120° C. The solvent was evaporated and ammonia (7M in MeOH, 15 mL, 105 mmol) was added and the reaction was heated again for 2 h at 120° C. The solvent was evaporated and ammonia (7M in MeOH, 15 mL, 105 mmol) was added and the reaction was heated again for 2 h at 120° C. The solvent was evaporated and ammonia (7M in MeOH, 20 mL, 140 mmol) was added. The reaction was heated again using MW for 1 h at 120° C. The solvent was evaporated and the resulting residue was taken up in DCM (60 mL) and brine (×2) and poured into a phase separator. The organic phase was dried with MgSO$_4$, filtered and evaporated to give the title compound (0.736 g, 82% yield) as a mixture of isomers: $^1$H NMR (500 MHz, CDCl$_3$) δ ppm 1.09 (td, 1 H), 1.27-1.49 (m, 3 H), 1.62-1.74 (m, 2 H), 1.93-2.01 (m, 2 H), 2.37 (s, 3 H), 3.04-3.18 (m, 3 H), 3.34 (s, 3 H), 6.90 (d, 1 H), 7.20 (d, 1 H), 7.38 (dd, 1 H); MS (MM-ES+APCI)+ m/z 376 [M+H]$^+$.

Separation of the isomers of 6'-bromo-4-methoxy-5"-methyl-3'H-dispiro[cyclohexane-1,2'-indene-1',2"-imidazol]-4"-amine 6'-Bromo-4-methoxy-5"-methyl-3'H-dispiro[cyclohexane-1,2'-indene-1',2"-imidazol]-4"-amine (Intermediate 8, 80 mg, 0.21 mmol) was purified using preparative chromatography (Waters FractionLynx system equipped with a XBridge® Prep C8 10 µm OBD™ 19×250 mm column and a guard column; XTerra® Prep MS C8 10 µm 19×10 mm Cartridge. A linear gradient of 35-70% MeOH in 0.2% NH$_3$ in MifliQ water was applied at flow rate of 20 mL/min) to give: Isomeric mixture 1: (1s,4s)-6'-Bromo-4-methoxy-5"-methyl-3'H-dispiro[cyclohexane-1,2'-indene-1',2"-imidazol]-4"-amine (the first to elute, minor isomer, 2.0 mg, 2.5% yield):

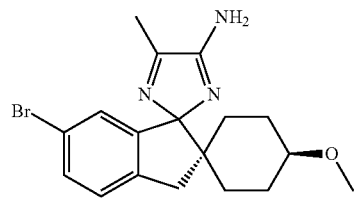

$^1$H NMR (500 MHz, CD$_3$CN) δ ppm 1.15-1.25 (m, 2 H), 1.36 (td, 1 H), 1.45-1.59 (m, 2 H), 1.63-1.74 (m, 3 H), 2.19 (s, 3H), 2.98-3.06 (dd, 2 H), 3.20 (s, 3 H), 3.32 (t, 1 H), 5.19-5.39 (m, 2 H), 6.75 (d, 1 H), 7.20 (d, 1 H), 7.34 (dd, 1 H); MS (ES+) m/z 378 [M+H]$^+$.

and Isomeric mixture 2: (1r,4r)-6'-Bromo-4-methoxy-5"-methyl-3'H-dispiro[cyclohexane-1,2'-indene-1',2"-imidazol]-4"-amine (the second to elute, major isomer, yield not determined):

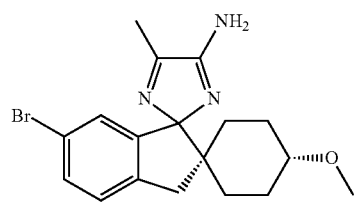

$^1$H NMR (500 MHz, CDCl$_3$) δ ppm 1.09 (td, 3.47 Hz, 1 H), 1.27-1.49 (m, 3 H), 1.62-1.74 (m, 2 H), 1.93-2.01 (m, 2 H), 2.37 (s, 3 H), 3.04-3.18 (m, 3 H), 3.34 (s, 3 H), 6.90 (d, 1 H), 7.20 (d1 H), 7.38 (dd, 1.73 Hz, 1 H), MS (MM-ES+APCI)+ m/z 378 [M+H]+.

Separation of the isomers of (1r,4r)-6'-bromo-4-methoxy-5''-methyl-3'H-dispiro-[cyclohexane-1,2'-indene-1',2''-imidazol]-4''-amine The isomers of Isomeric mixture 2 of Intermediate 8 were separated using SFC Berger Multigram II, with a LuxC4; 4.6*250 mm; 5 µm column, and a mobile phase consisting of 15% MeOH (containing 0.1% DEA) and 85% $CO_2$ at a flow rate of 50 mL/min to give:
Isomer 1: (1r,1'R,4R)-6'-Bromo-4-methoxy-5''-methyl-3'H-dispiro[cyclohexane-1,2'-indene-1',2''-imidazol]-4''-amine (9 mg, 11% yield) with retention time 6.1 min:

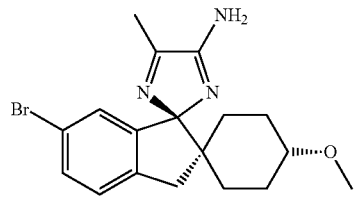

$^1$H NMR (500 MHz, $CD_3CN$) δ ppm 1.05 (dd, 1 H), 1.23 (dt, 2 H), 1.39 (d, 1 H), 1.49 (ddd, 2 H), 1.81-1.89 (m, 2 H), 2.17 (s, 3 H), 2.94-3.10 (m, 3 H), 3.23 (s, 3 H), 5.32 (br. s., 2 H), 6.75 (d, 1 H), 7.19 (d, 1 H), 7.33 (dd, 1 H), MS (MM-ES+APCI)+ m/z 378 [M+H]+;
and Isomer 2: (1r,1'S,4S)-6'-Bromo-4-methoxy-5''-methyl-3'H-dispiro[cyclohexane-1,2'-indene-1',2''-imidazol]-4''-amine (15 mg, 19% yield) with retention time 9.5 min:

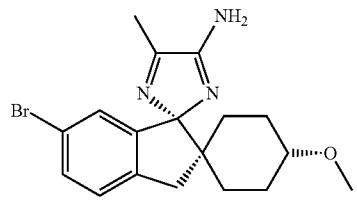

$^1$H NMR (500 MHz, $CD_3CN$) δ ppm 1.00-1.09 (m, 1 H), 1.17-1.31 (m, 2 H), 1.39 (td, 1 H), 1.50 (ddd, 2 H), 1.86 (dt, 2 H), 2.18 (s, 3 H), 2.94-3.10 (m, 3 H), 3.24 (s, 3 H), 5.32 (br. s., 2 H), 6.76 (d, 1 H), 7.20 (d, 1 H), 7.34 (dd, 1 H), MS (MM-ES+APCI)+ m/z 378 [M+H]+.

Separation of the isomers of (1s,4s)-6'-bromo-4-methoxy-5''-methyl-3'H-dispiro-[cyclohexane-1,2'-indene-1',2''-imidazol]-4''-amine 1.7 g of a mixture containing (1r,4r)-6'-bromo-4-methoxy-5''-methyl-3'H-dispiro[cyclohexane-1,2'-indene-1',2''-imidazol]-4''-amine (Intermediate 8, isomeric mixture 2, major) and (1s,4s)-6'-bromo-4-methoxy-5''-methyl-3'H-dispiro[cyclohexane-1,2'-indene-1',2''-imidazol]-4''-amine (Intermediate 8, isomeric mixture 1, minor) was purified by preparative chromatography using the following conditions: Column: XBridge C18; 50*300 mm; 10 µm, Mobile phase: 20-60% MeCN in 0.1% aq. $NH_3$ over 20 min, Flow rate: 120 mL/min. The obtained minor isomer (equivalent to Isomeric mixture 1 above) with retention time 15 min, was then separated into its isomers by preparative SFC using the following system: Berger Multigram II SFC system, Column: Chiralcel OD-H; 20*250 mm; 5 µm, Mobile phase: 10% MeOH (containing 0.1% DEA)/90% $CO_2$, Flow rate: 50 mL/min resulting in:
Isomer 3 with undetermined absolute configuration (77 mg, 5% yield) with retention time 6.5 min: $^1$H NMR (400 MHz, DMSO-$d_6$) δ ppm 1.05-1.17 (m, 2 H), 1.24 (td, 1 H), 1.36-1.54 (m, 2 H), 1.57-1.74 (m, 3 H), 2.16 (s, 3 H), 2.85-3.07 (m, 2 H), 3.12 (s, 3 H), 3.29 (br. s., 1 H), 6.58 (s, 2 H), 6.63 (d, 1 H), 7.24 (d, 1 H), 7.33 (dd, 1 H); MS (APCI+) m/z 376 [M+H]+,
and Isomer 4 with undetermined absolute configuration (64 mg, 4% yield) with retention time 12 min: $^1$H NMR (400 MHz, DMSO-$d_6$) δ ppm 1.05-1.17 (m, 2 H), 1.24 (td, 1 H), 1.36-1.55 (m, 2 H), 1.57-1.74 (m, 3 H), 2.16 (s, 3 H), 2.85-3.06 (m, 2 H), 3.12 (s, 3 H), 3.29 (br. s., 1 H), 6.58 (s, 2 H), 6.63 (d, 1 H), 7.24 (d, 1 H), 7.33 (dd, 1 H); MS (APCI+) m/z 376 [M+H]+.
Method B Intermediate 8, Isomeric Mixture 2

(1r,4r)-6'-Bromo-4-methoxy-5''-methyl-3'H-dispiro [cyclohexane-1,2'-indene-1',2''-imidazol]-4''-amine

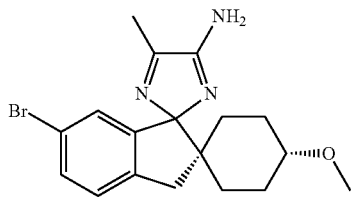

(1r,4r)-6'-Bromo-4-methoxy-5''-methyl-3'H-dispiro[cyclohexane-1,2'-indene-1',2''-imidazole]-4''(3''H)-thione (Intermediate 7, isomer 1, 22.7 g, 57.7 mmol) and ammonia (7 M in MeOH, 180 mL, 1.26 mol) was put in a pressure reactor and heated to 74° C. overnight. The residue was allowed to reach r.t. and the mixture was concentrated. The residue was partitioned between 2 M citric acid (400 mL) and EtOAc (400 mL). Insoluble material was filtered off and was determined to be unreacted starting material. The organic phase (org 1) was concentrated in vacuo to give additional unreacted starting material. To the aqueous phase was EtOAc (300 mL) added and then 50% NaOH was added until pH ~12, and the mixture was stirred for 10 min. The resulting organic phase (org 2) was saved. The residue from org 1, and the solid filtered off were combined and suspended in ammonia (7 M in MeOH, 180 mL, 1.26 mmol) and put in a pressure reactor and heated 100° C. overnight. The obtained solution was concentrated in vacuo. The residue was partitioned between 2 M citric acid (300 mL) and EtOAc (300 mL). To the aqueous phase was EtOAc (300 mL) added and then 50% NaOH was added until pH ~12, and the mixture was stirred for 10 min. The organic phase was combined with org 2 from above. Activated charcoal was added to the organic phase and the mixture was stirred for 30 min before it was filtered through diatomaceous earth. The organic phase was concentrated and dried in vacuo overnight to give a solid. To the solid was diisopropyl ether (125 mL) added and the mixture was refluxed overnight. The mixture was allowed to reach r.t. and the solid was filtered off to give the title compound (equivalent to Intermediate 8, Isomeric Mixture 2 above) (15 g, 69% yield): $^1$H NMR (500 MHz, DMSO-$d_6$) δ ppm 0.93 (m, 1 H)

1.1-1.25 (m, 2 H) 1.35-1.45 (m, 3 H) 1.81 (br. d, 2 H) 2.16 (s, 3H) 2.87-3.03 (m, 3 H) 3.18 (s, 3 H) 6.59 (br. s., 2 H), 6.64 (d, 1 H), 7.25 (d, 1 H), 7.34 (dd, 1 H); ES+) m/z 376 [M+H]⁺.

Intermediate 8, Isomer 1

(1r,1'R,4R)-6'-Bromo-4-methoxy-5"methyl-3'H-dispiro[cyclohexane-1',2"-indene-1',2"imidazol]-4"-amine

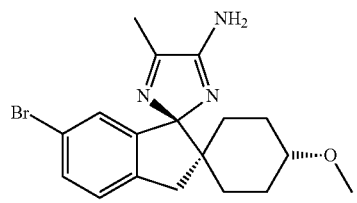

To a 1 L round-bottomed flask was added (1r,4r)-6'-bromo-4-methoxy-5"-methyl-3'H-dispiro[cyclohexane-1,2'-indene-1',2"-imidazol]-4"-amine (Intermediate 8, isomeric mixture 2, Method B, 61 g, 162 mmol), EtOH (99.5%, 600 mL) and water (60 mL) to give a homogeneous mixture which was heated to 70° C. The mixture was stirred for 30 min at the elevated temperature followed by addition of D(+)-10-camphorsulfonic acid (18.8 g, 81.0 mmol). The mixture was stirred at 70° C. for 3 h and then allowed to reach 20° C. over 2 h followed by stirring at 20° C. for 12 h. The mixture was filtered to give a solid that was washed with cold EtOH and then dried in a vacuum oven at 50° C. for 10 h to give the title compound as a D(+)-10-camphorsulfonic salt (37 g; 37% yield). Enantiomeric ratio was determined by analysis on a SFC Berger Analytix system equipped with a Chiralpak AD-H column (4.6*250 mm; 5 μm) and a mobile phase consisting of 10% MeOH (containing 0.1% DEA) and 90% $CO_2$ at a flow rate of 3 mL/min. The first peak with retention time 3.68 min (area 2.5%) corresponded to (1r,1'S,4S)-6'-bromo-4-methoxy-5"-methyl-3'H-dispiro[cyclohexane-1,2'-indene-1',2"-imidazol]-4"-amine, equivalent to Isomer 2. The second peak with retention time 4.58 min (area 97.5%) corresponded to the title compound (1r,1'R,4R)-6'-bromo-4-methoxy-5"methyl-3'H-dispiro[cyclohexane-1',2"-indene-1',2"imidazol]-4"-amine, equivalent to Isomer 1.

The liberation of the title compound from the salt was carried out by stirring the camphorsulfonic acid salt (0.32 g, 0.53 mmol) suspended in dichloromethane (4 mL) with an aqueous solution (4 mL) of KOH (0.32 g, 5.7 mmol) at r.t. during 30 min. The organic phase was separated and concentrated in vacuo to give title compound quantitatively with an enantiomeric excess of 95% (determined as above).
Method C Intermediate 8, Isomer 1 (+)-Camphor Sulfonylate (1r,1'R,4R)-6'-Bromo-4-methoxy-5"methyl-3'H-dispiro[cyclohexane-1',2"-indene-1',2"imidazol]-4"-amine (+)-camphor sulfonylate (1r,4r)-6'-Bromo-4-methoxy-5"-methyl-3'H-dispiro[cyclohexane-1,2'-indene-1',2"-imidazole]-4"(3"H)-thione (Intermediate 7, isomer 1, 12.8 g, 32.6 mmol), ammonia (7 M in MeOH, 93.3 mL, 653 mmol) and zinc acetate dihydrate (8.60 g, 39.2 mmol) were charged to a pressure reactor and heated to 80° C. for 24 h. The reaction mixture was cooled down. and the solvent changed into 1-butanol, final volume 130 mL (1-BuOH (130 mL) was added, then the mixture was distilled down to 130 mL, at which stage distillation was continued while additional 1-BuOH (65 mL) was added to maintain the volume). The organic solution was washed with 1 M aq. sodium hydroxide solution (85 mL) and water (51 mL). The resultant solution was heated to 70° C. and (+)-camphor sulfonic acid (6.82 g, 29.4 mmol) added. The mixture was cooled and the resulting solid collected by filtration, washed with ethanol (51 mL) and dried in a vacuum oven at 40° C. affording the title compound as a white solid (7.09 g, 41% yield) with 99% enantiomeric purity (chromatography: ChiralPak IA-3 0.46 cm×5 cm, column temperature 20° C. with a mobile phase consisting of 95:5 isohexane:ethanol (0.1% v/v triethylamine) at a flow rate of 0.9 mL/min, Intermediate 8, isomer 1: retention time 2.66 min, Intermediate 8, isomer 2 retention time 2.39 min).

Intermediate 9

6-Isobutoxy-2,3-dihydro-1H-inden-1-one

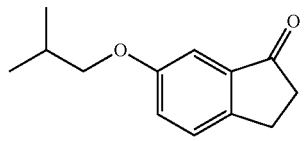

To a mixture of 6-hydroxy-2,3-dihydro-1H-inden-1-one (5.0 g, 33.8 mmol) in DMF (170 mL) was added $K_2CO_3$ (9.33 g, 67.5 mmol) and 1-bromo-2-methylpropane (5.50 mL, 50.6 mmol). The resulting orange mixture was stirred at r.t. overnight and was then heated to 60° C. for 2 days. The mixture was cooled to r.t., water was added and the mixture was extracted with EtOAc (×4). The combined organic layers were dried over $MgSO_4$ and concentrated in vacuo. Purification by flash chromatography using 0-20% EtOAc in heptane as eluent afforded 4.98 g (72% yield) of the title compound: ¹H NMR (500 MHz, $CDCl_3$) δ ppm 1.03 (d, 6 H), 2.10 (dt, 1 H), 2.69-2.75 (m, 2 H), 3.04-3.11 (m, 2 H), 3.75 (d, 2 H), 7.17-7.22 (m, 2 H), 7.37 (d, 1 H); MS (ES+) m/z 205 [M+H]⁺.

Intermediate 10

6'-Isobutoxyspiro[cyclohexane-1,2'-indene]-1',4(3'H)-dione

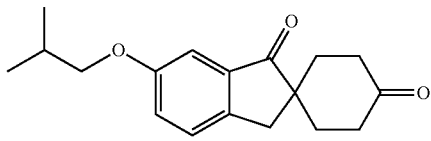 [SMILES: CC(C)COc1ccc2c(c1)C(=O)C1(CCC(=O)CC1)C2]

To a mixture of 6-isobutoxy-2,3-dihydro-1H-inden-1-one (Intermediate 4, 17.4 g, 85 mmol) and methyl acrylate (16.9 mL, 187 mmol) in 2-Me THF (84 mL) cooled to 0° C. was added potassium tert-butoxide (11.8 g, 102 mmol) in portions over 3 min. After stirring at r.t. for 2.5 h more potassium tert-butoxide (2.95 g, 25.5 mmol) was added at 0° C. After stirring at r.t. for 2.5 h were water (126 mL) and potassium hydroxide (4.77 g, 85 mmol) added and the mixture was heated at reflux overnight. The mixture was allowed to cool to r.t. and brine was added. The layers were separated and the aqueous layer was re-extracted with EtOAc twice. The combined organic layers were dried over Na₂SO₄, filtered and evaporated to yield the title compound (13.7 g, 56% yield). $^1$H NMR (400 MHz, CDCl₃) δ ppm 1.04 (m, 8 H) 1.86 (m, 2 H) 2.11 (dt, 1 H) 2.21 (m, 2 H) 2.47 (m, 3 H) 2.70 (m, 2 H) 3.15 (s, 2 H) 3.76 (m, 3 H) 7.20 (m, 1 H) 7.25 (m, 1 H) 7.38 (d, 1 H); MS (ES+) m/z 287 [M+H]⁺.

Intermediate 11

(1r,4r)-4-Hydroxy-6'-isobutoxyspiro[cyclohexane-1, 2'-inden]-1'(3'H)-one

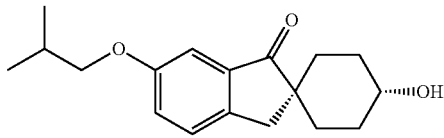 [SMILES: CC(C)COc1ccc2c(c1)C(=O)[C@]1(CC[C@H](O)CC1)C2]

To a solution of 6'-isobutoxyspiro[cyclohexane-1,2'-indene]-1',4(3'H)-dione (Intermediate 10, 25.4 g, 88.7 mmol) in dichloromethane (300 mL), was borane tert-butylamine complex (2.93 g, 33.7 mmol) added at 0° C. After stirring at 0° C. for 1.5 h, conc HCl (10 mL) was added slowly followed by 20% NaCl (70 mL). The mixture was allowed to reach r.t. and was stirred for 30 min. The phases were separated and the aq. phase was extracted with dichloromethane. The combined organic layers were concentrated and the residue purified by flash chromatography with a gradient of 0-50% EtOAc in heptane as eluent to afford the title compound (12.6 g, 49% yield, containing 3% of another isomer) A second sample, (5.9 g, 23% yield, containing 18% of the other isomer) was also obtained. $^1$H NMR (400 MHz, CDCl₃) δ 1.03 (d, J=6.82 Hz, 7 H), 1.38-1.52 (m, 5 H), 1.76-1.87 (m, 2 H), 2.02-2.16 (m, 4 H), 2.97 (s, 2 H), 3.70-3.82 (m, 4 H), 7.17 (d, J=2.53 Hz, 1 H), 7.19-7.24 (m, 1 H), 7.34 (dd, J=8.34, 0.51 Hz, 1 H); MS (ES+) m/z 289 [M+H]⁺.

Intermediate 12

Di-tert-butyl [(1r,4r)-6'-bromo-4-methoxy-5''-methyl-3'H-dispiro[cyclohexane-1,2'-indene-1',2''-imidazol]-4''-yl]imidodicarbonate

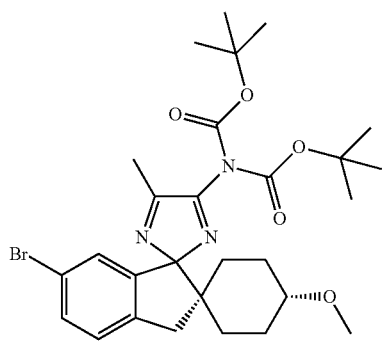

Di-tert-butyl dicarbonate (8.53 g, 39.1 mmol), Et₃N (5.44 mL, 39.1 mmol) and DMAP (0.227 g, 1.86 mmol) were added to a solution of (1r,4r)-6'-bromo-4-methoxy-5''-methyl-3'H-dispiro[cyclohexane-1,2'-indene-1',2''-imidazol]-4''-amine (Intermediate 8, isomeric mixture 2, 7.00 g, 18.6 mmol) in DCM (100 mL). The resulting mixture was stirred at r.t. for 20 h. The reaction mixture was diluted with DCM and washed with 2 M aqueous HCl, water, aq. sat. NaHCO₃ and brine, dried over MgSO₄ and concentrated. Purification by chromatography on silica using gradient elution of 0-5% methanol in DCM gave the title compound (4.41 g, 41% yield). $^1$H NMR (500 MHz, DMSO-d₆) δ ppm 1.1-1.3 (m, 4 H), 1.4 (s, 18 H), 1.5-1.6 (m, 2 H), 1.8-1.9 (m, 2 H), 2.2 (s, 3 H), 2.9-3.0 (m, 1 H), 3.1 (s, 2 H), 3.2 (s, 3 H), 6.7 (d, 1 H), 7.4 (d, 1 H), 7.5 (dd, 1 H). MS (ES+) m/z 576 [M+H]⁺.

Intermediate 13 tert-Butyl [(1r,4r)-6'-bromo-4-methoxy-5''-methyl-3'H-dispiro[cyclohexane-1,2'-indene-1',2''-imidazol]-4''-yl]carbamate

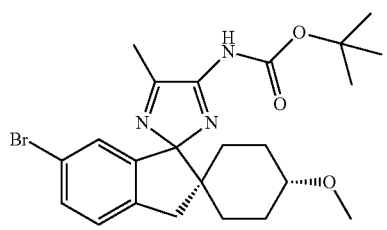

A mixture of di-tert-butyl [(1r,4r)-6'-bromo-4-methoxy-5''-methyl-3'H-dispiro[cyclohexane-1,2'-indene-1',2''-imidazol]-4''-yl]imidodicarbonate and t-butyl [(1r,4r)-6'-bromo-4-methoxy-5''-methyl-3'H-dispiro[cyclohexane-1,2'-indene-1',2''-imidazol]-4''-yl]imidocarbonate (Intermediate 12, used as mixture not subjected to chromatography, 4.09 g, 7.78 mmol) was treated with 2 M aqueous Na₂CO₃ (7.1 mL, 14 mmol) at 40° C. for 8 h. Most of the methanol was evaporated at reduced pressure and the residue was extracted with EtOAc. The combined extracts were washed with brine, dried over MgSO₄ and concentrated. Purification by chromatography on silica using gradient elution of 0-10% MeOH in a mixture of DCM and heptane (15:85) gave a product displaying a $^1$H NMR consistent with a 1:1 mixture of two isomers of the title compound (2.90 g, 86% yield). $^1$H NMR (500 MHz, DMSO-d₆) δ ppm 1.44 (s partially overlapped with multiplet, 9 H), 1.47 (s partially overlapped with multiplet, 9 H), 2.18 (s, 3 H), 2.28 (s, 3 H), 3.18 (s partially overlapped with multiplet, 4 H), 3.20 (s partially overlapped with multiplet, 3 H), 6.66 (d, 1 H), 7.03 (m, 1 H), 7.31 (m, 2 H), 7.41 (dd, 1 H), 7.48 (dd, 1 H), 9.85 (s, 1 H), 10.52 (s, 1 H); MS (ES+) m/z 476 [M+H]⁺.

Intermediate 14

Step 1: N-((1r,4r)-5'-Bromo-4-hydroxyspiro[cyclohexane-1,2'-indene]-3'(1'H)-ylidene)-2-methylpropane-2-sulfinamide

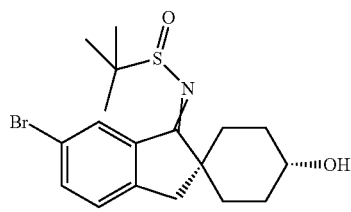 [SMILES: CC(C)(C)S(=O)N=C1c2cc(Br)ccc2C[C@]12CC[C@@H](O)CC2]

Titanium ethoxide (0.733 mL, 3.56 mmol), 2-methyl-2-propanesulfinamide (0.411 g, 3.39 mmol) and (1r,4r)-6'-bromo-4-hydroxyspiro[cyclohexane-1,2'-inden]-1'(3'H)-one (Intermediate 3, Isomer 1) (0.5 g, 1.69 mmol) in dry 2-Me THF (7.5 mL) were refluxed for three days. 2-Methyl-2-propanesulfinamide (0.411 g, 3.39 mmol), titanium ethoxide (0.733 mL, 3.56 mmol) and 2-Me THF (3 mL) were added and the mixture was refluxed for four more days. The cooled mixture was added to a mixture of MeOH (12.5 mL), sat. aq. NaHCO$_3$ (5 mL) and EtOAc (50 mL). The resulting slurry was stirred for 90 min and was then filtered through a mixture of diatomaceous earth and Na$_2$SO$_4$ and then concentrated in vacuo. Purification by flash chromatography using a gradient of CHCl$_3$/MeOH (40:1-30:1-20:1) gave the title compound (0.398 g, 59% yield): $^1$H NMR (500 MHz, DMSO-d$_6$) δ ppm 1.21-1.78 (m, 15 H), 1.83 (m, 2 H), 2.96-3.01 (m, 2 H), 3.44 (m, 1 H), 4.63-4.72 (m, 1 H), 7.50 (d, 1 H), 7.73-7.82 (m, 1 H), 8.51 (br. s., 1 H); MS (ES+) m/z 398 [M+H]$^+$.

Intermediate 15

(1r,4r)-6'-Bromo-4-hydroxy-5"-methyl-3'H-dispiro[cyclohexane-1,2'-indene-1',2"-imidazole]-4"(3"H)-thione

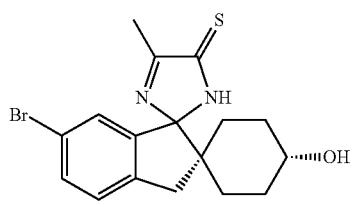

To N-((1r,4r)-5'-bromo-4-hydroxyspiro[cyclohexane-1,2'-indene]-3'(1'H)-ylidene)-2-methylpropane-2-sulfinamide (Intermediate 14, 2.21 g, 5.55 mmol) in dioxane (10 mL) under N$_2$ (g) was added HCl (4 M in 1,4-dioxane, 13.9 mL, 55.5 mmol). The mixture was stirred at r.t for 2 h and then concentrated. DCM and Et$_2$O were added resulting in the formation of a solid. The solid was filtered off and washed with Et$_2$O. The solid was dissolved in DCM. Sat. aq. NaHCO$_3$ was added and the mixture was poured into a phase separator. The organic phase was collected and concentrated. The residue, containing (1r,4r)-6'-bromo-1'-imino-1',3'-dihydrospiro[cyclohexane-1,2'-inden]-4-ol was mixed with 2-oxopropanethioamide (Intermediate 2, 1.55 g, 15.0 mmol) in dry MeOH (25 mL) and heated at 60° C. under N$_2$ (g) overnight. A solid formed and was filtered off. The filtrate was concentrated. Purification by flash chromatography using a gradient of 0-100% EtOAc in n-heptane gave the title compound (1.33 g, 63% yield): $^1$H NMR (400 MHz, DMSO-d$_6$) δ ppm 1.05-1.32 (m, 4 H), 1.43 (m, 2 H), 1.70 m, 2 H), 2.26 (s, 3 H), 2.98 (d, 1 H), 3.06 (d, 1 H), 3.26 (m, 1 H), 4.58 (d, 1 H), 6.97 (d, 1 H), 7.35 (d, 1 H), 7.51 (dd, 1 H), 12.34 (s, 1 H); MS (ES+) m/z 379 [M+H]$^+$.

Intermediate 16

6-(3,3,3-trifluoropropoxy)-2,3-dihydro-1H-inden-1-one

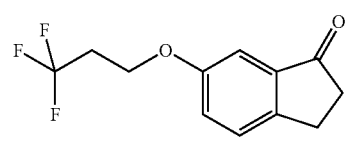 [SMILES: O=C1CCc2ccc(OCCC(F)(F)F)cc21]

To a solution of 6-hydroxy-2,3-dihydro-1H-inden-1-one (3.0 g, 20.3 mmol) in THF (140 mL) were triphenylphosphine (7.97 g, 30.4 mmol) and 3,3,3-trifluoropropan-1-ol (1.96 mL, 22.3 mmol) added. Diisopropyl azodicarboxylate (5.98 mL, 30.4 mmol) was added dropwise and the mixture was left stirring at r.t. overnight. Since there was starting material remaining, 3,3,3-trifluoro-1-propanol (0.892 mL, 10.1 mmol) was added dropwise and stirring was continued. After 30 min the mixture was heated to 40° C. and after 1 h the mixture was concentrated. The product was purified by flash chromatography (0-12% EtOAc in heptane as eluent) to afford 1.08 g (22% yield) of the title compound (containing some diisopropyl azodicarboxylate): $^1$H NMR (500 MHz, CDCl$_3$) δ 2.65 (qt, 2 H), 2.71-2.77 (m, 2 H), 3.05-3.13 (m, 2 H), 4.23 (t, 2 H), 7.17-7.23 (m, 2 H), 7.40 (d, 1 H); MS (ES+) m/z 245 [M+H]$^+$.

Intermediate 17

6'-(3,3,3-Trifluoropropoxy)spiro[cyclohexane-1,2'-indene]-1',4(3'H)-dione

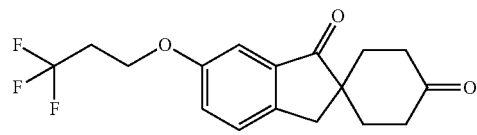 [SMILES: O=C1CCC2(CC1)Cc1ccc(OCCC(F)(F)F)cc1C2=O]

A mixture of 6-(3,3,3-trifluoropropoxy)-2,3-dihydro-1H-inden-1-one (Intermediate 16, 0.774 g, 3.17 mmol) and methyl acrylate (0.629 mL, 6.97 mmol) in 2-Me THF (4 mL) was cooled to 0° C. and potassium tert-butoxide (0.427 g, 3.80 mmol) was added in portions. After stirring for 1.5 h at r.t., water (6.0 mL) and potassium hydroxide (0.178 g, 3.17 mmol) were added and the mixture was heated at reflux overnight. The mixture was cooled to r.t. and water and brine was added. The layers were separated and the aqueous layer extracted with EtOAc. The combined organic layers were dried over MgSO$_4$ and concentrated yielding the title compound (689 mg, 67% yield). $^1$H NMR (500 MHz, CDCl$_3$) δ ppm 1.82-1.92 (m, 2 H), 2.17-2.27 (m, 2 H), 2.42-2.53 (m, 2 H), 2.60-2.75 (m, 4 H), 3.14-3.20 (m, 2 H), 4.22-4.27 (m, 2 H), 7.19-7.22 (m, 1 H), 7.25 (dd, 1 H), 7.41 (d, 1 H): MS (ES+) m/z 327 [M+H]$^+$.

Intermediate 18

(1r,4r)-4-Hydroxy-6'-(3,3,3-trifluoropropoxy)spiro[cyclohexane-1,2'-inden]-1'(3'H)-one

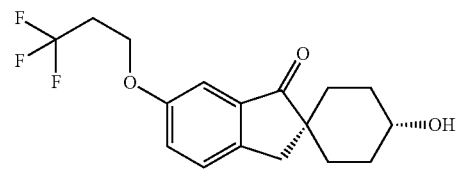 [SMILES: O=C1c2cc(OCCC(F)(F)F)ccc2C[C@]12CC[C@@H](O)CC2]

6'-(3,3,3-trifluoropropoxy)spiro[cyclohexane-1,2'-indene]-1',4(3'H)-dione (Intermediate 17, 0.689 g, 2.11 mmol) was dissolved in THF (10 mL) and MeOH (0.854 mL, 21.1 mmol). Borane-trimethylamine complex (0.339 g, 4.65 mmol) was added and the mixture was stirred at r.t. for 6 h. Citric acid monohydrate (6.21 g, 29.6 mmol) was added all at once and was followed by dropwise addition of water (0.761 mL, 42.2 mmol) and the mixture was stirred overnight before being diluted with water and extracted with EtOAc twice. The combined organic phases were washed with NaHCO$_3$ and brine, dried over Na$_2$SO$_4$ and concentrated. The residue was purified by flash chromatography (0-100% EtOAc in heptane) to afford the title compound (357 mg, 52% containing 16% of another isomer). $^1$H NMR (500 MHz, CDCl$_3$) δ ppm 1.40-1.52 (m, 4 H), 1.82 (td, 2 H), 2.03-2.13 (m, 2 H), 2.65 (qt, 2 H), 2.99 (s, 2 H), 3.73-3.82 (m, 1 H), 4.23 (t, 2 H), 7.16-7.20 (m, 1 H), 7.22 (dd, 1 H), 7.38 (d, 1 H); MS (ES+) m/z 329 [M+H]$^+$.

Intermediate 19

((1r,4r)-4-Methoxy-6'-(3,3,3-trifluoropropoxy)spiro [cyclohexane-1,2'-inden]-1'(3'H)-one

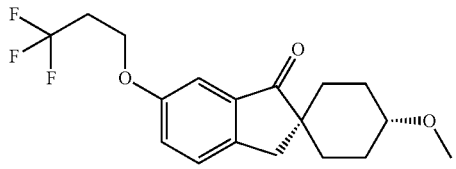 [SMILES: CO[C@H]1CC[C@]2(CC1)Cc1ccc(OCCC(F)(F)F)cc1C2=O]

(1r,4r)-4-Hydroxy-6'-(3,3,3-trifluoropropoxy)spiro[cyclohexane-1,2'-inden]-1'(3'H)-one (Intermediate 18, 357 mg, 1.09 mmol) was dissolved in 2-Me THF (7 mL) under an inert atmosphere, and the solution was cooled to 0° C. Methyl iodide (88 μL, 1.41 mmol) was added followed by portionwise addition of potassium tert-butoxide (171 mg, 1.52 mmol). The resulting mixture was stirred at r.t. for 1 h. Some alcohol remained so more potassium tert-butoxide (61 mg, 0.54 mmol) was added and stirring continued. After 30 min, water and brine were added. The phases were separated and the organic layer was dried over MgSO$_4$ and concentrated. Purification by flash chromatography using 0-25% EtOAc in heptane as eluent afforded 201 mg (54% yield) of the title compound (containing 11% of another isomer): $^1$H NMR (500 MHz, CDCl$_3$) δ 1.32-1.44 (m, 2 H), 1.51 (d, 2 H), 1.78 (td, 2 H), 2.12-2.21 (m, 2 H), 2.59-2.70 (m, 2 H), 2.97 (s, 2 H), 3.24-3.32 (m, 1 H), 3.41 (s, 3 H), 4.23 (t, 2 H), 7.16-7.23 (m, 2 H), 7.37 (d, 1 H); MS (ES+) m/z 343 [M+H]$^+$.

Intermediate 20

6-(3-Fluoropropoxy)-2,3-dihydro-1H-inden-1-one

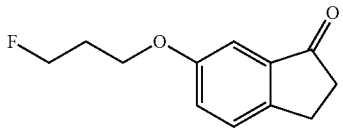 [SMILES: O=C1CCc2ccc(OCCCF)cc21]

The title compound (7.90 g, 94% yield) was prepared following the procedure for Intermediate 16, starting from 6-hydroxy-2,3-dihydro-1H-inden-1-one (5.98 g, 40.4 mmol) and 3-fluoropropan-1-ol (3.34 mL, 44.4 mmol). Additional 3-fluoropropan-1-ol (1.0 mL, 13.3 mmol) was added after stirring overnight to drive the reaction to completion. $^1$H NMR (500 MHz, CDCl$_3$) δ ppm 2.20 (m, 2 H) 2.73 (m, 2 H) 3.08 (m, 2 H) 4.14 (t, 2 H) 4.61 (t, 3 H) 4.70 (t, 1 H) 7.21 (m, 2 H) 7.38 (d, 1 H); MS (ES+) m/z 208 [M+H]$^+$.

Intermediate 21

6'-(3-Fluoropropoxy)-4-hydroxyspiro[cyclohexane-1,2'-inden]-1'(3'H)-one

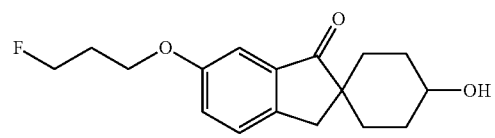 [SMILES: O=C1c2cc(OCCCF)ccc2CC12CCC(O)CC2]

The title compound was prepared following the method described for Intermediate 17 and in a subsequent step the method described for Intermediate 18, starting from 6-(3-fluoropropoxy)-2,3-dihydro-1H-inden-1-one (Intermediate 20, 3.16 g, 15.2 mmol) and methyl acrylate (3.01 mL, 33.4 mmol). The product was purified by flash chromatography (0-100% EtOAc in heptane) to afford the title compound as a 2:1 mixture of diastereomers (0.910 g, 32% yield). $^1$H NMR (500 MHz, CDCl$_3$) δ ppm 1.43-1.52 (m, 3 H) 1.74-1.85 (m, 2 H) 1.95 (td, 1 H) 2.14-2.24 (m, 2 H) 2.93-3.02 (m, 2 H) 3.73-3.80 (m, 1 H) 4.10-4.16 (m, 2 H) 4.61 (t, 1 H) 4.70 (t, 1 H) 7.18-7.22 (m, 2 H) 7.31-7.38 (m, 1 H); MS (ES+) m/z 293.09 [M+H]$^+$.

Intermediate 22

(1r,4r)-6'-bromo-4-(propan-2-yloxy)spiro[cyclohexane-1,2'-inden]-1'(3'H)-one

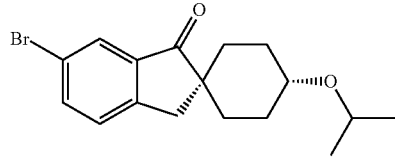 [SMILES: CC(C)O[C@H]1CC[C@]2(CC1)Cc1ccc(Br)cc1C2=O]

To a solution of 6'-bromospiro[cyclohexane-1,2'-indene]-1',4(3'H)-dione (Intermediate 2) (6.0 g, 20 mmol) and isopropoxytrimethylsilane (4.8 mL, 27 mmol) in DCM (150 mL) was added iron(III) chloride (0.33 g, 2.1 mmol) at r.t. The mixture was cooled to 0° C. and triethylsilane was added dropwise (4.0 mL, 25 mmol). The reaction mixture was stirred at 0° C. and allowed to warm to r.t. overnight. After 16 h, phosphate buffer (pH 7.4) was added and the phases were separated. The aqueous layer was extracted with DCM (3 times). The combined organic layers were washed with brine, dried over Na$_2$SO$_4$, filtered and concentrated under reduced pressure. The residue was purified by recrystallization in MeOH. The filtrate was concentrated under reduce pressure and purified by flash chromatography (0-15% EtOAc in heptanes). The fractions containing the desired product were combined and concentrated under reduced pressure. The resulting solid was recrystallized in MeOH. Combination of the solids afforded 3.5 g (51% yield) of the title compound. $^1$H NMR (300 MHz, CDCl$_3$) δ ppm 1.16 (d, 6 H), 1.32-1.49 (m, 4 H), 1.76 (td, 2 H), 2.01-2.07 (m, 2 H), 2.97 (s, 2 H), 3.35-3.45 (m, 1 H), 3.75 (sept, 1 H), 7.33 (d, 1 H), 7.68 (dd, 1 H), 7.86 (d, 1 H); MS (ES+) m/z 337.1, 339.1 [M+H]$^+$.

Intermediate 23

3-Chloro-5-(4,4,5,5-tetramethyl-1,3,2-dioxaborolan-2-yl)benzonitrile

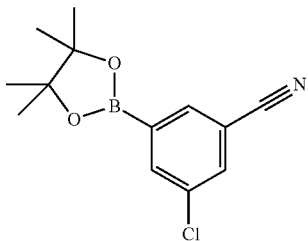 [SMILES: CC1(C)OB(c2cc(Cl)cc(C#N)c2)OC1(C)C]

A suspension of 4,4,4',4',5,5,5',5'-octamethyl-2,2'-bi(1,3,2-dioxaborolane) (665 mg, 2.62 mmol), 3-chloro-5-iodobenzonitrile (345 mg, 1.31 mmol), and potassium acetate (386 mg, 3.93 mmol) in dioxane (5 mL) was degassed with a stream of argon for a couple of min. PdCl$_2$(dppf) CH$_2$Cl$_2$ (53.5 mg, 0.07 mmol) was added and the mixture was heated at reflux under N$_2$ for 4 h. The mixture was allowed to cool and was then filtered. The filter cake was washed with EtOAc. The filtrate was concentrated in vacuo. The residue was purified by flash chromatography (eluent: heptane/EtOAc gradient) affording the title compound (69 mg, 20% yield). $^1$H NMR (400 MHz, DMSO-d$_6$) δ ppm 1.30 (s, 12 H), 7.88 (dd, 1 H), 7.90-7.94 (m, 1 H), 8.19 (dd, 1 H); MS (CI) m/z 264 [M+H]$^+$. The product has no UV-response but is visualized on TLC by a visualization agent containing phosphomolybdic acid and Ce(SO$_4$)$_2$.

Intermediate 24

3-Bromo-5-(prop-1-ynyl)pyridine

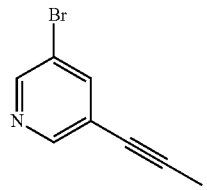

3,5-Dibromopyridine (30 g, 127 mmol), copper(I) iodide (7.24 g, 38.0 mmol) and tetrakis(triphenylphosphine)palladium(0) (4.39 g, 3.80 mmol) were mixed in toluene (120 mL) under nitrogen a atmosphere. 1-(Trimethylsilyl)-1-propyne (26.36 mL, 164.5 mmol), triethylamine (53.0 mL, 380 mmol) and tetra-n-butylammonium fluoride (12.66 mL, 12.66 mmol) were added. The mixture was heated to reflux and stirred under nitrogen overnight. Water (100 mL) was added to the reaction mixture was filtered and the phases separated. The organic phase was washed with 1 M HCl aq. (100 mL). The organic phase was concentrated and dissolved in MeOH (200 mL), filtered and concentrated. The mixture was dissolved in DCM and evaporated with silica gel to dryness, and then transferred to a silica gel column (300 g). The product was eluted with a gradient of EtOAc (0-5%) in heptane. The fractions containing the pure product was combined and evaporated to give the title compound (16.39 g, 66% yield): $^1$H NMR (500 MHz, CDCl$_3$) δ ppm 2.08 (s, 3 H), 7.82 (t, 1 H), 8.52 (d, 1 H), 8.55 (d, 1 H); MS (APCI+) m/z 197.0 [M+H]$^+$.

Intermediate 25

5-(Prop-1-ynyl)pyridin-3-ylboronic acid

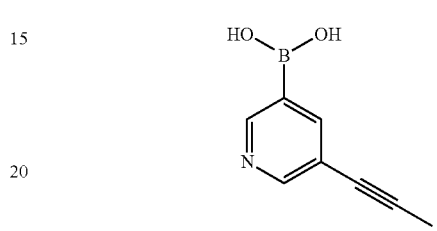

3-Bromo-5-(prop-1-ynyl)pyridine (Intermediate 24, 25 g, 117 mmol), 2-Me THF (60 mL), toluene (200 mL) and tri-isopropyl borate (33.2 mL, 140.78 mmol) were mixed. The mixture was cooled to −50° C. To the cold mixture was added n-BuLi (59.8 mL, 149.5 mmol) dropwise during 30 min. The mixture was stirred for 60 min. at −50° C. 2M HCl aq. (100 mL) was added. The mixture was then allowed to reach r.t. and stirred for 20 min. The organic and water phase were separated. The organic phase was extracted with NaOH (2M aq.) (2×100 mL). The water phases were combined and the pH was adjusted to pH 5. The product was extracted with 2-methyl-THF (2×100 mL). The organic phase was dried with Na$_2$SO$_4$, filtered and concentrated to give the title compound (16.47 g, 87% yield): $^1$H NMR (500 MHz, CD$_3$OD) δ ppm 2.11 (s, 3 H) 8.21 (br. s., 1 H) 8.53 (m, 2 H); MS (APCI+) m/z 162.2 [M+H]$^+$.

Intermediate 26

N-((1r,4r)-4-Hydroxy-5'-isobutoxyspiro[cyclohexane-1,2'-indene]-3'(1'H)-ylidene)-2-methylpropane-2-sulfinamide

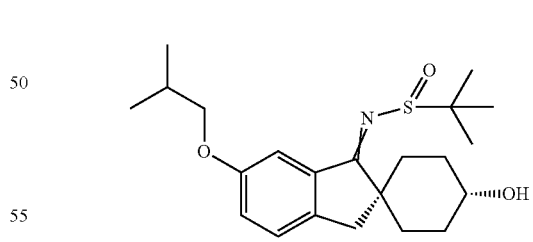

(1r,4r)-4-Hydroxy-6'-isobutoxyspiro[cyclohexane-1,2'-inden]-1'(3'H)-one (Intermediate 11, 3.84 g, 13.3 mmol) and tert-butyl sulfinamide (2.90 g, 24.0 mmol) were dissolved in 2-Me THF (40 mL). Titanium(IV) ethoxide (5.57 mL, 26.63 mmol) was added. The resulting mixture was heated to reflux overnight, more tert-butyl sulfinamide (1.61 g, 13.3 mmol) was added and the reaction was continued. After another day, more tert-butyl sulfinamide (1.13 g, 9.32 mmol) was added together with titanium(IV) ethoxide (2.78 mL, 13.3 mmol) and the mixture was left for 60 h. After a total of 4.5 days, the mixture was allowed to cool to r.t. EtOAc (120 mL) was added followed by the dropwise addition of water (20 mL) under vigorous stirring. After 10 min of stirring the mixture was allowed to stand still for 1 h before the formed solids were filtered off. The organic filtrate was dried (Na$_2$SO$_4$), filtered and concentrated. Purification by silica gel chromatography using a gradient of 0-40% EtOAc in n-heptane as eluent afforded the title compound (2.89 g, 55% yield). $^1$H NMR (500 MHz, CDCl$_3$-d) δ ppm 1.04 (d, 7 H) 1.32 (s, 9 H) 1.51 (m, 7 H) 2.03 (dd, 2 H) 2.09 (m, 1 H) 2.96 (s, 2 H) 3.77 (m, 3 H) 7.10 (dd, 1 H) 7.26 (s, 1 H) 7.88 (m, 1 H); MS (ES+) m/z 392.1 [M+H]$^+$.

Intermediate 27

(1r,4r)-1'-Imino-6'-isobutoxy-1',3'-dihydrospiro[cyclohexane-1,2'-inden]-4-ol

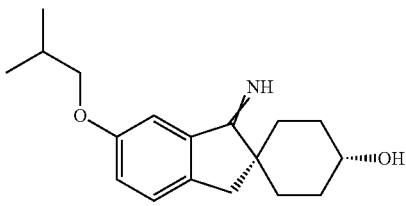 [SMILES: CC(C)COc1ccc2c(c1)C(=N)[C@]1(CC[C@H](O)CC1)C2]

HCl (4 M in 1,4-dioxane) (18.5 mL, 73.8 mmol) was added to a solution of N-((1r,4r)-4-hydroxy-5'-isobutoxyspiro[cyclohexane-1,2'-indene]-3'(1'H)-ylidene)-2-methylpropane-2-sulfinamide (Intermediate 26, 2.89 g, 7.38 mmol) in anhydrous 1,4-dioxane (10 mL). The resulting mixture was stirred under a nitrogen atmosphere at r.t. for 1.5 h. Et$_2$O (150 mL) was added and the formed solid was filtered off and washed with Et$_2$O. The solid was partitioned between dichloromethane and saturated aqueous NaHCO$_3$. The phases were separated and the organic layer dried over Na$_2$SO$_4$, filtered and concentrated to afford the title compound (1.67 g, 79% yield). MS (ES+) m/z 288.1 [M+H]$^+$.

Intermediate 28

(1r,4r)-4-Hydroxy-5''-methyl-6'-(2-methylpropoxy)-3'H-dispiro[cyclohexane-1,2'-indene-1',2''-imidazole]-4''(3''H)-thione

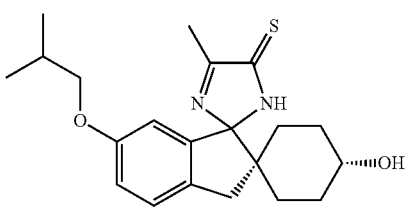

(1r,4r)-1'-Imino-6'-isobutoxy-1',3'-dihydrospiro[cyclohexane-1,2'-inden]-4-ol (Intermediate 27, 1.67 g, 5.80 mmol) was dissolved in dry MeOH (30 mL) and heated to 60° C. 2-Oxopropanethioamide (Intermediate 1, 1.80 g, 17.4 mmol) was added in two portions and the mixture was heated at 60° C. under a nitrogen atmosphere for 18 h. The mixture was allowed to cool to r.t. and the solvent was evaporated. Purification by silica gel chromatography using a gradient of 0-50% EtOAc in n-heptane afforded the title compound (1.94 g, 90% yield). $^1$H NMR (500 MHz, CDCl$_3$-d) δ ppm 0.99 (s, 3 H) 1.00 (s, 3 H) 1.30 (m, 2 H) 1.44 (m, 2 H) 1.64 (m, 2 H) 1.73 (dd, 1 H) 1.91 (m, 2 H) 2.03 (m, 1 H) 2.39 (s, 3 H) 3.07 (s, 2 H) 3.56 (m, 1 H) 3.63 (d, 2 H) 6.42 (d, 1 H) 6.86 (dd, 1 H) 7.21 (d, 1 H) 9.17 (s, 1 H); MS (ES+) m/z 373.1 [M+H]$^+$.

Intermediate 29

N-[(1r,4r)-4-Methoxy-6'-(3,3,3-trifluoropropoxy)spiro[cyclohexane-1,2'-inden]-1'(3'H)-ylidene]-2-methylpropane-2-sulfinamide

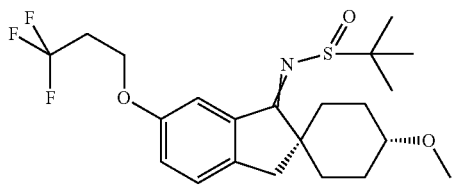 [SMILES: CO[C@H]1CC[C@]2(CC1)Cc1ccc(OCCC(F)(F)F)cc1C2=NS(=O)C(C)(C)C]

(1r,4r)-4-Methoxy-6'-(3,3,3-trifluoropropoxy)spiro[cyclohexane-1,2'-inden]-1'(3'H)-one (Intermediate 19, 320 mg, 0.93 mmol) and 2-methylpropane-2-sulfinamide (204 mg, 1.68 mmol) were dissolved in 2-Me THF (4 mL). Titanium (IV) ethoxide (0.391 mL, 1.87 mmol) was added. The resulting mixture was heated at reflux over a weekend. The mixture was allowed to cool to r.t. and EtOAc (10 mL) was added followed by dropwise addition of water (5 mL) under vigorous stirring. After 10 min of stirring the mixture was allowed to stand still for 1 h before the formed solids were filtered off. The organic layer was dried over Na$_2$SO$_4$ and concentrated. Purification of the product by flash chromatography using 0-20% EtOAc in heptane as eluent afforded 270 mg (65% yield) of the title compound (containing 5% of another isomer): $^1$H NMR (500 MHz, CDCl$_3$) δ 1.32-1.35 (m, 9 H), 1.36-1.45 (m, 2 H), 1.52-1.57 (m, 1 H), 1.60-1.68 (m, 1 H), 1.72-2.07 (m, 2 H), 2.13 (d, 2 H), 2.63 (dt, 2 H), 2.97 (s, 2 H), 3.21-3.32 (m, 1 H), 3.40 (s, 3 H), 4.26 (td, 2 H), 7.11 (dd, 1 H), 7.29 (d, 1 H), 7.87-8.13 (m, 1 H); MS (ES+) m/z 446 [M+H]$^+$.

Intermediate 30

(1r,4r)-4-Methoxy-6'-(3,3,3-trifluoropropoxy)spiro[cyclohexane-1,2'-inden]-1'(3'H)-imine

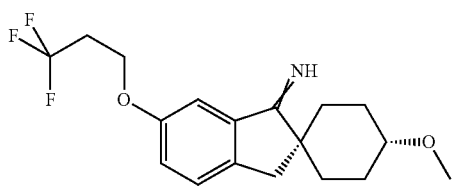 [SMILES: CO[C@H]1CC[C@]2(CC1)Cc1ccc(OCCC(F)(F)F)cc1C2=N]

HCl (4 M in 1,4-dioxane) (1.52 mL, 6.06 mmol) was added to a solution of N-((1r,4r)-4-methoxy-5'-(3,3,3-trifluoropropoxy)spiro[cyclohexane-1,2'-indene]-3'(1'H)-ylidene)-2-methylpropane-2-sulfinamide (Intermediate 29, 270 mg, 0.61 mmol) in anhydrous 1,4-dioxane (1 mL). The resulting mixture was stirred under N$_2$ at r.t. for 2 h. The mixture was concentrated to ~⅓ of the volume and Et$_2$O (40 mL) was added. A solid was formed which was filtered off and washed with Et₂O. The solid was partitioned between DCM and sat. aq. NaHCO₃. The phases were separated and the organic layer dried over Na₂SO₄ and concentrated in vacuo. The product (174 mg, 84% yield) containing 9% of another isomer was used immediately in the next step: MS (ES+) m/z 342 [M+H]⁺.

Intermediate 31

(1r,4r)-4-Methoxy-5″-methyl-6′-(3,3,3-trifluoropropoxy)-3′H-dispiro[cyclohexane-1,2′-indene-1′,2″-imidazole]-4″(3″H)-thione

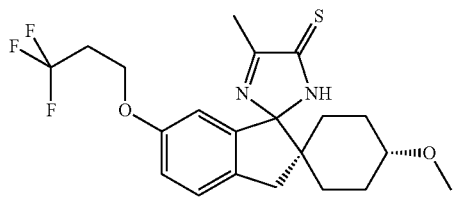

2-Oxopropanethioamide (Intermediate 1, 158 mg, 1.53 mmol) and 4-methoxy-6′-(3,3,3-trifluoropropoxy)spiro[cyclohexane-1,2′-inden]-1′(3′H)-imine (Intermediate 30, 174 mg, 0.51 mmol) were dissolved in dry MeOH (3 mL) and the resulting orange solution was heated at 60° C. under a nitrogen atmosphere overnight. The mixture was allowed to cool to r.t. and the solvent was evaporated in vacuo. Purification by flash chromatography using a gradient of 0-30% EtOAc in heptane as eluent afforded 175 mg (81% yield) of the title compound containing 5% of another isomer: ¹H NMR (500 MHz, CDCl₃) δ 1.15-1.24 (m, 1 H), 1.34-1.53 (m, 2 H), 1.56-1.69 (m, 2 H), 1.75 (dd, 1 H), 2.02 (dt, 2 H), 2.40 (s, 3 H), 2.53-2.64 (m, 2 H), 3.08 (s, 2 H), 3.09-3.13 (m, 1 H), 3.35 (s, 3 H), 4.12 (t, 2 H), 6.44 (s, 1 H), 6.87 (d, 1 H), 7.24 (d, 1 H), 8.84 (br. s., 1 H); MS (ES+) m/z 387 [M+H]⁺.

Intermediate 32

N-(5′-(3-Fluoropropoxy)-4-hydroxyspiro[cyclohexane-1,2′-indene]-3′(1′H)-ylidene)-2-methylpropane-2-sulfinamide

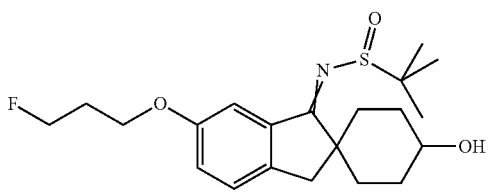 [SMILES: CC(C)(C)S(=O)N=C1c2cc(OCCCF)ccc2CC12CCC(O)CC2]

6′-(3-Fluoropropoxy)-4-hydroxyspiro[cyclohexane-1,2′-inden]-1′(3′H)-one (Intermediate 21, 0.91 g, 3.11 mmol), 2-methylpropane-2-sulfinamide (0.566 g, 4.67 mmol) and titanium(IV) ethoxide (1.283 mL, 6.23 mmol) were dissolved in 2-Me THF (8 mL) and heated to reflux over a weekend. More 2-methyl-2-propanesulfinamide (0.189 g, 1.56 mmol) and titanium(IV) ethoxide (0.325 mL, 1.56 mmol) were added, and the mixture was refluxed overnight. The reaction was cooled to r.t. EtOAc (50 mL) and water (10 mL) were added under stirring. The mixture were let to stand still for 1 h. The organic phase was collected by filtration, dried, and concentrated. The residue was purified by flash column chromatography using a gradient of 0-40% EtOAc in heptane, to give 0.278 g (23% yield) of the title compound. ¹H NMR (500 MHz, CDCl₃) δ ppm 1.33 (s, 9 H) 1.45-1.54 (m, 4 H) 1.87 (br. s., 1 H) 2.03 (dd, 2 H) 2.14-2.19 (m, 1 H) 2.20-2.25 (m, 1 H) 2.93-3.01 (m, 2 H) 3.71-3.80 (m, 1 H) 4.13-4.18 (m, 2 H) 4.59-4.66 (m, 1 H) 4.69-4.75 (m, 1 H) 7.11 (dd, 1 H) 7.29 (s, 1 H); MS (ES+) m/z 396.11 [M+H]⁺.

Intermediate 33

6′-(3-Fluoropropoxy)-4-hydroxy-5″-methyl-3′H-dispiro[cyclohexane-1,2′-indene-1′,2″-imidazole]-4″(3″H)-thione

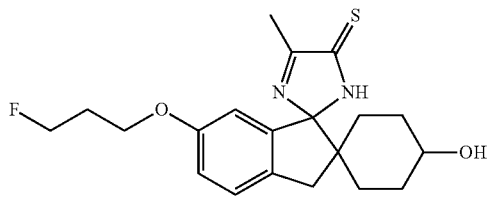 [SMILES: CC1=NC2(NC1=S)c1cc(OCCCF)ccc1CC21CCC(O)CC1]

To N-(5′-(3-fluoropropoxy)-4-hydroxyspiro[cyclohexane-1,2′-indene]-3′(1′H)-ylidene)-2-methylpropane-2-sulfinamide (Intermediate 32, 275 mg, 0.70 mmol) in dioxane (1 mL) under an atmosphere of nitrogen was added HCl (4 M in 1,4-dioxane, 1.74 mL, 6.95 mmol). The mixture was stirred at r.t. for 2 h and was then concentrated. DCM (1-2 mL) and Et₂O was added and a solid was formed. The solid was filtered off and washed with diethylether. The solid was dissolved in DCM. Sat. aq. NaHCO₃ was added and mixture was poured in to a phase separator. The organic phase was collected and concentrated to give 6′-(3-fluoropropoxy)-1′-imino-1′,3′-dihydrospiro[cyclohexane-1,2′-inden]-4-ol (227 mg). The obtained imine was mixed with 2-oxopropanethioamide (Intermediate 1, 239 mg, 2.32 mmol) in dry MeOH (4 mL) and the resulting orange solution was heated at 60° C. under an atmosphere of nitrogen overnight. The mixture was allowed to cool to r.t., and concentrated. The residue was purified by flash column chromatography using a gradient of 0-100% EtOAc in heptane, providing 104 mg (36% yield) of the title compound. ¹H NMR (500 MHz, DMSO-d₆) δ ppm 1.04-1.21 (m, 4 H) 1.41-1.48 (m, 2 H) 1.66-1.73 (m, 2 H) 2.02 (t, 1 H) 2.07 (quin, 1 H) 2.26 (s, 3 H) 2.93 (d, 1 H) 3.01 (d, 1 H) 3.22-3.29 (m, 1 H) 3.97 (tq, 2 H) 4.52 (t, 1 H) 4.55 (d, 1 H) 4.62 (t, 1 H) 6.32 (d, 1 H) 6.89 (dd, 1 H) 7.26 (d, 1 H) 12.28 (s, 1 H); MS (ES+) m/z 377.07 [M+H]+.

Intermediate 34

N-((1r,4′0-5′-Bromo-4-isopropoxyspiro[cyclohexane-1,2′-indene]-3′(1′H)-ylidene)-2-methylpropane-2-sulfinamide

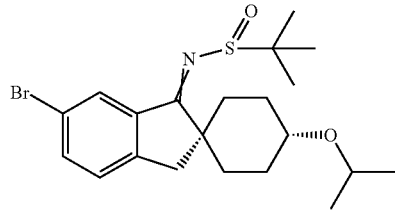 [SMILES: CC(C)O[C@H]1CC[C@]2(CC1)Cc1ccc(Br)cc1C2=NS(=O)C(C)(C)C]

(1r,4r)-6'-Bromo-4-isopropoxyspiro[cyclohexane-1,2'-inden]-1'(3'H)-one (Intermediate 22, 535 mg, 1.59 mmol) and 2-methyl-2-propanesulfinamide (346 mg, 2.86 mmol) were dissolved in 2-Me THF (5.35 mL). Titanium(IV) ethoxide (0.663 mL, 3.17 mmol) was added. The resulting mixture was heated at reflux for three days. More 2-methyl-2-propanesulfinamide (260 mg, 2.14 mmol) and titanium ethoxide (0.490 mL, 2.38 mmol) were added and the mixture was further refluxed for one day after which more 2-methyl-2-propanesulfinamide (250 mg, 2.06 mmol), titanium ethoxide (0.490 mL, 2.38 mmol) and 2-Me THF (1 mL) were added and the reflux was resumed for one day. EtOAc (11 mL) was added followed by water (2 mL) under vigorous stirring. After 10 min of stirring the mixture was filtered through a mixture of $Na_2SO_4$ and diatomaceous earth and then concentrated. Purification by flash silica gel chromatography using a gradient of n-heptane/EtOAc (6:1-5:1-4:1-3:1) gave the title compound (328 mg, 47% yield). $^1$H NMR (500 MHz, DMSO-$d_6$) δ ppm 1.07 (d, 6 H), 1.24 (s, 9 H), 1.26-1.39 (m, 2 H), 1.43-1.56 (m, 2 H), 1.66 (br. s., 2 H), 1.86-1.99 (m, 2 H), 3.01 (s, 2 H), 3.34-3.40 (m, 1 H), 3.72 (dt, 1 H), 7.48 (d, 1 H), 7.78 (dd, 1 H), 8.52 (br. s., 1 H); MS (ES+) m/z 440.0 [M+H]$^+$.

Intermediate 35

(1r,4r)-6'-Bromo-4-isopropoxyspiro[cyclohexane-1,2'-inden]-1'(3'H)-imine

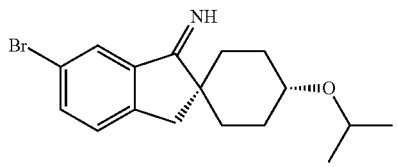 [SMILES: CC(C)O[C@H]1CC[C@]2(CC1)Cc1ccc(Br)cc1C2=N]

The title compound (217 mg, 87% yield) was prepared using the procedure described for Intermediate 27, starting from N-((1r,4r)-5'-bromo-4-isopropoxyspiro[cyclohexane-1,2'-indene]-3'(1'H)-ylidene)-2-methylpropane-2-sulfinamide (Intermediate 34, 325 mg, 0.74 mmol). MS (ES+) m/z 336.0 [M+H]$^+$.

Intermediate 36

(1r,4r)-6'-Bromo-5''-methyl-4-(propan-2-yloxy)-3'H-dispiro[cyclohexane-1,2'-indene-1',2''-imidazole]-4''(3''H)-thione

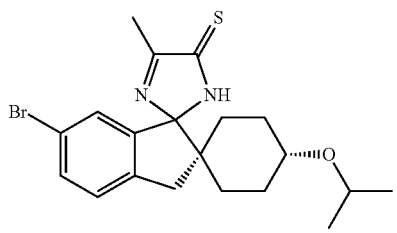

The title compound was prepared using the procedure described for Intermediate 28, starting from 6'-bromo-4-isopropoxyspiro[cyclohexane-1,2'-inden]-1'(3'H)-imine (Intermediate 35, 217 mg, 0.65 mmol). The reaction time was 45 h. Purification by flash column chromatography using a gradient of n-heptane/EtOAc (3:1-2.1-1.1) gave the title compound (231 mg, 85% yield). $^1$H NMR (500 MHz, DMSO-$d_6$) δ ppm 1.03 (d, 6 H), 1.06-1.18 (m, 1 H), 1.18-1.30 (m, 3 H), 1.40-1.51 (m, 2 H), 1.72-1.83 (m, 2 H), 2.27 (s, 3 H), 2.99 (d, 1 H), 3.07 (d, 1H), 3.18 (m, 1 H), 3.65 (spt, 1 H), 6.98 (s, 1 H), 7.33 (d, 1 H), 7.46-7.56 (m, 1 H), 12.34 (s, 1 H); MS (ES+) m/z 421.0 [M+H]$^+$.

Intermediate 37

Di-tert-butyl [(1r,4r)-6'-bromo-5''-methyl-4-(propan-2-yloxy)-3'H-dispiro[cyclohexane-1,2'-indene-1',2''-imidazol]-4''-yl]imidodicarbonate

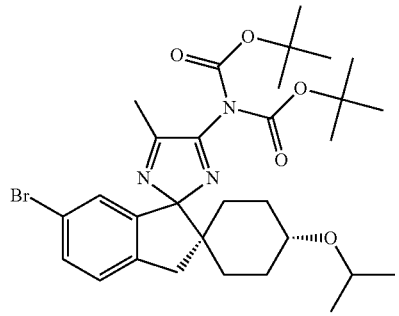

Di-tert-butyl dicarbonate (163 mg, 0.75 mmol), triethyl amine (90 μL, 0.64 mmol) and DMAP (5 mg, 0.04 mmol) were added to a suspension of (1r,4r)-6'-bromo-5''-methyl-4-(propan-2-yloxy)-3'H-dispiro[cyclohexane-1,2'-indene-1',2''-imidazol]-4''-amine (Example 16, 124 mg, 0.31 mmol) in dichloromethane (2.5 mL). The resulting mixture was stirred at r.t. for 2.5 days. The reaction mixture was diluted with $CH_2Cl_2$ and washed with 1 M HCl, water, sat. aq. $NaHCO_3$ and brine. It was filtered through a phase separator and concentrated to give the title compound (183 mg, 99% yield). $^1$H NMR (500 MHz, DMSO-$d_6$) δ ppm 1.02 (d, 6 H), 1.19-1.32 (m, 4 H), 1.44 (s, 18 H), 1.51-1.59 (m, 2 H), 1.69-1.79 (m, 2 H), 2.23 (s, 3 H), 3.05-3.17 (m, 3 H), 3.63 (septett, 1 H), 6.65 (d, 1 H), 7.37 (d, 1 H), 7.47 (dd, 1 H); MS (ES+) m/z 604.0 [M+H]$^+$.

EXAMPLES

Example 1

(1r,4r)-4''-Amino-5''-methyl-6'-(2-methylpropoxy)-3'H-dispiro[cyclohexane-1,2'-indene-1',2''-imidazol]-4-ol

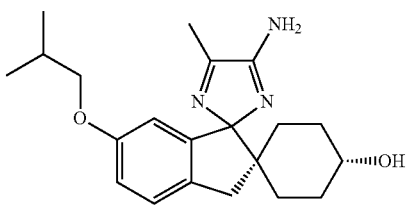

(1r,4r)-4-Hydroxy-5''-methyl-6'42-methylpropoxy)-3'H-dispiro[cyclohexane-1,2'-indene-1',2''-imidazole]-4''(3''H)-thione (Intermediate 37, 1.94 g, 5.20 mmol) and ammonia (7

M in MeOH, 15 mL, 105 mmol) were heated in a MW reactor at 110° C. for 30 min. The mixture was concentrated and the residue was dissolved in new ammonia (7 M in MeOH, 15 mL, 105 mmol) and heated once more at 110° C. for 30 min. This was repeated three more times. After evaporation of the solvent, the residue was partitioned between EtOAc and 2 M aq. citric acid. The phases were separated and the organic layer was re-extracted with 2 M aq. citric acid. The combined aqueous phases were basified to pH 12 by addition of 50% aq. NaOH and extracted twice with EtOAc. The combined organic layers from the basic extraction were treated with charcoal and filtered through diatomaceous earth and concentrated. $^1$H NMR (500 MHz, DMSO-$d_6$) δ ppm 0.88 (m, 1 H), 0.93 (d, 6 H), 1.22 (m, 2 H), 1.38 (m, 3 H), 1.62 (d, 2 H), 1.92 (dt, 1 H), 2.14 (s, 3 H), 2.89 (m, 2 H), 3.19 (dd, 1 H), 3.58 (dd, 2 H), 4.44 (d, 1 H), 6.04 (d, 1 H), 6.49 (s, 2 H), 6.70 (dd, 1 H), 7.15 (d, 1 H); MS (ES+) m/z 356.1 [M+H]$^+$.

Example 2

Separation of the isomers of (1r,4r)-4"-Amino-5"-methyl-6'-(2-methylpropoxy)-3'H-dispiro[cyclohexane-1,2'-indene-1',2"-imidazol]-4-ol The isomers of (1r,4r)-4"-Amino-5"-methyl-6'42-methylpropoxy)-3'H-dispiro[cyclohexane-1,2'-indene-1',2"-imidazol]-4-ol were separated using SFC Berger Multigram II, with a LuxC4; 20*250 mm; 5 μm column, and a mobile phase consisting of 30% MeOH (containing 0.1% DEA) and 70% CO$_2$ at a flow rate of 50 mL/min to give:

Isomer 1:
(1r,1'R,4R)-4"-Amino-5"-methyl-6'-(2-methylpropoxy)-3'H-dispiro[cyclohexane-1,2'-indene-1',2"-imidazol]-4-ol (0.593 g, 31% yield) with retention time 2.5 min:

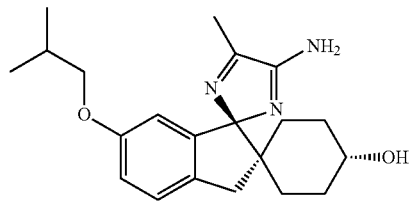 [SMILES: CC1=N[C@]2(N=C1N)c1cc(OCC(C)C)ccc1C[C@]21CC[C@@H](O)CC1]

$^1$H NMR (500 MHz, DMSO-$d_6$) δ ppm 7.15 (d, 1 H), 6.70 (dd, 1 H), 6.49 (s, 2 H), 6.04 (d, 1 H), 4.44 (d, 1 H), 3.53-3.62 (m, 2 H), 3.18-3.25 (m, 1 H), 2.95 (d, 1 H), 2.84 (d, 1 H), 2.14 (s, 3 H), 1.92 (dt, 1 H), 1.63 (dt, 2 H), 1.31-1.45 (m, 3 H), 1.11-1.31 (m, 2 H), 0.93 (d, 6H), 0.87 (td, 1 H); MS (ES+) m/z 356.1 [M+H]$^+$.
Isomer 2: (1r,1'S,4S)-4"-amino-5"-methyl-6'-(2-methylpropoxy)-3'H-dispiro[cyclohexane-1,2'-indene-1',2"-imidazol]-4-ol (0.562 g, 30% yield) with retention time 3.45 min.

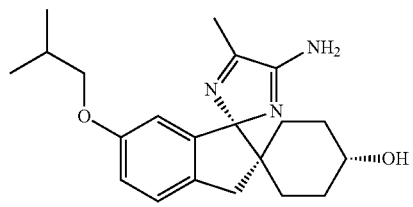 [SMILES: CC1=N[C@@]2(N=C1N)c1cc(OCC(C)C)ccc1C[C@]21CC[C@@H](O)CC1]

$^1$H NMR (500 MHz, DMSO-$d_6$) δ ppm 7.15 (d, 1 H), 6.70 (dd, 1 H), 6.49 (s, 2 H), 6.04 (d, 1 H), 4.44 (d, 1 H), 3.54-3.63 (m, 2 H), 3.13-3.24 (m, 1 H), 2.95 (d, 1 H), 2.84 (d, 1 H), 2.14 (s, 3 H), 1.92 (dt, 1 H), 1.63 (dt, 2 H), 1.32-1.44 (m, 3 H), 1.11-1.31 (m, 2 H), 0.93 (d, 6 H), 0.87 (td, 1 H); MS (ES+) m/z 356.1 [M+H]$^+$.

Example 3

(1r,4r)-6'-(2,2-Difluoropropoxy)-4-methoxy-5"-methyl-3'H-dispiro[cyclohexane-1,2'-indene-1',2"-imidazol]-4"-amine

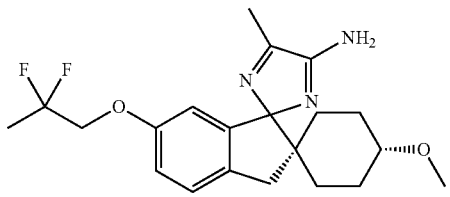

Di-t-butyl [(1r,4r)-6'-bromo-4-methoxy-5"-methyl-3'H-dispiro[cyclohexane-1,2'-indene-1',2"-imidazol]-4"-yl]imidodicarbonate (Intermediate 12, 214 mg, 0.37 mmol), allylpalladium(II) chloride (6 mg, 0.01 mmol), di-tert-butyl (2',4',6'-triisopropyl-3-methoxy-6-methylbiphenyl-2-yl)phosphine (17 mg, 0.04 mmol) and Cs$_2$CO$_3$ (181 mg, 0.56 mmol) were placed in a tube. Toluene (2.5 mL) was added and the head space was evacuated and refilled with argon. 2,2-Difluoropropan-1-ol (107 mg, 1.11 mmol) was added and the mixture was heated to 100° C. in a MW apparatus for 2 h. 7 M methanolic ammonia (2 mL, 14 mmol) and water (0.27 mL, 15 mmol) was added and the mixture was heated to 80° C. for 48 h. The organic solvents were evaporated and the aqueous residue was extracted with DCM. The combined extracts were concentrated and the residue was purified by prep HPLC. Methanol was evaporated from the collected fractions, 1 M citric acid was added and the aqueous mixture was extracted with DCM. The combined organic layers were extracted with 1 M citric acid, the combined citric acid layers were made basic with 20% aqueous NaOH and then extracted with DCM. The combined DCM extracts from the latter extraction was dried over Na$_2$SO$_4$ and evaporated to give 35 mg of the title compound (26% yield). $^1$H NMR (500 MHz, DMSO-$d_6$) δ ppm 0.92 (m, 1 H), 1.09-1.27 (m, 2 H), 1.33-1.48 (m, 3 H), 1.68 (t, 3 H), 1.80 (m, 2 H), 2.15 (s, 3 H), 2.82-3.00 (m, 3 H), 3.18 (s, 3 H), 4.13 (m, 2 H), 6.15 (s, 1 H), 6.52 (br. s., 2 H), 6.80 (dd, 1 H), 7.19 (d, 1 H). MS (APCI+) m/z 392 [M+H]$^+$.

Example 4

(1r,4r)-4"-Amino-6'-bromo-5"-methyl-3'H-dispiro[cyclohexane-1,2'-indene-1',2"-imidazol]-4-01

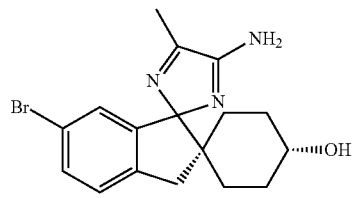

(1r,4r)-6'-Bromo-4-hydroxy-5"-methyl-3'H-dispiro[cyclohexane-1,2'-indene-1',2"-imidazole]-4"(3"H)-thione (Intermediate 10, 2.48 g, 6.54 mmol) was taken up in ammonia (7 M in MeOH, 20 mL, 140 mmol) and the resulting mixture was heated in the MW reactor at 110° C. for 30 min. The solvent was evaporated. This procedure was repeated twice more. After evaporation of the solvent, the residue was partioned between 2 M citric acid and EtOAc. The phases were separated, and the water layer was extracted with EtOAc. The water phase was set aside, and the collected organic phases were combined, dried over MgSO$_4$, filtered, and concentrated. The residue was dissolved in ammonia (7 M in MeOH, 20 mL, 140 mmol), and heated in the MW reactor at 110° C. for 30 min. The solvent was evaporated, and more ammonia (7 M in MeOH, 20 mL, 140 mmol) was added. This process was repeated a total of five times. After the completion of the cycles, the reaction mixture was concentrated, and the residue was partitioned between EtOAc and 2 M citric acid. The organic phase was washed with 2M citric acid twice more. The organic phase was then discarded. The combined aqueous phases from the consecutive runs were basified with 50% aq. NaOH to adjust the pH ~9-12 and it was then extracted with EtOAc twice. The combined organic phases were treated with charcoal and filtered through diatomaceous earth. The diatomaceous earth was rinsed with EtOAc and the organic phase was concentrated to give the title compound (1.62 g, 68% yield). $^1$H NMR (500 MHz, DMSO-d$_6$) δ ppm 0.90 (td, 1 H) 1.19-1.30 (m, 2 H) 1.34-1.40 (m, 3 H) 1.59-1.68 (m, 2 H) 2.15 (s, 3 H) 2.89 (d, 1 H) 3.00 (d, 1 H) 3.16-3.24 (m, 1 H) 4.46 (d, 1 H) 6.57 (br. s., 2 H) 6.64 (s, 1 H) 7.26 (d, 1 H) 7.34 (d, 1 H); MS (ES+) m/z 361.98 [M+H]$^+$.

Example 5

Separation of the isomers of (1r,4r)-4"-Amino-6'-bromo-5"-methyl-3'H-dispiro[cyclohexane-1,2'-indene-1',2"-imidazol]-4-ol (1r,4r)-4"-Amino-6'-bromo-5"-methyl-3'H-dispiro[cyclohexane-1,2'-indene-1',2"-imidazol]-4-ol (Example 4, 1.2 g) was subjected to chiral separation on a SFC Berger Multigram II with a LuxC4; 20*250 mm; 5 μm column and a mobile phase consisting of 30% MeOH (containing 0.1% DEA) and 70% CO$_2$ at a flow rate of 50 mL/min to give:
Isomer 1
(1r,1'R,4R)-4"-amino-6'-bromo-5"-methyl-3'H-dispiro[cyclohexane-1,2'-indene-1',2"-imidazol]-4-ol as the first eluting isomer with RT 2.6 min (516 mg, 43% yield):

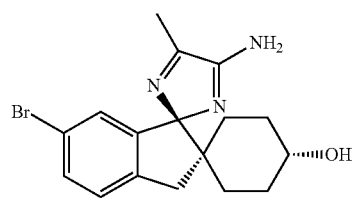 [SMILES: CC1=N[C@]2(N=C1N)c1cc(Br)ccc1C[C@]21CC[C@@H](O)CC1]

is $^1$H NMR (500 MHz, DMSO-d$_6$) δ ppm 0.90 (td, 1 H) 1.19-1.30 (m, 2 H) 1.34-1.40 (m, 3 H) 1.59-1.68 (m, 2 H) 2.15 (s, 3 H) 2.89 (d, 1 H) 3.00 (d, 1 H) 3.16-3.24 (m, 1 H) 4.46 (d, 1 H) 6.57 (br. s., 2 H) 6.64 (s, 1 H) 7.26 (d, 1 H) 7.34 (d, 1 H); MS (ES+) m/z 362 [M+H]$^+$.
and Isomer 2

(1r,1'S,4S)-4"-amino-6'-bromo-5"-methyl-3'H-dispiro[cyclohexane-1,2'-indene-1',2"-imidazol]-4-ol as the second eluting isomer with RT 3.6 min (557 mg, 46% yield):

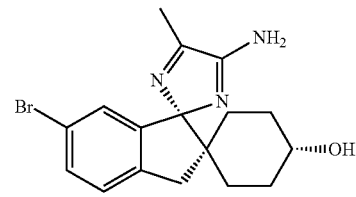 [SMILES: CC1=N[C@@]2(N=C1N)c1cc(Br)ccc1C[C@]21CC[C@@H](O)CC1]

$^1$H NMR (500 MHz, DMSO-d$_6$) δ ppm 0.90 (td, 1 H) 1.19-1.30 (m, 2 H) 1.34-1.40 (m, 3 H) 1.59-1.68 (m, 2 H) 2.15 (s, 3 H) 2.89 (d, 1 H) 3.00 (d, 1 H) 3.16-3.24 (m, 1 H) 4.46 (d, 1 H) 6.57 (br. s., 2 H) 6.64 (s, 1 H) 7.26 (d, 1 H) 7.34 (d, 1 H); MS (ES+) m/z 362 [M+H]$^+$.

Example 6

(1r,4r)-6'-(Cyclobutylethynyl)-4-methoxy-5"-methyl-3'H-dispiro[cyclohexane-1,2'-indene-1',2"-imidazol]-4"-amine

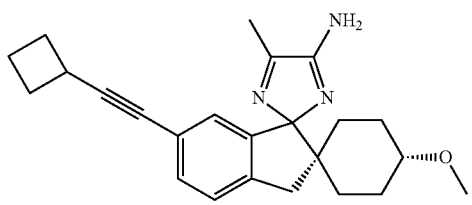

To a mixture of (1r,4r)-6'-bromo-4-methoxy-5"-methyl-3'H-dispiro[cyclohexane-1,2'-indene-1',2"-imidazol]-4"-amine (Intermediate 8, isomeric mixture 2, Method B, 0.168 g, 0.45 mmol), K$_2$CO$_3$ (0.093 g, 0.67 mmol), copper(I) iodide (5.10 mg, 0.03 mmol), tetrakis(triphenylphosphine)palladium(0) (0.031 g, 0.03 mmol) in DMF (10 mL) was added (cyclobutylethynyl)trimethylsilane (0.102 g, 0.67 mmol) (see Kozhushkov, S. I.; Wagner-Gillen, K.; Khlebnikov A. F.; de Meijere, A. Synthesis 2010 (23), 3967-3973). The atmosphere over the reaction mixture was exchanged to argon and the mixture was heated to 70° C. overnight. The reaction was allowed to reach r.t. EtOAc and brine were added. The organic phase was dried over MgSO$_4$, filtered and concentrated in vacuo. The residue was purified by preparative chromatography to give the title compound (73 mg, 44% yield): $^1$H NMR (500 MHz, DMSO-d$_6$) δ ppm 1.28 (d, 1 H), 1.49 (d, 2 H), 1.70-1.83 (m, 3 H), 2.10-2.21 (m, 3 H), 2.21-2.31 (m, 1 H), 2.41 (td, 2 H), 2.50 (s, 3 H), 2.55-2.65 (m, 2 H), 3.23-3.42 (m, 3 H), 3.50-3.59 (m, 4 H), 6.85 (s, 1 H), 6.88 (s, 2 H), 7.51 (dd, 1 H), 7.59 (d, 1 H); MS (ES+) m/z 376 [M+H]$^+$.

Example 7

Separation of the isomers of (1r,4r)-4-methoxy-5"-methyl-6'-(3-methylbut-1-yn-1-yl)-3'H-dispiro[cyclohexane-1,2'-indene-1',2"-imidazol]-4"-amine The enantiomers of (1r,4r)-4-methoxy-5"-methyl-6'-(3-methylbut-1-yn-1-yl)-3'H-dispiro[cyclohexane-1,2'-indene-1',2"-imidazol]-4"-amine (Example 6, 0.052 g) were separated in 3 injections of 18 mg each using a SFC Berger Multigram II system, with a LuxC4; 20*250 mm; 5 μm column, and a mobile phase consisting of 20% MeOH (containing 0.1% DEA) and 80% CO₂ at a flow rate of 50 mL/min, to give:
Isomer 1 (1r,1'R,4R)-6'-(cyclobutylethynyl)-4-methoxy-5"-methyl-3'H-dispiro[cyclohexane-1,2'-indene-1',2"-imidazol]-4"-amine with retention time 6 min (22.9 mg, 41% yield).

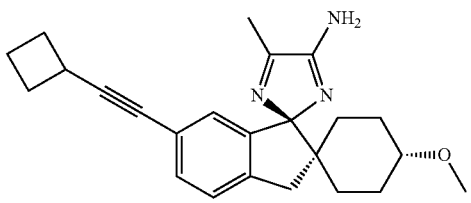 [SMILES: CO[C@H]1CC[C@]2(CC1)Cc1ccc(C#CC3CCC3)cc1[C@@]21N=C(C)C(N)=N1]

¹H NMR (500 MHz, DMSO-d₆) δ ppm 0.88-0.99 (m, 1 H) 1.09-1.29 (m, 2 H) 1.34-1.48 (m, 3 H) 1.75-1.96 (m, 4 H) 2.02-2.12 (m, 2 H) 2.16 (s, 3 H) 2.21-2.32 (m, 2 H) 2.86-3.07 (m, 3 H) 3.17 (d, 0 H) 3.18 (s, 3 H) 3.20-3.25 (m, 1 H) 6.50 (d, 1 H) 6.54 (s, 2 H) 7.17 (dd, 1 H) 7.24 (d, 1 H); MS (ES+) m/z 376 [M+H]⁺.
and Isomer 2 (1r,1'S,4S)-6'-(cyclobutylethynyl)-4-methoxy-5"-methyl-3'H-dispiro[cyclohexane-1,2'-indene-1',2"-imidazol]-4"-amine with retention time 10 min (24.0 mg, 43% yield).

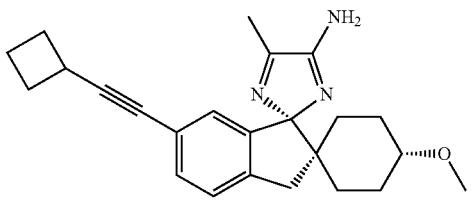 [SMILES: CO[C@H]1CC[C@]2(CC1)Cc1ccc(C#CC3CCC3)cc1[C@]21N=C(C)C(N)=N1]

¹H NMR (500 MHz, DMSO-d₆) δ ppm 0.88-1.00 (m, 1 H) 1.08-1.29 (m, 2 H) 1.33-1.48 (m, 3 H) 1.76-1.96 (m, 4 H) 2.01-2.12 (m, 2 H) 2.16 (s, 3 H) 2.21-2.31 (m, 2 H) 2.89-3.07 (m, 3 H) 3.17 (br. s., 0 H) 3.18 (s, 3 H) 3.20-3.24 (m, 1 H) 6.50 (d, 1 H) 6.54 (s, 2 H) 7.17 (dd, 1 H) 7.24 (d, 1 H); MS (ES+) m/z 376 [M+H]⁺.

Example 8

(1r,4r)-4-Methoxy-5"-methyl-6'-(3-methylbut-1-yn-1-yl)-3'H-dispiro[cyclohexane-1,2'-indene-1',2"-imidazol]-4"-amine

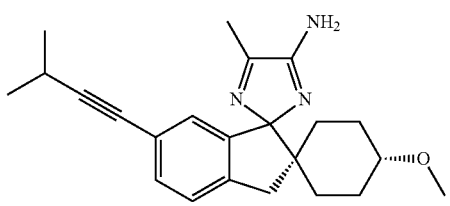

To a solution of (1r,4r)-6'-bromo-4-methoxy-5"-methyl-3'H-dispiro[cyclohexane-1,2'-indene-1',2"-imidazol]-4"-amine (Intermediate 8, isomeric mixture 2, Method B, 0.153 g, 0.41 mmol) in DMF (8 mL) under argon was added 3-methylbut-1-yne (0.028 g, 0.41 mmol), tetrakis(triphenylphosphine)palladium(0) (0.047 g, 0.04 mmol) and triethylamine (1.70 mL, 12.2 mmol). The reaction mixture was stirred at r.t. for 5 min, then cuprous iodide (0.012 g, 0.06 mmol) was added and the reaction mixture was heated at 65° C. for 18 h. The reaction mixture was partitioned between brine and EtOAc. The organic phase was dried over MgSO₄ and concentrated in vacuo. The residue was purified by preparative HPLC to give the title compound (35 mg, 24% yield): ¹H NMR (500 MHz, DMSO-d₆) δ ppm 0.87-0.98 (m, 1 H), 1.09-1.26 (m, 8 H), 1.35-1.48 (m, 3 H), 1.81 (d, 2 H), 2.15 (s, 3 H), 2.73 (dt, 1 H), 2.88-3.08 (m, 3 H), 3.18 (s, 3 H), 6.49 (s, 1 H), 6.54 (s, 2 H), 7.15 (dd, 1 H), 7.24 (d, 1 H); MS (ES+) m/z 364 [M+H]⁺.

Example 9

Separation of the isomers of (1r,4r)-4-methoxy-5"-methyl-6'-(3-methylbut-1-yn-1-yl)-3'H-dispiro[cyclohexane-1,2'-indene-1',2"-imidazol]-4"-amine The enantiomers of (1r,4r)-4-methoxy-5"-methyl-6'-(3-methylbut-1-yn-1-yl)-3'H-dispiro[cyclohexane-1,2'-indene-1',2"-imidazol]-4"-amine (Example 11, 0.017 g) were separated using a SFC Berger Multigram II system, with a LuxC4; 20*250 mm; 5 μm column, and a mobile phase consisting of 20% MeOH (containing 0.1% DEA) and 80% CO₂ at a flow rate of 50 mL/min, to give:
Isomer 1 (1r,1'R,4R)-4-methoxy-5"-methyl-6'43-methylbut-1-yn-1-yl)-3'H-dispiro[cyclohexane-1,2'-indene-1',2"-imidazol]-4"-amine (7.1 mg, 42% yield).

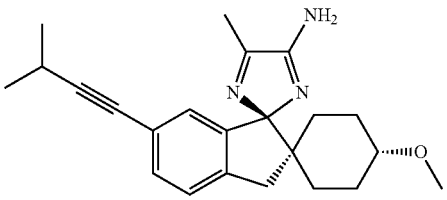 [SMILES: CO[C@H]1CC[C@]2(CC1)Cc1ccc(C#CC(C)C)cc1[C@@]21N=C(C)C(N)=N1]

MS (ES+) m/z 364 (M+H)+. ¹H NMR (500 MHz, DMSO-d₆) δ ppm 0.92 (td, 1 H) 1.08-1.28 (m, 8 H) 1.33-1.49 (m, 3 H) 1.81 (d, 2 H) 2.15 (s, 3 H) 2.73 (dt, 1 H) 2.88-3.06 (m, 3 H) 3.16 (d, 1 H) 3.18 (s, 3 H) 6.49 (s, 1 H) 6.54 (br. s., 2 H) 7.15 (dd, 1 H) 7.24 (d, 1 H).
and Isomer 2 (1r,1'S,4S)-4-methoxy-5"-methyl-6'43-methylbut-1-yn-1-yl)-3'H-dispiro[cyclohexane-1,2'-indene-1',2"-imidazol]-4"-amine (6.6 mg, 39% yield).

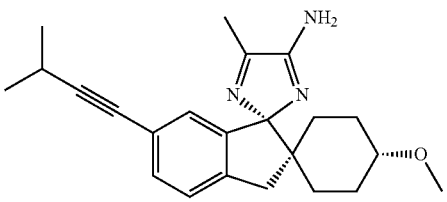 [SMILES: CO[C@H]1CC[C@]2(CC1)Cc1ccc(C#CC(C)C)cc1[C@]21N=C(C)C(N)=N1]

MS (ES+) m/z 364 (M+H)+. ¹H NMR (500 MHz, DMSO-d₆) δ ppm 0.92 (td, 1 H) 1.09-1.30 (m, 9 H) 1.34-1.49 (m, 3 H)

1.81 (d, 2 H) 2.15 (s, 3 H) 2.73 (dt, 1 H) 2.86-3.08 (m, 3 H) 3.16 (d, 0 H) 3.18 (s, 3 H) 6.49 (s, 1 H) 6.54 (br. s., 2 H) 7.15 (dd, 1 H) 7.24 (d, 1 H)

Example 10

(1r,4r)-4-Methoxy-5"-methyl-6'-(3,3,3-trifluoropropoxy)-3'H-dispiro[cyclohexane-1,2'-indene-1',2"-imidazol]-4"-amine

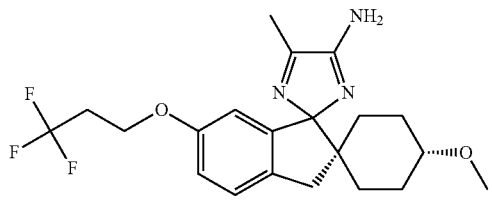

Method A (1r,4r)-4-Methoxy-5"-methyl-6'-(3,3,3-trifluoropropoxy)-3'H-dispiro[cyclohexane-1,2'-indene-1',2"-imidazole]-4"(3"H)-thione (Intermediate 40, 175 mg, 0.41 mmol) and ammonia (7 M in MeOH, 3 mL, 21 mmol) were mixed in a MW vial. The vial was sealed and the reaction was heated at 110° C. for 30 min in a MW reactor. The mixture was concentrated in vacuo and the residue was dissolved in ammonia (7 M in MeOH, 3 mL, 21 mmol) and heated at 110° C. for 30 min in a MW reactor. This procedure (concentration, addition of ammonia and heating) was repeated twice (4 runs in total). After evaporation of the solvent, the residue was partitioned between EtOAc and 2 M aq. citric acid. The phases were separated and the organic layer was extracted with 2 M aq. citric acid. The organic layer was discarded while the combined aqueous phases were basified to pH 12 by addition of 50% aq. NaOH. The product was extracted with EtOAc (twice). The combined organic layers were treated with charcoal and filtered through diatomaceous earth. The filter pad was rinsed with EtOAc and the filtrate was concentrated in vacuo. Purification by preparative HPLC afforded 64 mg (38% yield) of the title compound: $^1$H NMR (500 MHz, DMSO-$d_6$) δ ppm 0.90 (td, 1 H), 1.08-1.27 (m, 2 H), 1.34-1.49 (m, 3 H), 1.80 (d, 2 H), 2.15 (s, 3 H), 2.69 (tt, 2 H), 2.82-2.99 (m, 3 H), 3.15-3.22 (m, 3 H), 4.00-4.10 (m, 2 H), 6.08 (d, 1 H), 6.51 (br. s., 2 H), 6.75 (dd, 1 H), 7.18 (d, 1 H); MS (APCI+) m/z 410 [M+H]$^+$.

Method B

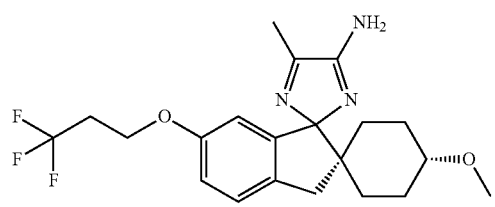

Tert-butyl [(1r,4r)-6'-bromo-4-methoxy-5"-methyl-3'H-dispiro[cyclohexane-1,2'-indene-1',2"-imidazol]-4"-yl]carbamate (Intermediate 12, 715 mg, 1.50 mmol), allylpalladium(II) chloride (21.95 mg, 0.06 mmol), di-tert-butyl(2',4',6'-triisopropyl-3-methoxy-6-methylbiphenyl-2-yl)phosphine (70.3 mg, 0.15 mmol) and Cs$_2$CO$_3$ (733 mg, 2.25 mmol) were placed in a MW-vial. Toluene (8 mL) was added and the head space was evacuated and refilled with argon. 3,3,3-Trifluoropropan-1-ol (684 mg, 6.00 mmol) was added and the mixture was heated to 100° C. in a MW apparatus for 2 h. 2 M methanolic ammonia (8.57 mL, 60.0 mmol) and water (1.08 mL, 60.0 mmol) was added and the mixture was heated to 80° C. for 12 h. The reaction mixture was cooled to r.t. The organic solvents were evaporated and the aqueous residue was extracted with DCM. The combined extracts were concentrated and the residue was purified by reverse phase preparative chromatography providing the title compound (410 mg, 67% yield). $^1$H NMR (500 MHz, DMSO-$d_6$) δ 0.90 (td, 1 H), 1.08-1.27 (m, 2 H), 1.34-1.49 (m, 3 H), 1.80 (d, 2H), 2.15 (s, 3 H), 2.69 (tt, 2 H), 2.82-2.99 (m, 3 H), 3.15-3.22 (m, 3 H), 4.00-4.10 (m, 2 H), 6.08 (d, 1 H), 6.51 (br. s., 2 H), 6.75 (dd, 1 H), 7.18 (d, 1 H); MS (APCI+) m/z 410 [M+H]$^+$.

Example 11

Separation of the enantiomers of (1r,4r)-4-methoxy-5"-methyl-6'-(3,3,3-trifluoropropoxy)-3'H-dispiro[cyclohexane-1,2'-indene-1',2"-imidazol]-4"-amine (1r,4r)-4-Methoxy-5"-methyl-6'-(3,3,3-trifluoropropoxy)-3'H-dispiro[cyclohexane-1,2'-indene-1',2"-imidazol]-4"-amine (Example 10, 56 mg, 0.14 mmol) was separated into the enantiomers on a SFC Berger Multigram II system equipped with a LuxC4; 4.6*250 mm; 5 μm column and a mobile phase of 20% MeOH (containing 0.1% DEA) and 80% CO$_2$ at a flow rate of 50 mL/min to give:

Isomer 1 (1r,1'R,4R)-4-Methoxy-5"-methyl-6'-(3,3,3-trifluoropropoxy)-3'H-dispiro[cyclohexane-1,2'-indene-1',2"-imidazol]-4"-amine as the first enantiomer to elute with retention time 2.9 min (23 mg, 41% yield).

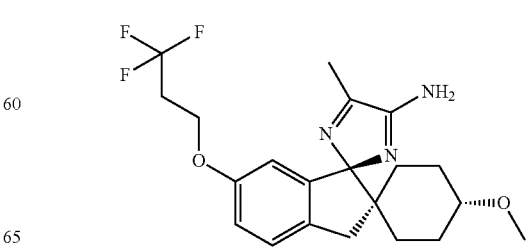

$^1$H NMR (500 MHz, DMSO-$d_6$) δ ppm 0.91 (br. s., 1 H) 1.14 (d, 2 H) 1.37-1.46 (m, 3 H) 1.80 (d, 2 H) 2.15 (s, 3 H) 2.69 (dt, 2 H) 2.83-2.99 (m, 3 H) 3.18 (s, 3 H) 4.02-4.08 (m, 2 H) 6.08 (br. s., 1 H) 6.51 (br. s., 2 H) 6.75 (d, 1 H) 7.18 (d, 1 H); MS (APCI+) m/z 410 [M+H]$^+$.

and Isomer 2 (1r,1'S,4S)-4-Methoxy-5"-methyl-6'-(3,3,3-trifluoropropoxy)-3'H-dispiro[cyclohexane-1,2'-indene-1',2"-imidazol]-4"-amine as the second eluting isomer with retention time 4.2 min (23 mg, 41% yield).

¹H NMR (500 MHz, DMSO-d₆) δ ppm 0.92 (dd, 1 H) 1.18 (m, 2 H) 1.41 (m, 3 H) 1.80 (d, 2 H) 2.15 (s, 3 H) 2.69 (tt, 2H) 2.91 (m, 3 H) 3.18 (s, 3 H) 4.05 (td, 2 H) 6.08 (d, 1 H) 6.51 (br. s., 2 H) 6.75 (dd, 1 H) 7.18 (d, 1 H); MS (ES+) m/z 410 [M+H]⁺.

Example 12

(1r,4r)-4-(Difluoromethoxy)-6'-(3-fluoropropoxy)-5"-methyl-3'H-dispiro[cyclohexane-1,2'-indene-1',2"-imidazol]-4"-amine

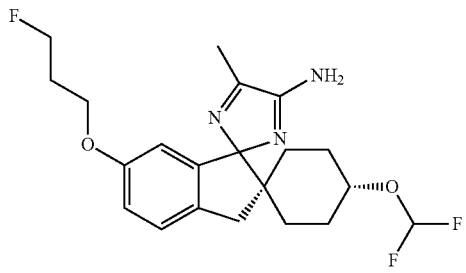

6'-(3-Fluoropropoxy)-4-hydroxy-5"-methyl-3'H-dispiro[cyclohexane-1,2'-indene-1',2"-imidazole]-4"(3"H)-thione (Intermediate 33, 290 mg, 0.77 mmol) was suspended in dry acetonitrile (10 mL). Cuprous iodide (14.67 mg, 0.08 mmol) was added and the resulting mixture was heated at 60° C. for 5 min under an atmosphere of argon. 2-(Fluorosulphonyl)difluoroacetic acid (0.127 mL, 1.16 mmol) was added in a stream and the reaction mixture was heated for 20 min. Additional 2-(Fluorosulphonyl)difluoroacetic acid (0.042 mL, 0.39 mmol) was added, and the mixture was heated for an additional 45 min. The mixture was cooled to r.t. Water and EtOAc were added, and the phases were separated and the aqueous phase was re-extracted with EtOAc twice. The combined organic phases were dried using a phase separator and concentrated to give 340 mg of 4-(difluoromethoxy)-6'-(3-fluoropropoxy)-5"-methyl-3'H-dispiro[cyclohexane-1,2'-indene-1',2"-imidazole]-4"(3"H)-thione, which was suspended in ammonia (7 M in methanol, 4 mL, 28 mmol), and heated in the MW at 100° C. for 60 min. The mixture was concentrated, re-dissolved in ammonia (7 M in methanol, 4 mL, 28 mmol) and heated at 100° C. for 60 min. This procedure was repeated eight times in total. The mixture was cooled to r.t., concentrated, and purified by flash column chromatography using a gradient of 0-50% EtOAc in heptane, followed by 0-20% MeOH (containing 1% NH₃) in EtOAc, to give 82 mg (25% yield) of the title compound. MS (MM-ES+APCI)+m/z 410.2 [M+H]⁺.

Example 13

Separation of the enantiomers of (1r,4r)-4-(Difluoromethoxy)-6'-(3-fluoropropoxy)-5"-methyl-3'H-dispiro[cyclohexane-1,2'-indene-1',2"-imidazol]-4"-amine (1r,4r)-4-(Difluoromethoxy)-6'-(3-fluoropropoxy)-5"-methyl-3'H-dispiro[cyclohexane-1,2'-indene-1',2"-imidazol]-4"-amine (Example 12, 82 mg, 0.20 mmol) was subjected to chiral separation on a SFC Berger Multigram II system with a LuxC4; 20*250 mm; 5 µm column and a mobile phase consisting of 15% MeOH (containing 0.1% DEA) and 85% CO₂ at a flow rate of 50 mL/min to give:

Isomer 1 (1r,1'R,4R)-4-(difluoromethoxy)-6'-(3-fluoropropoxy)-5"-methyl-3'H-dispiro[cyclohexane-1,2'-indene-1',2"-imidazol]-4"-amine as the first eluting isomer with retention time 4.2 min (21 mg, 26% yield).

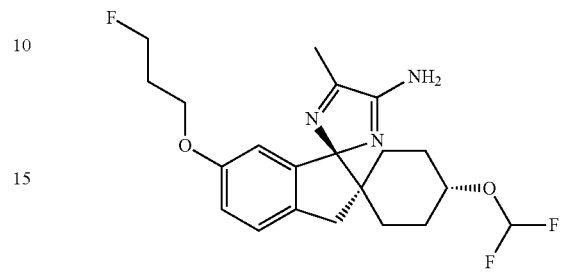

¹H NMR (500 MHz, DMSO-d₆) δ ppm 0.93-1.01 (m, 1 H) 1.36-1.53 (m, 5 H) 1.78 (d, 2 H) 1.97-2.08 (m, 2 H) 2.15 (s, 3 H) 2.88 (d, 1 H) 2.98 (d, 1 H) 3.83-3.88 (m, 1 H) 3.89-3.94 (m, 2 H) 4.51 (t, 1 H) 4.61 (t, 1 H) 6.08 (d, 1 H) 6.53 (s, 2 H) 6.65 (t, 1 H) 6.74 (dd, 1 H) 7.17 (d, 1 H); MS (ES+) m/z 410.12 [M+H]⁺.

and Isomer 2 (1r,1'S,4S)-4-(difluoromethoxy)-6'-(3-fluoropropoxy)-5"-methyl-3'H-dispiro[cyclohexane-1,2'-indene-1',2"-imidazol]-4"-amine as the second eluting isomer with retention time 5.7 min (24 mg, 29% yield).

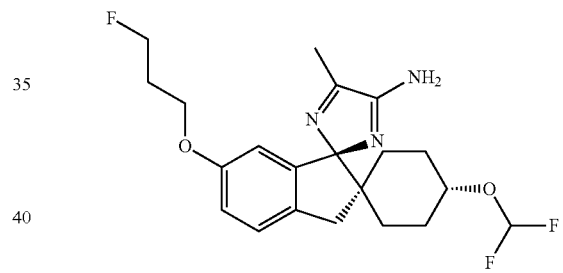

¹H NMR (500 MHz, DMSO-d₆) δ ppm 0.93-1.01 (m, 1 H) 1.36-1.53 (m, 5 H) 1.78 (d, 2 H) 1.97-2.08 (m, 2 H) 2.15 (s, 3 H) 2.88 (d, 1 H) 2.98 (d, 1 H) 3.83-3.88 (m, 1 H) 3.89-3.94 (m, 2 H) 4.51 (t, 1 H) 4.61 (t, 1 H) 6.08 (d, 1 H) 6.53 (s, 2 H) 6.65 (t, 1 H) 6.74 (dd, 1 H) 7.17 (d, 1 H); MS (ES+) m/z 410.12 [M+H]⁺.

Example 14

(1r,4r)-6'-(2-Fluoropropoxy)-4-methoxy-5"-methyl-3'H-dispiro[cyclohexane-1,2'-indene-1',2"-imidazol]-4"-amine

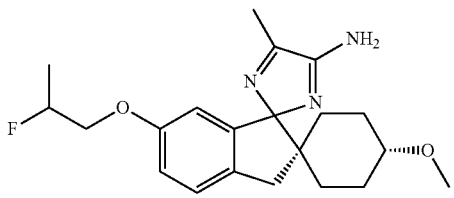

A 1:1 mixture of di-tert-butyl [(1r,4r)-6'-bromo-4-methoxy-5"-methyl-3'H-dispiro[cyclohexane-1,2'-indene-1',2"-imidazol]-4"-yl]imidodicarbonate and tert-butyl [(1r,4r)-6'-bromo-4-methoxy-5"-methyl-3'H-dispiro[cyclohexane-1,2'-indene-1',2"-imidazol]-4"-yl]carbamate (prepared as for Intermediate 12, but without the chromatographic separation, 154 mg, 0.30 mmol), allylpalladium chloride dimer (4.26 mg, 0.01 mmol), di-tert-butyl(2',4',6'-triisopropyl-3-methoxy-6-methylbiphenyl-2-yl)phosphine (16.39 mg, 0.03 mmol) and $Cs_2CO_3$ (142 mg, 0.44 mmol) were placed in a tube. Toluene (1 mL) was added. The tube was capped and the headspace was evacuated and refilled with argon. 2-Fluoropropan-1-ol (114 mg, 1.46 mmol) was added and the mixture was heated to 100° C. for 1.5 h. The reaction mixture was filtered and 7 M methanolic ammonia (0.84 mL, 5.9 mmol) was added and the resulting mixture was heated to 100° C. in a MW reactor for 1.5 h. Water (0.1 mL, 5.9 mmol) was added and the mixture was heated again to 100° C. by MWs for 2 h. The solution was concentrated and purified by prep HPLC to give the title product (27 mg, 25% yield). $^1$H NMR (500 MHz, DMSO-$d_6$) δ ppm 0.85-0.96 (m, 1 H), 1.08-1.26 (m, 2 H), 1.27-1.36 (m, 3 H), 1.36-1.47 (m, 3 H), 1.80 (m, 2H), 2.15 (s, 3 H), 2.81-2.89 (m, 1 H), 2.89-2.99 (m, 2 H), 3.18 (s, 3 H), 3.82-4.05 (m, 2 H), 4.83-5.01 (m, 1 H), 6.06-6.12 (m, 1 H), 6.51 (br. s., 2 H), 6.74 (d, 1 H), 7.17 (d, 1 H); MS (ES+) m/z 374 [M+1-1]$^+$.

Example 15

3-[(1r,1'R,4R)-4"-amino-4-hydroxy-5"-methyl-3'H-dispiro[cyclohexane-1,2'-indene-1',2"-imidazol]-6'-yl]-5-chlorobenzonitrile and 3-[(1r,1'S,4S)-4"-amino-4-hydroxy-5"-methyl-3'H-dispiro[cyclohexane-1,2'-indene-1',2"-imidazol]-6'-yl]-5-chlorobenzonitrile (1r,4r)-4"-Amino-6'-bromo-5"-methyl-3'H-dispiro[cyclohexane-1,2'-indene-1',2"-imidazol]-4-ol (Example 3, 0.516 g, 1.42 mmol), 3-chloro-5-cyanophenylboronic acid (Intermediate 23, 0.310 g, 1.71 mmol), 3-(di-tert-butylphosphonium)propane sulfonate (0.038 g, 0.14 mmol), sodium tetrachloropalladate(II) (0.021 g, 0.07 mmol), 2-MeTHF (16 mL) and aq. potassium carbonate (2.0 M, 2.14 mL, 4.27 mmol) were added to MW vial. The vial was heated in the mw for 30 min at 130° C. The reaction mixture was cooled to r.t. EtOAc and water were added, and the organic phase was collected. 0.1 M aq. citric acid was added to the organic phase. The citric acid phase was washed with ethyl acetate and then basified with 1 M aq. NaOH and extracted with DCM. The organic phase was dried through a phase separator and evaporated to dryness. The residue was purified by two consecutive column chromatography steps. First with 0-100% (5% MeOH in EtOAc) in heptane and then with (0.2 M $NH_3$ in MeOH) in DCM as eluent. The product was subjected to chiral separation using a SFC Berger Multigram II system with a LuxC4; 20*250 mm; 5 μm column and a mobile phase consisting of 40% MeOH (containing 0.1% DEA) and 60% $CO_2$ at a flow rate of 50 mL/min to give:

Isomer 1 3-[(1r,1'R,4R)-4"-amino-4-hydroxy-5"-methyl-3'H-dispiro[cyclohexane-1,2'-indene-1',2"-imidazol]-6'-yl]-5-chlorobenzonitrile with retention time 3.16 min (95 mg, 16% yield):

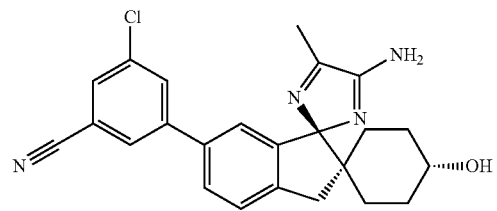 [SMILES: CC1=N[C@]2(N=C1N)c1cc(-c3cc(Cl)cc(C#N)c3)ccc1C[C@]21CC[C@@H](O)CC1]

$^1$H NMR (500 MHz, CDCl$_3$) δ ppm 1.14 (td, 1 H), 1.39-1.58 (m, 4 H), 1.64-1.73 (m, 2 H), 1.83-1.93 (m, 2 H), 2.34 (s, 3 H), 3.17-3.30 (m, 2 H), 3.51-3.61 (m, 1 H), 4.83 (br. s., 1 H), 6.85-6.90 (m, 1 H), 7.37-7.46 (m, 2 H), 7.52-7.56 (m, 1 H), 7.65-7.69 (m, 1 H), 7.71 (t, 1 H) MS (MM-ES+APCI)+ m/z 419 [M+H]$^+$.

and Isomer 2 3-[(1r,1'S,4S)-4"-amino-4-hydroxy-5"-methyl-3'H-dispiro[cyclohexane-1,2'-indene-1',2"-imidazol]-6'-yl]-5-chlorobenzonitrile with retention time 5.77 min (60 mg, 10% yield):

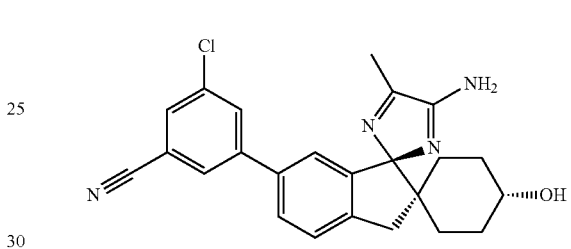

$^1$H NMR (500 MHz, CDCl$_3$) δ ppm 1.14 (td, 1 H), 1.39-1.58 (m, 4 H), 1.64-1.73 (m, 2 H), 1.83-1.93 (m, 2 H), 2.34 (s, 3 H), 3.17-3.30 (m, 2 H), 3.51-3.61 (m, 1 H), 4.83 (br. s., 1 H), 6.85-6.90 (m, 1 H), 7.37-7.46 (m, 2 H), 7.52-7.56 (m, 1 H), 7.65-7.69 (m, 1 H), 7.71 (t, 1 H) MS (MM-ES+APCI)+ m/z 419 [M+H]$^+$.

Example 16

(1r,4r)-6'-Bromo-5"-methyl-4-(propan-2-yloxy)-3'H-dispiro[cyclohexane-1,2'-indene-1',2"-imidazol]-4"-amine

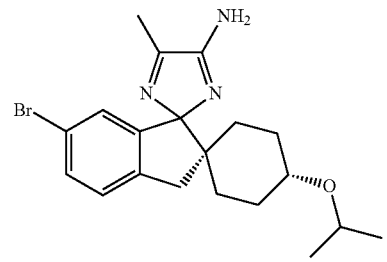

The title compound (154 mg, 70% yield) was prepared using the procedure described for Example 1, starting from (1r,4r)-6'-bromo-5"-methyl-4-(propan-2-yloxy)-3'H-dispiro[cyclohexane-1,2'-indene-1',2"-imidazole]-4"(3"H)-thione (Intermediate 36, 229 mg, 0.54 mmol). $^1$H NMR (500 MHz, DMSO-$d_6$) δ ppm 0.96 (m, 1 H), 1.02 (d, 6 H), 1.10-1.30 (m, 2 H), 1.35-1.45 (m, 3 H), 1.65-1.77 (m, 2 H), 2.16 (s, 3 H), 2.89 (d, 1 H), 3.01 (d, 1 H), 3.10 (m, 1 H), 3.63 (spt, 1 H), 6.57 (s, 2 H), 6.64 (d, 1 H), 7.25 (d, 1 H), 7.34 (dd, 1 H); MS (ES+) m/z 404.0 [M+H]$^+$.

Example 17

(1r,4r)-6'-(3-Fluoropropoxy)-5"-methyl-4-(propan-2-yloxy)-3'H-dispiro[cyclohexane-1,2'-indene-1',2"-imidazol]-4"-amine

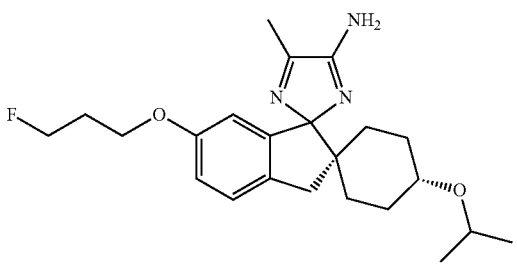

The head space above a mixture of di-tert-butyl(2',4',6'-triisopropyl-3-methoxy-6-methylbiphenyl-2-yl)phosphine (8.5 mg, 0.02 mmol), allylpalladium chloride dimer (2.2 mg, 6.05 µmol), cesium carbonate (148 mg, 0.45 mmol) and 3-fluoropropan-1-ol (45 µL, 0.60 mmol) was evacuated and refilled with argon. A degassed solution of di-tert-butyl [(1r,4r)-6'-bromo-5"-methyl-4-(propan-2-yloxy)-3'H-dispiro[cyclohexane-1,2'-indene-1',2"-imidazol]-4"-yl]imidodicarbonate (Intermediate 37, 183 mg, 0.30 mmol) in dry toluene (1.3 mL) was added and the mixture was heated at 90° C. overnight. The reaction mixture was filtered through a syringe filter which was washed with toluene (0.3 mL), the solution was added to a degassed mixture of 3-fluoropropan-1-ol (45.5 µL, 0.61 mmol), allylpalladium chloride dimer (4.4 mg, 0.01 mmol), di-tert-butyl(2',4',6'-triisopropyl-3-methoxy-6-methylbiphenyl-2-yl)phosphine (17.0 mg, 0.04 mmol) and cesium carbonate (148 mg, 0.45 mmol) and the heating was resumed for 18 h. After cooling the reaction mixture was filtered through a syringe filter. The filter was washed with 7 M ammonia in methanol (1.4 mL, 9.80 mmol). More 7 M ammonia in methanol (1.4 mL, 9.8 mmol) was added to the solution obtained after the filtration and the mixture was heated at 85° C. for nine days. After 5 days at r.t. the mixture was filtered through a syringe filter and concentrated. Purification by flash silica gel chromatography using a gradient of CHCl$_3$/MeOH (20:1-15:1) and then preparative HPLC gave the title compound (34 mg, 28% yield). $^1$H NMR (500 MHz, DMSO-d$_6$) δ ppm 0.91 (td, 1 H), 1.02 (d, 6 H), 1.10-1.28 (m, 2 H), 1.41 (d, 3 H), 1.70 (br. s., 2 H), 1.95-2.09 (m, 2 H), 2.11-2.18 (m, 3 H), 2.85 (d, 1 H), 2.95 (d, 1 H), 3.05-3.15 (m, 1 H), 3.63 (spt, 1 H), 3.85-3.96 (m, 2 H), 4.51 (t, 1 H), 4.61 (t, 1 H), 6.07 (d, 1 H), 6.49 (s, 2 H), 6.73 (dd, 1 H), 7.16 (d, 1 H); MS (ES+) m/z 402.1 [M+H]$^+$.

Example 18

(1r,4r)-6'-[(2S)-Butan-2-yloxy]-4-methoxy-5"-methyl-3'H-dispiro[cyclohexane-1,2'-indene-1',2"-imidazol]-4"-amine

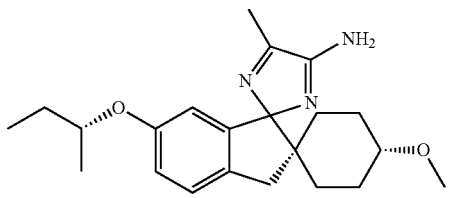

The title compound was prepared following the procedure described for Example 3, starting from di-tert-butyl [(1r,4r)-6'-bromo-4-methoxy-5"-methyl-3'H-dispiro[cyclohexane-1,2'-indene-1',2"-imidazol]-4"-yl]imidodicarbonate (Intermediate 12, 0.300 g, 0.52 mmol), and (S)-butan-2-ol (0.096 mL, 1.04 mmol). Purification by reverse phase preparative chromatography afforded the title compound (15 mg, 7% yield). $^1$H NMR (500 MHz, DMSO-d$_6$) δ ppm 0.87 (t, 3 H) 0.90 (m, 1 H) 1.12 (d, 4 H) 1.19 (m, 2 H) 1.43 (m, 4 H) 1.52 (m, 2 H) 1.80 (d, 2 H) 2.14 (d, 3 H) 2.90 (m, 3 H) 3.18 (s, 3 H) 4.17 (m, 1 H) 6.03 (d, 1 H) 6.50 (d, 2 H) 6.69 (dd, 1 H) 7.14 (d, 1 H); MS (APCI+) m/z 370 [M+H]$^+$.

Example 19

(1r,1'R,4R)-4"-Amino-4-methoxy-5"-methyl-3'H-dispiro[cyclohexane-1,2'-indene-1',2"-imidazol]-6'-ol

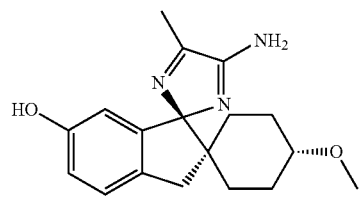 [SMILES: CO[C@H]1CC[C@]2(CC1)Cc1ccc(O)cc1[C@@]21N=C(C)C(N)=N1]

(1r,1'R,4R)-6'-bromo-4-methoxy-5"-methyl-3'H-dispiro[cyclohexane-1,2'-indene-1',2"-imidazol]-4"-amine (Intermediate 8, isomer 1), 300 mg, 0.80 mmol), 4,4,4',4',5,5,5',5'-octamethyl-2,2'-bi(1,3,2-dioxaborolane) (0.253 g, 1.00 mmol), PdCl$_2$(dppf)-CH$_2$Cl$_2$ adduct (0.065 g, 0.08 mmol) and potassium acetate (0.235 g, 2.39 mmol) were weighed into a MW tube. 2-Me THF (4 mL) was added and the head space was evacuated and refilled with nitrogen. The mixture was heated at 100° C. in a MW reactor for 1.5 h. The mixture was diluted with EtOAc and passed through a short plug of silica that was then rinsed with 10% MeOH (containing 0.1 M NH$_3$) in dichloromethane. The solvent was evaporated. The residue was dissolved in EtOAc and filtered through a short diatomaceous earth plug and then concentrated. To the solution of the product in THF (15 mL) were added hydrogen peroxide (0.816 mL, 7.98 mmol) and acetic acid (2 mL, 35 mmol). The resulting mixture was stirred overnight. The reaction mixture was diluted with EtOAc and washed with saturated aqueous NaHCO$_3$, water and brine and dried over Na$_2$SO$_4$ and concentrated. The aq. phase was set to pH 10 and extracted several times with EtOAc. The combined organic layers were dried over Na$_2$SO$_4$ and concentrated. Purification by reversed phase column chromatography afforded 119 mg (47% yield) of the title compound. $^1$H NMR (500 MHz, DMSO-d$_6$) δ ppm 0.88 (m, 1 H), 1.17 (m, 2 H), 1.41 (m, 3 H), 1.79 (d, 2 H), 2.13 (s, 3 H), 2.88 (m, 3 H), 3.17 (m, 3 H), 5.96 (d, 1 H), 6.48 (br. s., 2 H), 6.53 (dd, 1 H), 7.02 (d, 1 H), 9.00 (m, 1 H); MS (ES+) m/z 314 [M+H]$^+$.

Example 20

(1r,4r)-4''-amino-5''-methyl-6'-[5-(prop-1-yn-1-yl)pyridin-3-yl]-3'H-dispiro[cyclohexane-1,2'-indene-1',2''-imidazol]-4-ol

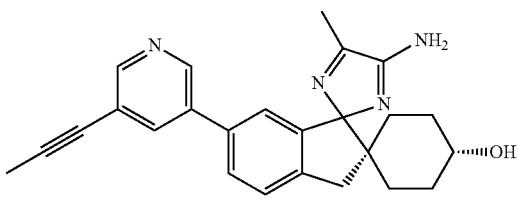

5-(Prop-1-ynyl)pyridin-3-ylboronic acid (Intermediate 25, 0.467 g, 2.90 mmol), (1r,4r)-4''-amino-6'-bromo-5''-methyl-3'H-dispiro[cyclohexane-1,2'-indene-1',2''-imidazol]-4-ol (Example 4, 0.875 g, 2.42 mmol), 3-(di-tert-butylphosphonium)propane sulfonate (0.130 g, 0.48 mmol), sodium tetrachloropalladate(II) (0.071 g, 0.24 mmol), and aq. potassium carbonate (2 M, 3.62 mL, 7.25 mmol), were mixed in 2-Me THF (10 mL) in a MW vial. The atmosphere was exchanged to argon. The vial was placed in a MW reactor, and heated to 120° C. for 40 min. The reaction mixture was cooled to r.t. The mixture was combined with another batch started from 0.725 g, (2.00 mmol) of (1r,4r)-4''-amino-6'-bromo-5''-methyl-3'H-dispiro[cyclohexane-1,2'-indene-1',2''-imidazol]-4-ol, diluted with EtOAc, and washed with brine. The organic layer was extracted with EtOAc. The organic layers were combined, dried over MgSO$_4$, filtered, and concentrated to yield a residue. The residue was purified by column chromatography using DCM/MeOH 80/20 as eluent, providing 0.970 g (55% yield) of the title compound. MS (ES+) 399 [M+H]$^+$

Example 21

Separation of the enantiomers of (1r,4r)-4''-amino-5''-methyl-6'-[5-(prop-1-yn-1-yl)pyridin-3-yl]-3'H-dispiro[cyclohexane-1,2'-indene-1',2''-imidazol]-4-ol (1r,4r)-4''-Amino-5''-methyl-6'-[5-(prop-1-yn-1-yl)pyridin-3-yl]-3'H-dispiro[cyclohexane-1,2'-indene-1',2''-imidazol]-4-ol (Example 20, 970 mg, 2.73 mmol) was subjected to chiral separation using a SFC Berger Multigram II system with a OD-H; 20*250 mm; 5 μm column and a mobile phase consisting of 30% MeOH (containing 0.1% DEA) and 70% CO$_2$ at a flow rate of 50 mL/min. 50 mg dissolved in MeOH (1.8 mL) was injected each time to give:
Isomer 1 (1r,1'R,4R)-4''-Amino-5''-methyl-6'-[5-(prop-1-yn-1-yl)pyridin-3-yl]-3'H-dispiro[cyclohexane-1,2'-indene-1',2''-imidazol]-4-ol as the first eluting isomer with retention time ~2.5 min (382 mg, 39% yield).

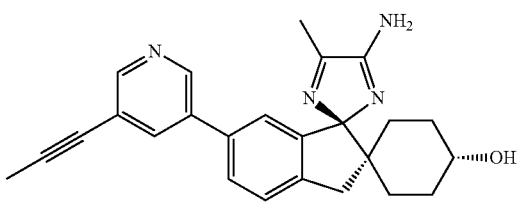 [SMILES: CC#Cc1cncc(-c2ccc3c(c2)[C@@]2(N=C(C)C(N)=N2)[C@]2(CC[C@H](O)CC2)C3)c1]

$^1$H NMR (500 MHz, DMSO-d$_6$) δ ppm 0.89-1.02 (m, 1 H) 1.13-1.35 (m, 2 H) 1.41 (br. s., 3 H) 1.66 (br. s., 2 H) 2.09 (s, 3 H) 2.17 (s, 3 H) 3.04 (dd, 2 H) 3.18-3.27 (m, 1 H) 4.55 (br. s., 1 H) 6.53 (br. s., 2 H) 6.82 (s, 1 H) 7.41 (d, 1 H) 7.53 (dd, 1 H) 7.90 (s, 1 H) 8.51 (d, 1 H) 8.66 (d, 1 H); MS (ES+) m/z 399 [M+H]$^+$.

and Isomer 2 (1r,1'S,4S)-4''-Amino-5''-methyl-6'-[5-(prop-1-yn-1-yl)pyridin-3-yl]-3'H-dispiro[cyclohexane-1,2'-indene-1',2''-imidazol]-4-ol as the second eluting isomer with retention time ~8.5 min (355 mg, 36% yield).

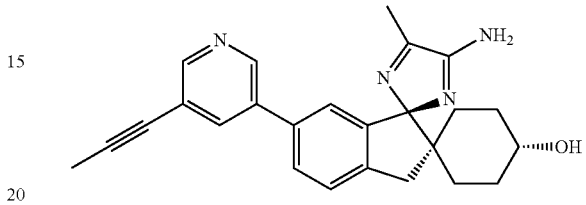

$^1$H NMR (500 MHz, DMSO-d$_6$) δ ppm 0.91-0.96 (m, 1 H) 1.17-1.33 (m, 2 H) 1.38-1.45 (m, 3 H) 1.61-1.70 (m, 2 H) 2.09 (s, 3 H) 2.16 (s, 3 H) 2.99 (d, 1 H) 3.09 (d, 1 H) 3.18-3.26 (m, 1 H) 4.47 (br. s., 1 H) 6.52 (s, 2 H) 6.82 (d, 1 H) 7.41 (d, 1 H) 7.53 (dd, 1 H) 7.90 (t, 1 H) 8.51 (d, 1 H) 8.67 (d, 1 H); MS (APCI+) m/z 399.2 [M+H]$^+$.

Biological Assays

The level of activity of the compounds was tested using the following methods:

TR-FRET Assay

The β-secretase enzyme used in the TR-FRET is prepared as follows:

The cDNA for the soluble part of the human β-Secretase (AA 1-AA 460) was cloned using the ASP2-Fc10-1-IRES-GFP-neoK mammalian expression vector. The gene was fused to the Fc domain of IgG1 (affinity tag) and stably cloned into HEK 293 cells. Purified sBACE-Fc was stored in −80° C. in 50 mM Glycine pH 2.5, adjusted to pH 7.4 with 1 M Tris and had a purity of 40%.

The enzyme (truncated form) was diluted to 6 μg/mL (stock 1.3 mg/mL) and the TruPoint BACE1 Substrate to 200 nM (stock 120 μM) in reaction buffer (NaAcetate, chaps, triton x-100, EDTA pH4.5). Enzyme and compound in dimethylsulphoxide (final DMSO concentration 5%) was mixed and pre-incubated for 10 minutes at RT. Substrate was then added and the reaction was incubated for 15 minutes at RT. The reaction was stopped with the addition of 0.35 vol Stop solution (NaAcetate, pH 9). The fluorescence of the product was measured on a Victor II plate reader with excitation wavelengths of 340-485 nm and emission wavelengths of 590-615 nm. The final concentration of the enzyme was 2.7 μg/ml; the final concentration of substrate was 100 nM (Km of ~250 nM). The dimethylsulphoxide control, instead of test compound, defined the 100% activity level and 0% activity was defined by wells lacking enzyme (replaced with reaction buffer) or by a saturating dose of a known inhibitor, 2-amino-6-[3-(3-methoxyphenyl)phenyl]-3,6-dimethyl-5H-pyrimidin-4-one. A control inhibitor was also used in dose response assays and had an IC50 of ~150 nM.

Diluted TR-FRET Assay

Compounds with a high affinity were further tested in a diluted TR-FRET assay, conditions as described above for the TR-FRET assay, but with 50 times less enzyme and a 6.5 h long reaction time at r.t. in the dark.

sAPPβ Release Assay

SH-SY5Y cells were cultured in DMEM/F-12 with Glutamax, 10% FCS and 1% non-essential amino acids and cryopreserved and stored at −140° C. at a concentration of 7.5-9.5×10$^6$ cells per vial. Thaw cells and seed at a conc. of around 10000 cells/well in DMEM/F-12 with Glutamax, 10% FCS and 1% non-essential amino acids to a 384-well tissue culture treated plate, 100 µL cell susp/well. The cell plates were then incubated for 7-24 h at 37° C., 5% CO$_2$. The cell medium was removed, followed by addition of 30 µL compound diluted in DMEM/F-12 with Glutamax, 10% FCS, 1% non-essential amino acids and 1% PeSt to a final conc. of 1% DMSO. The compounds were incubated with the cells for 17 h (overnight) at 37° C., 5% CO$_2$. Meso Scale Discovery (MSD) plates were used for the detection of sAPPβ release. MSD sAPPβ plates were blocked in 1% BSA in Tris wash buffer (40 µL/well) for 1 h on shake at r.t. and washed 1 time in Tris wash buffer (40 µL/well). 20 µL of medium was transferred to the pre-blocked and washed MSD sAPPβ microplates, and the cell plates were further used in an ATP assay to measure cytotoxicity. The MSD plates were incubated with shaking at r.t. for 2 h and the media discarded. 10 µL detection antibody was added (1 nM) per well followed by incubation with shaking at r.t. for 2 h and then discarded. 40 µL Read Buffer was added per well and the plates were read in a SECTOR Imager.

ATP Assay

As indicated in the sAPPβ release assay, after transferring 20 µL medium from the cell plates for sAPPβ detection, the plates were used to analyse cytotoxicity using the ViaLight™ Plus cell proliferation/cytotoxicity kit from Cambrex Bio-Science that measures total cellular ATP. The assay was performed according to the manufacture's protocol. Briefly, 10 µL cell lysis reagent was added per well. The plates were incubated at r.t. for 10 min. Two min after addition of 25 µL to reconstituted ViaLight™ Plus ATP reagent, the luminescence was measured. Tox threshold is a signal below 75% of the control.

Results

Typical IC$_{50}$ values for the compounds of the present invention are in the range of about 0.1 to about 100,000 nM. Biological data on particular example compounds is given below in Table 1.

The invention claimed is:

1. A compound selected from the group consisting of:
(1r,4r)-4"-Amino-5"-methyl-6'-(2-methylpropoxy)-3'H-dispiro[cyclohexane-1,2'-indene-1',2"-imidazol]-4-ol;
(1r,1'R,4R)-4"-Amino-5"-methyl-6'-(2-methylpropoxy)-3'H-dispiro[cyclohexane-1,2'-indene-1',2"-imidazol]-4-ol;
(1r,1'S,4S)-4"-Amino-5"-methyl-6'-(2-methylpropoxy)-3'H-dispiro[cyclohexane-1,2"-indene-1',2"-imidazol]-4ol;
(1r,4r)-6"-(2,2-Difluoropropoxy)-4-methoxy-5"-methyl-3'H-dispiro[cyclohexane-1,2'-indene-1',2"-imidazol]-4"-amine;
(1r,4r)-4"-Amino-6'-bromo-5"-methyl-3'H-dispiro[cyclohexane-1,2'-indene-1',2"-imidazol]-4-ol;
(1r,1'R,4R)-4"-Amino-6'-bromo-5"-methyl-3'H-dispiro[cyclohexane-1,2'-indene-1',2"-imidazol]-4-ol;
(1r,1'S,4S)-4"-Amino-6'-bromo-5"-methyl-3'H-dispiro[cyclohexane-1,2'-indene-1',2"-imidazol]4-ol;
(1r,1'R,4R)-6'-(Cyclobutylethynyl)-4-methoxy-5"-methyl-3'H-dispiro[cyclohexane-1,2'indene-1',2"-imidazol]-4"-amine;
(1r,1'S,4S)-6'-(Cyclobutylethynyl)-4-methoxy-5"-methyl-3'H-dispiro[cyclohexane-1,2'-indene-1',2"-imidazol]-4"-amine;
(1r,1'R,4R)-4-Methoxy-5"-methyl-6'-(3-methylbut-1-yn-1-yl)-3'H-dispiro[cyclohexane-1,2'-indene-1',2"-imidazol]-4"-amine;
(1r,1'S,4S)-4-Methoxy-5"-methyl-6'-(3-methylbut-1-yn-1-yl)-3'H-dispiro[cyclohexane-1,2'indene-1',2"-imidazol]-4"-amine;
(1r,1'R,4R)-4-Methoxy-5"-methyl-6'-(3,3,3-trifluoropropoxy)-3'H-dispiro[cyclohexane-1,2'-indene-1',2"-imidazol]-4"-amine;
(1r,1'S,4S)-4-Methoxy-5"-methyl-6'-(3,3,3-trifluoropropoxy)-3'H-dispiro[cyclohexane-1,2'-indene-1',2"-imidazol]-4"-amine;
(1r,4r)-4-(Difluoromethoxy)-6'3-fluoropropoxy)-5"-methyl-3'H-dispiro[cyclohexane-1,2'-indene-1',2"-imidazol]-4"-amine;
(1r,1'R,4R)-4-(Difluoromethoxy)-6'-(3-fluoropropoxy)-5"-methyl-3'H-dispiro[cyclohexane-1,2'-indene-1',2"-imidazol]-4"-amine;

TABLE 1

| Example | IC$_{50}$ in TR-FRET assay (nM) | IC$_{50}$ in sAPPβ release assay (nM) | Example | IC$_{50}$ in TR-FRET assay (nM) | IC$_{50}$ in sAPPβ release assay (nM) |
| --- | --- | --- | --- | --- | --- |
| 1 | not tested | not tested | 2, isomer 1 | 13 | not tested |
| 2, isomer 2 | >5000 | not tested | 3 | 6.7$^a$ | 2.4 |
| 4 | not tested | not tested | 5, isomer 1 | 270 | 96 |
| 5, isomer 2 | >4950 | not tested | 6 | 4.2$^a$ | 2.1 |
| 7, isomer 1 | 2.7$^a$ | 2.0 | 7, isomer 2 | 3600 | 678 |
| 8 | 4.7$^a$ | 1.6 | 9, isomer 1 | 1.1$^a$ | 0.7 |
| 9, isomer 2 | 530 | 56 | 10 | 7.5$^a$ | 0.6 |
| 11, isomer 1 | 4.7$^a$ | 0.7 | 11, isomer 2 | 1600 | not tested |
| 12 | not tested | not tested | 13, isomer 1 | 3.0$^a$ | 1.6 |
| 13, isomer 2 | 2900 | not tested | 14 | 6.7$^a$ | 2.5 |
| 15, isomer 1 | 3.2$^a$ | 1.6 | 15, isomer 2 | 780 | 216 |
| 16 | 3700 | not tested | 17 | 250 | not tested |
| 18 | 89 | 16 | 19 | 1300 | not tested |
| 20 | not tested | not tested | 21, isomer 1 | 1.3$^a$ | 1.0 |
| 21, isomer 2 | 6530 | not tested | | | |

$^a$IC$_{50}$ from the diluted FRET assay.

(1r,1'S,4S)-4-(Difluoromethoxy)-6'(3-fluoropropoxy)-5"-methyl-3'H-dispiro[cyclohexane-1,2'-indene-1',2"-imidazol]-4"-amine;

(1r,4r)-6'-(2-Fluoropropoxy)-4-methoxy-5"-methyl-3'H-dispiro[cyclohexane-1,2'-indene-1',2"-imidazol]-4"-amine;

3-[(1r,1'R,4R)-4"-Amino-4-hydroxy-5"-methyl-3'H-dispiro[cyclohexane-1,2'-indene-1',2"-imidazol]-6'-yl]-5-chlorobenzonitrile;

3-[(1r,1'S,4S)-4"-Amino-4-hydroxy-5"-methyl-3'H-dispiro[cyclohexane-1,2'-indene-1',2"-imidazol]-6'-yl]-5-chlorobenzonitrile;

(1r,4r)-6'-Bromo-5"-methyl-4-(propan-2-yloxy)-3'H-dispiro[cyclohexane-1,2'-indene-1',2"-imidazol]-4"-amine;

(1r,4r)-6'-(3-Fluoropropoxy)-5"-methyl-4-(propan-2-yloxy)-3'H-dispiro[cyclohexane-1,2'-indene-1',2"-imidazol]-4"-amine;

(1r,4r)-6'-[(2S)-Butan-2-yloxy]-4-methoxy-5"-methyl-3'H-dispiro[cyclohexane-1 ,2'-indene-1',2"-imidazol]-4"-amine;

(1r,1'R,4R)-4"-Amino-4-methoxy-5"-methyl-3'H-dispiro[cyclohexane-1,2'-indene-1',2"-imidazol]-6'-ol; and (1r,1'S,4S)-4"-Amino-5"-methyl-6'-[5-(prop-1-yn-1-yl)pyridin-3-yl]-3'H-dispiro[cyclohexane-1,2'-indene-1',2"-imidazol]-4-ol, or a pharmaceutically acceptable salt of any foregoing compound.

2. The compound or pharmaceutically acceptable salt thereof according to claim 1, wherein said compound is selected from the group consisting of:

(1r,4r)-4"-Amino-5"-methyl-6'-(2-methylpropoxy)-3'H-dispiro[cyclohexane-1,2'-indene-1',2"-imidazol]-4-ol;

(1r,1'R,4R)-4"-Amino-5"-methyl-6'-(2-methylpropoxy)-3'H-dispiro[cyclohexane-1,2'-indene-1',2"-imidazol]-4-ol;

(1r,1'S,4S)-4"-Amino-5"-methyl-6'-(2-methylpropoxy)-3'H-dispiro[cyclohexane-1,2'-indene-1',2"-imidazol]-4-ol;

(1r,4r)-6'-(2,2-Difluoropropoxy)-4-methoxy-5"-methyl-3'H-dispiro[cyclohexane-1,2'-indene-1',2"-imidazol]-4"-amine;

(1r,4r)-4"-Amino-6'-bromo-5"-methyl-3'H-dispiro[cyclohexane-1,2'-indene-1',2"-imidazol]-4-ol;

(1r,1'R,4R)-4"-Amino-6'-bromo-5"-methyl-3'H-dispiro[cyclohexane-1,2'-indene-1',2"-imidazol]-4-ol;

(1r,1'S,4S)-4"-Amino-6'-bromo-5"-methyl-3'H-dispiro[cyclohexane-1,2'-indene-1',2"-imidazol]-4-ol;

(1r,4r)-4-(Difluoromethoxy)-6'-(3-fluoropropoxy)-5"-methyl-3'H-dispiro[cyclohexane-1,2'-indene-1',2"-imidazol]-4"-amine;

(1r,1'R,4R)-4-(Difluoromethoxy)-6'-(3-fluoropropoxy)-5"-methyl-3'H-dispiro[cyclohexane-1,2'-indene-1',2"-imidazol]-4"-amine;

(1r,1'S,4S)-4-(Difluoromethoxy)-6'-(3-fluoropropoxy)-5"-methyl-3'H-dispiro[cyclohexane-1,2'-indene-1',2"-imidazol]-4"-amine;

(1r,4r)-6'-(2-Fluoropropoxy)-4-methoxy-5"-methyl-3'H-dispiro[cyclohexane-1,2'-indene-1',2"-imidazol]-4"-amine;

3-[(1r,1'R,4R)-4"-Amino-4-hydroxy-5"-methyl-3'H-dispiro[cyclohexane-1,2'-indene-1',2"-imidazol]-6'-yl]-5-chlorobenzonitrile;

3-[(1r,1'S,4S)-4"-Amino-4-hydroxy-5"-methyl-3'H-dispiro[cyclohexane-1,2'-indene-1',2"-imidazol]-6'-yl]-5-chlorobenzonitrile;

(1r,4r)-6'-Bromo-5"-methyl-4-(propan-2-yloxy)-3'H-dispiro[cyclohexane-1,2'-indene-1',2"-imidazol]-4"-amine;

(1r,4-6'-(3-Fluoropropoxy)-5"-methyl-4-(propan-2-yloxy)-3'H-dispiro[cyclohexane-1,2'-indene-1',2"-imidazol]-4"-amine;

(1r,4r)-6'-[(2S)-Butan-2-yloxy]-4-methoxy-5"-methyl-3'H-dispiro[cyclohexane-1,2'-indene-1',2"-imidazol]-4"-amine;

(1r,1'R,4R)-4"-Amino-4-methoxy-5"-methyl-3'H-dispiro[cyclohexane-1,2'-indene-1',2"-imidazol]-6'-ol; and (1r,1'S,4S)-4"-Amino-5"-methyl-6'-[5-(prop-1-yn-1-yl)pyridin-3-yl]-3'H-dispiro[cyclohexane-1,2'-indene-1',2"-imidazol]-4-ol, or a pharmaceutically acceptable salt of any foregoing compound.

3. The compound or pharmaceutically acceptable salt thereof according to claim 1, wherein said compound is (1r,4r)-6'-(2,2-Difluoropropoxy)-4-methoxy-5"-methyl-3'H-dispiro[cyclohexane-1,2'-indene-1',2"-imidazol]-4"-amine:

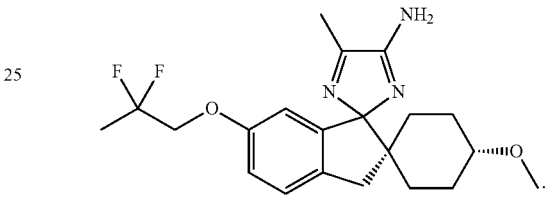

4. The compound or pharmaceutically acceptable salt thereof according to claim 1, wherein said compound is (1r,1'R,4R)-4-Methoxy-5"-methyl-6'-(3,3,3-trifluoropropoxy)-3'H-dispiro[cyclohexane-1,2'-indene-1',2"-imidazol]-4"-amine:

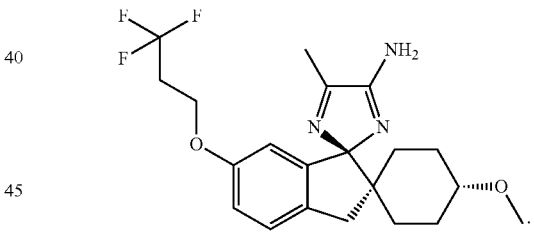

5. A pharmaceutical composition comprising as active ingredient a therapeutically effective amount of a compound according to any one of claims 1 and 2-4, or a pharmaceutically acceptable salt thereof, in association with at least one pharmaceutically acceptable excipient, carrier or diluent.

6. A method of treating Alzheimer's Disease in a patient in need thereof, comprising administering to said patient a therapeutically effective amount of a compound according to any one of claims 1 and 2-4, or a pharmaceutically acceptable salt thereof.

7. A method of treating an Aβ-related pathology in a patient in need thereof, comprising administering to said patient a therapeutically effective amount of a compound according to any one of claims 1 and 2-4, or a pharmaceutically acceptable salt thereof, and at least one cognitive enhancing agent, memory enhancing agent, or choline esterase inhibitor, wherein said Aβ-related pathology is Alzheimer's Disease.

* * * * *